(12) United States Patent
Kraus et al.

(10) Patent No.: US 11,560,594 B2
(45) Date of Patent: Jan. 24, 2023

(54) METHODS OF DETECTING OSTEOARTHRITIS AND PREDICTING PROGRESSION THEREOF

(71) Applicant: Duke University, Durham, NC (US)

(72) Inventors: Virginia B. Kraus, Durham, NC (US); Jonathan B. Catterall, Durham, NC (US); Erik Soderblom, Durham, NC (US); Martin A. Moseley, Durham, NC (US); Sunil Suchindran, Durham, NC (US)

(73) Assignee: Duke University, Durham, NC (US)

( * ) Notice: Subject to any disclaimer, the term of this patent is extended or adjusted under 35 U.S.C. 154(b) by 1172 days.

(21) Appl. No.: 15/548,821

(22) PCT Filed: Feb. 5, 2016

(86) PCT No.: PCT/US2016/016736
§ 371 (c)(1),
(2) Date: Aug. 4, 2017

(87) PCT Pub. No.: WO2016/127035
PCT Pub. Date: Aug. 11, 2016

(65) Prior Publication Data
US 2020/0232034 A1    Jul. 23, 2020

Related U.S. Application Data

(60) Provisional application No. 62/112,445, filed on Feb. 5, 2015, provisional application No. 62/172,394, filed on Jun. 8, 2015.

(51) Int. Cl.
*C12Q 1/6883* (2018.01)
*G01N 33/68* (2006.01)
*A61P 19/02* (2006.01)

(52) U.S. Cl.
CPC ....... *C12Q 1/6883* (2013.01); *G01N 33/6848* (2013.01); *G01N 33/6893* (2013.01);
(Continued)

(58) Field of Classification Search
CPC ............ C12Q 1/6883; C12Q 2600/158; G01N 33/68; G01N 2800/105; G01N 2800/60; A61P 19/02
See application file for complete search history.

(56) References Cited

U.S. PATENT DOCUMENTS 5,869,471 A    2/1999  Hovancik et al.
9,207,247 B2   12/2015  Kraus et al.
(Continued)

FOREIGN PATENT DOCUMENTS

EP         2258863          12/2010
WO    WO-2008074029 A2 *  6/2008    ......... G01N 33/6887

OTHER PUBLICATIONS

Fernandez-Puente et al., J. Proteome Res., 2011, vol. 10:5095-5101.*

(Continued)

*Primary Examiner* — Xiaozhen Xie
(74) *Attorney, Agent, or Firm* — Quarles & Brady LLP

(57) ABSTRACT

Provided herein are methods and biomarkers useful for detecting and diagnosing osteoarthritis and predicting the progression of osteoarthritis in subjects. The diagnoses and predictions of prognosis may be used to develop treatment plans for subjects. Also included are methods of treating subjects and administering pharmaceuticals based on the diagnosis and prognosis predictions.

15 Claims, 2 Drawing Sheets

Specification includes a Sequence Listing.

(52) U.S. Cl.
CPC . *C12Q 2600/158* (2013.01); *G01N 2800/105* (2013.01); *G01N 2800/50* (2013.01); *G01N 2800/56* (2013.01); *G01N 2800/60* (2013.01)

(56) References Cited

U.S. PATENT DOCUMENTS

| | | | |
|---|---|---|---|
| 2004/0242987 A1 | 12/2004 | Liew et al. | |
| 2005/0124071 A1 | 6/2005 | Kraus | |
| 2007/0225206 A1* | 9/2007 | Ling | C12Q 1/6883 435/7.1 |
| 2010/0285477 A1* | 11/2010 | Kouznetsov | C12Q 1/6883 435/6.14 |
| 2011/0189694 A1 | 8/2011 | Woloszczuk et al. | |
| 2012/0190042 A1* | 7/2012 | Gobezie | G01N 33/6896 435/7.4 |
| 2014/0038841 A1 | 2/2014 | Sharif et al. | |

OTHER PUBLICATIONS

Hinton et al., Am. Fam. Physicians, 2002, vol. 65:841-848.*
Tu et al., J. Proteome Res., 2010, vol. 9(10):4982-4991.*
Altman et al. Atlas of individual radiographic features in osteoarthritis, revised. Osteoarthritis Cartilage 2007, 15 Suppl A:A1-56.
Blumbach, K. et al, Ablation of collagen IX and COMP disrupts epiphyseal cartilage architecture Matrix Biol. 27(4): 306-18 (2008).
Carr et al. Targeted peptide measurements in biology and medicine: best practices for mass spectrometry-based assay development using a fit-for-purpose approach. Mol Cell Proteomics 2014, 13(3):907-17.
Catterall et al. Protein Modification by Deamidation Indicates Variations in Joint Extracellular Matrix Turnover. The Journal of Biological Chemistry 287(7):4640-4651 (2012).
Catterall et al. Aspartic acid racemization reveals a high turnover state in knee compared with hip osteoarthritic cartilage. Osteoarthritis Cartilage. Feb. 2016;24(2):374-81.
Catterall, Stabler TV, Flannery CR, Kraus VB. Changes in serum and synovial fluid biomarkers after acute injury (NCT00332254). Arthritis Res Ther 2010;12(6):R229.
Chou et al. Genome-wide expression profiles of subchondral bone in osteoarthritis. Arthritis Res Ther 2013;15(6):R190.
Chou et al. Direct assessment of articular cartilage and underlying subchondral bone reveals a progressive gene expression change in human osteoarthritic knees. Osteoarthritis Cartilage 2013;21(3):450-61.
CS-Szabó et al, Large and small proteoglycans of osteoarthritic and rheumatoid articular cartilage. Arthritis Rheum. 38(5):660-668 (1995).
Di Cesare, P.E., et al, Expression of cartilage oligomeric matrix protein by human synovium FEBS Lett. 412(1):249-252 (1997).
Dicesare, P.E., Expression of cartilage oligomeric matrix protein (COMP) by embryonic and adult osteoblasts. Journal of Orthopeaedic Research 18(5):713-720 (2000).
FDA FaDA. Guidance for Industry: Clinical Development Programs for Drugs, Devices and Biological Products Intended for the Treatment of OA In. Rockville: U.S. Department of Health and Human Services; 1999.
Garnero, P. Biomarkers for osteoporosis management: utility in diagnosis, fracture risk prediction and therapy monitoring. Mol. Diagn. Ther. 2008;12(3):157-70 (2008).
Gobezie, R. et al., "High abundance synovial fluid proteome: Distinct profiles in health and osteoarthritis," Arthritis Research & Therapy 2007, 9:1-15.
Guo, Y. et al, All-trans retinol, vitamin D and other hydrophobic compounds bind in the axial pore of the five-stranded coiled-coil domain of cartilage oligomeric matrix protein. Embo J. 17(18):5265-5272 (1998).
Hermansson et al. Proteomic Analysis of Articular Cartilage Shows Increased Type II Collagen Synthesis in Osteoarthritis and Expression of Inhibin βA (Activin A), a Regulatory Molecule for Chondrocytes. (2004) JBC 279:43514-43521.

Hsueh, Kraus, et al. Elucidating the Molecular Composition of Cartilage by Proteomics Proteome Res. 15, 2, 374-388 (2016).
Huang K, Wu LD. Aggrecanase and aggrecan degradation in osteoarthritis: a review. J Int Med Res 2008;36(6):1149-60.
Hummel, K.M. et al, Analysis of cartilage oligomeric matrix protein (COMP) in synovial fibroblasts and synovial fluids. Br. J. Rheumatol. 37(7):721-728 (1998).
Hunter DJ. Risk stratification for knee osteoarthritis progression: a narrative review. Osteoarthritis Cartilage 2009.
Hunter DJ, Losina E, Guermazi A, Burstein D, Lassere MN, Kraus V. A pathway and approach to biomarker validation and qualification for osteoarthritis clinical trials. Curr Drug Targets 2010;11(5):536-45.
International Search Report and Written Opinion for PCT/US2011/000316 dated Nov. 30, 2011.
International Search Report and Written Opinion for PCT/US16/16736 dated Jul. 12, 2016 (38 pages).
Jordan, J.M. et al. Ethnic and Sex Differences in Serum Levels of Cartilage Oligomeric Matrix Protein. Arthritis and Rheumatism vol. 48, No. 3, pp. 675-681 (2003).
Kellgren, J.H. et al. Radiological assessment of osteo-arthrosis. Ann Rheum Dis 1957, 16(4): 494-502.
Kiani, C. et al, Structure and function of aggrecan. Cell Res. 12(1):19-32 (2002).
Knudson, C.B. et al., Cartilage proteoglycans. Semin. Cell Dev. Biol. 12(2):69-78 (2001).
Koelling, S. et al, Cartilage oligomeric matrix protein is involved in human limb development and in the pathogenesis of osteoarthritis. Arthritis Res. Ther. 8(3): R56 (2006).
Kraus et al. Association of bone scintigraphic abnormalities with knee malalignment and pain. Ann Rheum Dis 2009, 68(11):1673-9.
Kraus et al. The Genetics of Generalized Osteoarthritis (GOGO) study: study design and evaluation of osteoarthritis phenotypes. Osteoarthritis Cartilage 2007, 15(2):120-7.
Larsson S, Englund M, Struglics A, Lohmander LS. Association between synovial fluid levels of aggrecan ARGS fragments and radiographic progression in knee osteoarthritis. Arthritis Res Ther 2010;12(6):R230.
Leslie, M. et al, Expression of cartilage oligomeric matrix protein (COMP) by human embryonic and adult osteoblasts Trans. Orthop. Res. 24:581—(1999).
Lippiello et al, J. Clin. Invest. 593-600 (1977).
Madsen SH, Sumer EU, Bay-Jensen AC, Sondergaard BC, Qvist P, Karsdal MA. Aggrecanase- and matrix metalloproteinase-mediated aggrecan degradation is associated with different molecular characteristics of aggrecan and separated in time ex vivo. Biomarkers 2010;15(3):266-76.
Malashkevich, V. et al, The Crystal Structure of a Five-Stranded Coiled Coil in COMP: A Prototype Ion Channel? Science 274(5288):761-765 (1996).
Mankin, H.J. et al, Biochemical and metabolic abnormalities in articular cartilage from osteoarthritic human hips. III. Distribution and metabolism of amino sugar-containing macromolecules. J. Bone Joint Surg. 63(1) 131-139 (1981).
Maroudas A, Bayliss MT, Uchitel-Kaushansky N, Schneiderman R, Gilav E. Aggrecan turnover in human articular cartilage: use of aspartic acid racemization as a marker of molecular age. Arch Biochem Biophys 1998;350(1):61-71.
McCudden, C.R. et al. Biochemistry of amino acid racemization and clinical application to musculoskeletal disease. Clinical Biochemisty 39:1112-1130 (2006).
Mok et al, J. Biol. Chem. 269(52):33021-33027 (1994).
Nagase, H. & Kashiwagi, M. Aggrecanases and cartilage matrix degradation. Arthritis Res. Ther. 5(2):94-103 (2003).
Özbek, S. et al, Storage function of cartilage oligomeric matrix protein: the crystal structure of the coiled-coil domain in complex with vitamin $D_3$. Embo J. 21(22):5960-5968 (2002).
Poole, Kobayashi et al. Type II collagen degradation and its regulation in articular cartilage in osteoarthritis. Ann Rheum Dis. 2002 61 (Suppl 2): ii78-ii81.
Qoronfleh, W. & Lindpaintner, K. Protein biomarker immunoassays: opportunities and challenges. Drug Discovery World Winter 2010, 19-28.

(56) References Cited

OTHER PUBLICATIONS

Quinn et al. Physical and Biological Regulation of Proteoglycan Turnover around Chondrocytes in Cartilage Explants: Implications for Tissue Degradation and Repair. Ann. N.Y. Acad. Sci. 878:420-441 (1999).

Schmitz, M. et al, Transgenic mice expressing D469Δ mutated cartilage oligomeric matrix protein (COMP) show growth plate abnormalities and sternal malformations. Matrix Biol. 27(2): 67-85 (2008).

Sharif, M. et al, Suggestion of nonlinear or phasic progression of knee osteoarthritis based on measurements of serum cartilage oligomeric matrix protein levels over five years. Arthritis Rheum. 50(8):2479-2488 (2004).

Sivan SS, Tsitron E, Wachtel E, et al. Age-related accumulation of pentosidine in aggrecan and collagen from normal and degenerate human intervertebral discs. Biochemical Journal. 2006;399(Pt 1):29-35.

Sofat N. Analysing the role of endogenous matrix molecules in the development of osteoarthritis. Int J Exp Pathol 2009;90(5):463-79.

Struglics A, Hansson M, Lohmander LS. Human aggrecanase generated synovial fluid fragment levels are elevated directly after knee injuries due to proteolysis both in the inter globular and chondroitin sulfate domains. Osteoarthritis Cartilage 2011; 19(8):1047-57.

Tu, C. et al. Depletion of abundant plasma proteins and limitations of plasma proteomics. J Proteome Res 2010, 9(10):4982-91.

Vilim, V. et al. Monoclonal antibodies to human cartilage oligomeric matric protein: epitope mapping and characterization of sandwich ELISA. Clinica Chimica Acta 2003; vol. 328, pp. 59-69.

Vilim, V et al, Characterization of Monoclonal Antibodies Recognizing Different Fragments of Cartilage Oligomeric Matrix Protein in Human Body Fluids. Archives of biochemisty and Biophysics 341(1):8-16 (1997).

Vilim, V. Serum cartilage oligomeric matrix protein reflects the presence of clinically diagnosed synovitis in patients with knee osteoarthritis. Osteoarthritis Cartilage. Oct. 2001;9(7):612-8.

Office Action for U.S. Appl. No. 13/580,555 dated Feb. 27, 2014 (26 pages).

* cited by examiner

Figure 1. Diagnosis and treatment of Osteoarthritis using the "Progressive Joint Disease Panel"

SEQUENCE LISTING

```
<160> NUMBER OF SEQ ID NOS: 145

<210> SEQ ID NO 1
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: Marker: CRAC1 (CRTAC1)

<400> SEQUENCE: 1

Gly Val Ala Ser Leu Phe Ala Gly Arg
1               5

<210> SEQ ID NO 2
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: CRAC1 (CRTAC1)

<400> SEQUENCE: 2

Ser Ser Pro Tyr Tyr Ala Leu Arg
1               5

<210> SEQ ID NO 3
<211> LENGTH: 19
<212> TYPE: PRT
<213> ORGANISM: Homo sapiens
<220> FEATURE:
<221> NAME/KEY: misc_feature
<222> LOCATION: (1)..(19)
<223> OTHER INFORMATION: Marker: A1BG

<400> SEQUENCE: 3

Ile Phe Phe His Leu Asn Ala Val Ala Leu Gly Asp Gly His Tyr
1               5                   10                  15

Thr Cys Arg

<210> SEQ ID NO 4
```

```
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: A2AP

<400> SEQUENCE: 4

Ser Pro Pro Gly Val Cys Ser Arg
1               5

<210> SEQ ID NO 5
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: A2AP

<400> SEQUENCE: 5

Leu Cys Gln Asp Leu Gly Pro Gly Ala Phe Arg
1               5                   10

<210> SEQ ID NO 6
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: A2GL

<400> SEQUENCE: 6

Val Ala Ala Gly Ala Phe Gln Gly Leu Arg
1               5                   10

<210> SEQ ID NO 7
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: A2GL

<400> SEQUENCE: 7

Ala Leu Gly His Leu Asp Leu Ser Gly Asn Arg
1               5                   10

<210> SEQ ID NO 8
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: AACT

<400> SEQUENCE: 8

Ala Asp Leu Ser Gly Ile Thr Gly Ala Arg
1               5                   10

<210> SEQ ID NO 9
<211> LENGTH: 10
<212> TYPE: PRT
<213> ORGANISM: Homo sapiens
<220> FEATURE:
```

-continued

```
<221> NAME/KEY: misc_feature
<222> LOCATION: (1)..(10)
<223> OTHER INFORMATION: Marker: AACT

<400> SEQUENCE: 9

Asn Leu Ala Val Ser Gln Val Val His Lys
1               5                   10

<210> SEQ ID NO 10
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: AACT

<400> SEQUENCE: 10

Glu Gln Leu Ser Leu Leu Asp Arg
1               5

<210> SEQ ID NO 11
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: Marker: ACTG

<400> SEQUENCE: 11

Val Ala Pro Glu Glu His Pro Val Leu Leu Thr Glu Ala Pro Leu Asn
1               5                   10                  15

Pro Lys

<210> SEQ ID NO 12
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Marker: AFAM

<400> SEQUENCE: 12

Val Asn Cys Leu Gln Thr Arg
1               5

<210> SEQ ID NO 13
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Marker: AMBP

<400> SEQUENCE: 13

Ala Phe Ile Gln Leu Trp Ala Phe Asp Ala Val Lys
1               5                   10

<210> SEQ ID NO 14
<211> LENGTH: 10
<212> TYPE: PRT
<213> ORGANISM: Homo sapiens
<220> FEATURE:
<221> NAME/KEY: misc_feature
<222> LOCATION: (1)..(10)
```

<223> OTHER INFORMATION: Marker: ANT3

<400> SEQUENCE: 14

Ala Thr Glu Asp Glu Gly Ser Glu Gln Lys
1               5                   10

<210> SEQ ID NO 15
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Marker: APOB

<400> SEQUENCE: 15

Leu Ala Ile Pro Glu Gly Lys
1               5

<210> SEQ ID NO 16
<211> LENGTH: 13
<212> TYPE: PRT
<213> ORGANISM: Homo sapiens
<220> FEATURE:
<221> NAME/KEY: misc_feature
<222> LOCATION: (1)..(13)
<223> OTHER INFORMATION: Marker: APOB

<400> SEQUENCE: 16

Trp Asn Phe Tyr Tyr Ser Pro Gln Ser Ser Pro Asp Lys
1               5                   10

<210> SEQ ID NO 17
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: Marker: APOE

<400> SEQUENCE: 17

Leu Gln Ala Glu Ala Phe Gln Ala Arg
1               5

<210> SEQ ID NO 18
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: Marker: APOH

<400> SEQUENCE: 18

Ala Thr Phe Gly Cys His Asp Gly Tyr Ser Leu Asp Gly Pro Glu Glu
1               5                   10                  15

Ile Glu Cys Thr Lys
            20

<210> SEQ ID NO 19
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: B2MG

```
<400> SEQUENCE: 19

Val Glu His Ser Asp Leu Ser Phe Ser Lys
1               5                   10

<210> SEQ ID NO 20
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: C1QC

<400> SEQUENCE: 20

Val Val Thr Phe Cys Gly His Thr Ser Lys
1               5                   10

<210> SEQ ID NO 21
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: C1R

<400> SEQUENCE: 21

Asn Ile Gly Glu Phe Cys Gly Lys
1               5

<210> SEQ ID NO 22
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Marker: C1R

<400> SEQUENCE: 22

Gly Leu Thr Leu His Leu Lys
1               5

<210> SEQ ID NO 23
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Marker: C1R

<400> SEQUENCE: 23

Gly Tyr Gly Phe Tyr Thr Lys
1               5

<210> SEQ ID NO 24
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Marker: C1RL

<400> SEQUENCE: 24

Gly Ser Glu Ala Ile Asn Ala Pro Gly Asp Asn Pro Ala Lys
```

```
<210> SEQ ID NO 25
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Marker: C4BPA

<400> SEQUENCE: 25

Leu Ser Leu Glu Ile Glu Gln Leu Glu Leu Gln Arg
1               5                   10

<210> SEQ ID NO 26
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: Marker: C4BPA

<400> SEQUENCE: 26

Gly Val Gly Trp Ser His Pro Leu Pro Gln Cys Glu Ile Val Lys
1               5                   10                  15

<210> SEQ ID NO 27
<211> LENGTH: 17
<212> TYPE: PRT
<213> ORGANISM: Homo sapiens
<220> FEATURE:
<221> NAME/KEY: misc_feature
<222> LOCATION: (1)..(17)
<223> OTHER INFORMATION: Marker: C4BPB

<400> SEQUENCE: 27

Ser Gln Cys Leu Glu Asp His Thr Trp Ala Pro Pro Phe Pro Ile Cys
1               5                   10                  15

Lys

<210> SEQ ID NO 28
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Marker: CD44

<400> SEQUENCE: 28

Tyr Gly Phe Ile Glu Gly His Val Val Ile Pro Arg
1               5                   10

<210> SEQ ID NO 29
<211> LENGTH: 23
<212> TYPE: PRT
<213> ORGANISM: Homo sapiens
<220> FEATURE:
<221> NAME/KEY: misc_feature
<222> LOCATION: (1)..(23)
<223> OTHER INFORMATION: Marker: CERU

<400> SEQUENCE: 29

His Tyr Tyr Ile Ala Ala Glu Glu Ile Ile Trp Asn Tyr Ala Pro Ser
1               5                   10                  15
```

```
Gly Ile Asp Ile Phe Thr Lys
            20
```

<210> SEQ ID NO 30
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: CERU

<400> SEQUENCE: 30

```
Glu Tyr Thr Asp Ala Ser Phe Thr Asn Arg
1               5                   10
```

<210> SEQ ID NO 31
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Marker: CERU

<400> SEQUENCE: 31

```
Asp Ile Ala Ser Gly Leu Ile Gly Pro Leu Ile Ile Cys Lys
1               5                   10
```

<210> SEQ ID NO 32
<211> LENGTH: 13
<212> TYPE: PRT
<213> ORGANISM: Homo sapiens
<220> FEATURE:
<221> NAME/KEY: misc_feature
<222> LOCATION: (1)..(13)
<223> OTHER INFORMATION: Marker: CERU

<400> SEQUENCE: 32

```
Gly Ala Tyr Pro Leu Ser Ile Glu Pro Ile Gly Val Arg
1               5                   10
```

<210> SEQ ID NO 33
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Marker: CERU

<400> SEQUENCE: 33

```
Glu Val Gly Pro Thr Asn Ala Asp Pro Val Cys Leu Ala Lys
1               5                   10
```

<210> SEQ ID NO 34
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: CFAB

<400> SEQUENCE: 34

```
Gln Leu Asn Glu Ile Asn Tyr Glu Asp His Lys
1               5                   10
```

-continued

```
<210> SEQ ID NO 35
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: CFAH

<400> SEQUENCE: 35

Cys Leu Pro Val Thr Ala Pro Glu Asn Gly Lys
1               5                   10

<210> SEQ ID NO 36
<211> LENGTH: 13
<212> TYPE: PRT
<213> ORGANISM: Homo sapiens
<220> FEATURE:
<221> NAME/KEY: misc_feature
<222> LOCATION: (1)..(13)
<223> OTHER INFORMATION: Marker: CFAI

<400> SEQUENCE: 36

His Gly Asn Thr Asp Ser Glu Gly Ile Val Glu Val Lys
1               5                   10

<210> SEQ ID NO 37
<211> LENGTH: 13
<212> TYPE: PRT
<213> ORGANISM: Homo sapiens
<220> FEATURE:
<221> NAME/KEY: misc_feature
<222> LOCATION: (1)..(13)
<223> OTHER INFORMATION: Marker: CFAI

<400> SEQUENCE: 37

Ala Gln Leu Gly Asp Leu Pro Trp Gln Val Ala Ile Lys
1               5                   10

<210> SEQ ID NO 38
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: CILP1

<400> SEQUENCE: 38

Ile Val Gly Pro Leu Glu Val Asn Val Arg
1               5                   10

<210> SEQ ID NO 39
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: C1S

<400> SEQUENCE: 39

Leu Leu Glu Val Pro Glu Gly Arg
1               5

<210> SEQ ID NO 40
<211> LENGTH: 11
<212> TYPE: PRT
<213> ORGANISM: Homo sapiens
```

-continued

```
<220> FEATURE:
<221> NAME/KEY: misc_feature
<222> LOCATION: (1)..(11)
<223> OTHER INFORMATION: Marker: CNDP1

<400> SEQUENCE: 40

Ala Leu Glu Gln Asp Leu Pro Val Asn Ile Lys
1               5                   10

<210> SEQ ID NO 41
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Marker: CO2

<400> SEQUENCE: 41

Ser Ser Gly Gln Trp Gln Thr Pro Gly Ala Thr Arg
1               5                   10

<210> SEQ ID NO 42
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: Marker: CO3

<400> SEQUENCE: 42

Asp Gly Asn Asp His Ser Leu Trp Arg
1               5

<210> SEQ ID NO 43
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Marker: CO4B

<400> SEQUENCE: 43

Leu Val Asn Gly Gln Ser His Ile Ser Leu Ser Lys
1               5                   10

<210> SEQ ID NO 44
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: CO5

<400> SEQUENCE: 44

Gly Ile Tyr Gly Thr Ile Ser Arg
1               5

<210> SEQ ID NO 45
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: CO6
```

<400> SEQUENCE: 45

Thr Leu Leu Pro Val Ser Lys Pro Glu Ile Arg
1               5                   10

<210> SEQ ID NO 46
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Marker: CO7

<400> SEQUENCE: 46

Ile Ile His Phe Gly Thr Arg
1               5

<210> SEQ ID NO 47
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: Marker: CO8

<400> SEQUENCE: 47

Phe Ser Tyr Ser Ser Gly His Val His Leu Ser Ser Glu Asn Lys
1               5                   10                  15

<210> SEQ ID NO 48
<211> LENGTH: 16
<212> TYPE: PRT
<213> ORGANISM: Homo sapiens
<220> FEATURE:
<221> NAME/KEY: misc_feature
<222> LOCATION: (1)..(16)
<223> OTHER INFORMATION: Marker: CO9

<400> SEQUENCE: 48

Ser Tyr Phe Pro Glu Ser Trp Leu Trp Glu Val His Leu Val Pro Arg
1               5                   10                  15

<210> SEQ ID NO 49
<211> LENGTH: 13
<212> TYPE: PRT
<213> ORGANISM: Homo sapiens
<220> FEATURE:
<221> NAME/KEY: misc_feature
<222> LOCATION: (1)..(13)
<223> OTHER INFORMATION: Marker: CO6A3

<400> SEQUENCE: 49

Glu Val Gln Val Phe Glu Ile Thr Glu Asn Ser Ala Lys
1               5                   10

<210> SEQ ID NO 50
<211> LENGTH: 19
<212> TYPE: PRT
<213> ORGANISM: Homo sapiens
<220> FEATURE:
<221> NAME/KEY: misc_feature
<222> LOCATION: (1)..(19)
<223> OTHER INFORMATION: Marker: CO6A4

<400> SEQUENCE: 50

Leu Leu Pro Ser Phe Val Ser Ser Glu Asn Ala Phe Tyr Leu Ser Pro

```
1               5                  10                 15

Asp Ile Arg

<210> SEQ ID NO 51
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Marker: CO8B

<400> SEQUENCE: 51

Gly Ile Leu Asn Glu Ile Lys
1               5

<210> SEQ ID NO 52
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: CO8G

<400> SEQUENCE: 52

Gln Leu Tyr Gly Asp Thr Gly Val Leu Gly Arg
1               5                  10

<210> SEQ ID NO 53
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: CO9

<400> SEQUENCE: 53

Phe Thr Pro Thr Glu Thr Asn Lys
1               5

<210> SEQ ID NO 54
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Marker: COMP

<400> SEQUENCE: 54

Asn Ala Leu Trp His Thr Gly Asp Thr Glu Ser Gln Val Arg
1               5                  10

<210> SEQ ID NO 55
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: COMP

<400> SEQUENCE: 55

Ser Ser Thr Gly Pro Gly Glu Gln Leu Arg
1               5                  10
```

```
<210> SEQ ID NO 56
<211> LENGTH: 32
<212> TYPE: PRT
<213> ORGANISM: Homo sapiens
<220> FEATURE:
<221> NAME/KEY: misc_feature
<222> LOCATION: (1)..(32)
<223> OTHER INFORMATION: Marker: COMP

<400> SEQUENCE: 56

Ser Asn Pro Asp Gln Ala Asp Val Asp His Asp Phe Val Gly Asp Ala
1               5                   10                  15

Cys Asp Ser Asp Gln Asp Gln Asp Gly Asp Gly His Gln Asp Ser Arg
            20                  25                  30

<210> SEQ ID NO 57
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: CXCL7

<400> SEQUENCE: 57

Asn Ile Gln Ser Leu Glu Val Ile Gly Lys
1               5                   10

<210> SEQ ID NO 58
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: Marker: DOPO

<400> SEQUENCE: 58

Val Ile Ser Thr Leu Glu Glu Pro Thr Pro Gln Cys Pro Thr Ser Gln
1               5                   10                  15

Gly Arg

<210> SEQ ID NO 59
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: Marker: ECM1

<400> SEQUENCE: 59

Phe Cys Glu Ala Glu Phe Ser Val Lys
1               5

<210> SEQ ID NO 60
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: FA12

<400> SEQUENCE: 60

Cys Leu Glu Val Glu Gly His Arg
1               5
```

```
<210> SEQ ID NO 61
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: FA5

<400> SEQUENCE: 61

Ser Glu Ala Tyr Asn Thr Phe Ser Glu Arg
1               5                   10

<210> SEQ ID NO 62
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Marker: FA6

<400> SEQUENCE: 62

Glu Phe Asn Pro Leu Val Ile Val Gly Leu Ser Lys
1               5                   10

<210> SEQ ID NO 63
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: FBLN1

<400> SEQUENCE: 63

Thr Gly Tyr Tyr Phe Asp Gly Ile Ser Arg
1               5                   10

<210> SEQ ID NO 64
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Marker: FBLN3

<400> SEQUENCE: 64

Asn Pro Cys Gln Asp Pro Tyr Ile Leu Thr Pro Glu Asn Arg
1               5                   10

<210> SEQ ID NO 65
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: Marker: FBLN4

<400> SEQUENCE: 65

Ala Asp Gln Val Cys Ile Asn Leu Arg
1               5

<210> SEQ ID NO 66
<211> LENGTH: 18
```

```
<212> TYPE: PRT
<213> ORGANISM: Homo sapiens
<220> FEATURE:
<221> NAME/KEY: misc_feature
<222> LOCATION: (1)..(18)
<223> OTHER INFORMATION: Marker: FCGBP

<400> SEQUENCE: 66

Val Thr Ala Ser Ser Pro Val Ala Val Leu Ser Gly His Ser Cys Ala
1               5                   10                  15
Gln Lys

<210> SEQ ID NO 67
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: Marker: FCN3

<400> SEQUENCE: 67

Thr Phe Ala His Tyr Ala Thr Phe Arg
1               5

<210> SEQ ID NO 68
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: FETUA

<400> SEQUENCE: 68

His Thr Leu Asn Gln Ile Asp Glu Val Lys
1               5                   10

<210> SEQ ID NO 69
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Marker: FETUA

<400> SEQUENCE: 69

Phe Ser Val Val Tyr Ala Lys
1               5

<210> SEQ ID NO 70
<211> LENGTH: 16
<212> TYPE: PRT
<213> ORGANISM: Homo sapiens
<220> FEATURE:
<221> NAME/KEY: misc_feature
<222> LOCATION: (1)..(16)
<223> OTHER INFORMATION: Marker: FINC

<400> SEQUENCE: 70

Glu Tyr Leu Gly Ala Ile Cys Ser Cys Thr Cys Phe Gly Gly Gln Arg
1               5                   10                  15

<210> SEQ ID NO 71
<211> LENGTH: 7
<212> TYPE: PRT
<213> ORGANISM: Homo sapiens
```

```
<220> FEATURE:
<221> NAME/KEY: misc_feature
<222> LOCATION: (1)..(7)
<223> OTHER INFORMATION: Marker: FINC

<400> SEQUENCE: 71

Ile Gly Asp Thr Trp Ser Lys
1               5

<210> SEQ ID NO 72
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: GELS

<400> SEQUENCE: 72

Gly Gly Val Ala Ser Gly Phe Lys
1               5

<210> SEQ ID NO 73
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: Marker: HABP2

<400> SEQUENCE: 73

Phe Cys Glu Ile Gly Ser Asp Asp Cys Tyr Val Gly Asp Gly Tyr Ser
1               5                   10                  15

Tyr Arg

<210> SEQ ID NO 74
<211> LENGTH: 13
<212> TYPE: PRT
<213> ORGANISM: Homo sapiens
<220> FEATURE:
<221> NAME/KEY: misc_feature
<222> LOCATION: (1)..(13)
<223> OTHER INFORMATION: Marker: HABP3

<400> SEQUENCE: 74

Gly Gln Cys Leu Ile Thr Gln Ser Pro Pro Tyr Tyr Arg
1               5                   10

<210> SEQ ID NO 75
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: HEMO

<400> SEQUENCE: 75

Gln Gly His Asn Ser Val Phe Leu Ile Lys
1               5                   10

<210> SEQ ID NO 76
<211> LENGTH: 7
<212> TYPE: PRT
<213> ORGANISM: Homo sapiens
<220> FEATURE:
<221> NAME/KEY: misc_feature
```

```
<222> LOCATION: (1)..(7)
<223> OTHER INFORMATION: Marker: HEP2

<400> SEQUENCE: 76

Asn Phe Gly Tyr Thr Leu Arg
1               5

<210> SEQ ID NO 77
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: Marker: HEP2

<400> SEQUENCE: 77

Phe Thr Val Asp Arg Pro Phe Leu Phe Leu Ile Tyr Glu His Arg
1               5                   10                  15

<210> SEQ ID NO 78
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: Marker: HGFA

<400> SEQUENCE: 78

Tyr Ile Pro Tyr Thr Leu Tyr Ser Val Phe Asn Pro Ser Asp His Asp
1               5                   10                  15

Leu Val Leu Ile Arg
            20

<210> SEQ ID NO 79
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Marker: HRG

<400> SEQUENCE: 79

Asp Ser Pro Val Leu Ile Asp Phe Phe Glu Asp Thr Glu Arg
1               5                   10

<210> SEQ ID NO 80
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Marker: HRG

<400> SEQUENCE: 80

Gly Gly Glu Gly Thr Gly Tyr Phe Val Asp Phe Ser Val Arg
1               5                   10

<210> SEQ ID NO 81
<211> LENGTH: 11
<212> TYPE: PRT
<213> ORGANISM: Homo sapiens
<220> FEATURE:
<221> NAME/KEY: misc_feature
<222> LOCATION: (1)..(11)
```

<223> OTHER INFORMATION: Marker: HRG

<400> SEQUENCE: 81

Tyr Trp Asn Asp Cys Glu Pro Pro Asp Ser Arg
1               5                   10

<210> SEQ ID NO 82
<211> LENGTH: 20
<212> TYPE: PRT
<213> ORGANISM: Homo sapiens
<220> FEATURE:
<221> NAME/KEY: misc_feature
<222> LOCATION: (1)..(20)
<223> OTHER INFORMATION: Marker: HRG

<400> SEQUENCE: 82

Gly Glu Val Leu Pro Leu Pro Glu Ala Asn Phe Pro Ser Phe Pro Leu
1               5                   10                  15

Pro His His Lys
            20

<210> SEQ ID NO 83
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Marker: HRG

<400> SEQUENCE: 83

Ser Ser Thr Thr Lys Pro Pro Phe Lys Pro His Gly Ser Arg
1               5                   10

<210> SEQ ID NO 84
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Marker: IC1

<400> SEQUENCE: 84

Leu Val Leu Leu Asn Ala Ile Tyr Leu Ser Ala Lys
1               5                   10

<210> SEQ ID NO 85
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Marker: ITIH1

<400> SEQUENCE: 85

Val Thr Phe Gln Leu Thr Tyr Glu Glu Val Leu Lys
1               5                   10

<210> SEQ ID NO 86
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: ITIH4

-continued

<400> SEQUENCE: 86

Phe Lys Pro Thr Leu Ser Gln Gln Gln Lys
1               5                   10

<210> SEQ ID NO 87
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Marker: KLKB1

<400> SEQUENCE: 87

Val Ser Glu Gly Asn His Asp Ile Ala Leu Ile Lys
1               5                   10

<210> SEQ ID NO 88
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: Marker: KNG1

<400> SEQUENCE: 88

Leu Asp Asp Asp Leu Glu His Gln Gly Gly His Val Leu Asp His Gly
1               5                   10                  15

His Lys

<210> SEQ ID NO 89
<211> LENGTH: 16
<212> TYPE: PRT
<213> ORGANISM: Homo sapiens
<220> FEATURE:
<221> NAME/KEY: misc_feature
<222> LOCATION: (1)..(16)
<223> OTHER INFORMATION: Marker: LAMA2

<400> SEQUENCE: 89

Thr Pro Tyr Asn Ile Leu Ser Ser Pro Asp Tyr Val Gly Val Thr Lys
1               5                   10                  15

<210> SEQ ID NO 90
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: Marker: LUM

<400> SEQUENCE: 90

Ile Leu Gly Pro Leu Ser Tyr Ser Lys
1               5

<210> SEQ ID NO 91
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: LUM

<400> SEQUENCE: 91

```
Val Ala Asn Glu Val Thr Leu Asn
1               5

<210> SEQ ID NO 92
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: LUM

<400> SEQUENCE: 92

Ser Leu Glu Asp Leu Gln Leu Thr His Asn Lys
1               5                  10

<210> SEQ ID NO 93
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: LYAM1

<400> SEQUENCE: 93

Ala Glu Ile Glu Tyr Leu Glu Lys
1               5

<210> SEQ ID NO 94
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: Marker: MASP1

<400> SEQUENCE: 94

Thr Gly Val Ile Thr Ser Pro Asp Phe Pro Asn Pro Tyr Pro Lys
1               5                  10                  15

<210> SEQ ID NO 95
<211> LENGTH: 16
<212> TYPE: PRT
<213> ORGANISM: Homo sapiens
<220> FEATURE:
<221> NAME/KEY: misc_feature
<222> LOCATION: (1)..(16)
<223> OTHER INFORMATION: Marker: PCOC1

<400> SEQUENCE: 95

Thr Gly Gly Leu Asp Leu Pro Ser Pro Pro Thr Gly Ala Ser Leu Lys
1               5                  10                  15

<210> SEQ ID NO 96
<211> LENGTH: 21
<212> TYPE: PRT
<213> ORGANISM: Homo sapiens
<220> FEATURE:
<221> NAME/KEY: misc_feature
<222> LOCATION: (1)..(21)
<223> OTHER INFORMATION: Marker: PGCA

<400> SEQUENCE: 96

Val Ser Leu Pro Asn Tyr Pro Ala Ile Pro Ser Asp Ala Thr Leu Glu
1               5                  10                  15
```

```
Val Gln Ser Leu Arg
            20

<210> SEQ ID NO 97
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: PGCA

<400> SEQUENCE: 97

Glu Val Val Leu Leu Val Ala Thr Glu Gly Arg
1               5                   10

<210> SEQ ID NO 98
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: Marker: PHLD

<400> SEQUENCE: 98

Phe Gly Ser Ser Leu Ile Thr Val Arg
1               5

<210> SEQ ID NO 99
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: PLF4

<400> SEQUENCE: 99

Ile Cys Leu Asp Leu Gln Ala Pro Leu Tyr Lys
1               5                   10

<210> SEQ ID NO 100
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: PLMN

<400> SEQUENCE: 100

His Ser Ile Phe Thr Pro Glu Thr Asn Pro Arg
1               5                   10

<210> SEQ ID NO 101
<211> LENGTH: 17
<212> TYPE: PRT
<213> ORGANISM: Homo sapiens
<220> FEATURE:
<221> NAME/KEY: misc_feature
<222> LOCATION: (1)..(17)
<223> OTHER INFORMATION: Marker: PRG4

<400> SEQUENCE: 101

Ile Thr Glu Val Trp Gly Ile Pro Ser Pro Ile Asp Thr Val Phe Thr
1               5                   10                  15

Arg
```

<210> SEQ ID NO 102
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: PRG4

<400> SEQUENCE: 102

Asp Gln Tyr Tyr Asn Ile Asp Val Pro Ser Arg
1               5                   10

<210> SEQ ID NO 103
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: RET4

<400> SEQUENCE: 103

Leu Ile Val His Asn Gly Tyr Cys Asp Gly Arg
1               5                   10

<210> SEQ ID NO 104
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Marker: SAMP

<400> SEQUENCE: 104

Ala Tyr Ser Asp Leu Ser Arg
1               5

<210> SEQ ID NO 105
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: Marker: SHBG

<400> SEQUENCE: 105

Ile Ala Leu Gly Gly Leu Leu Phe Pro Ala Ser Asn Leu Arg
1               5                   10

<210> SEQ ID NO 106
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Marker: TENX

<400> SEQUENCE: 106

Thr Val Thr Val Glu Asp Leu Glu Pro Gly Lys
1               5                   10

<210> SEQ ID NO 107
<211> LENGTH: 12

```
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Marker: TETN

<400> SEQUENCE: 107

Thr Phe His Glu Ala Ser Glu Asp Cys Ile Ser Arg
1               5                   10

<210> SEQ ID NO 108
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: THBG

<400> SEQUENCE: 108

Asn Ala Leu Ala Leu Phe Val Leu Pro Lys
1               5                   10

<210> SEQ ID NO 109
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: THBG

<400> SEQUENCE: 109

Ala Val Leu His Ile Gly Glu Lys
1               5

<210> SEQ ID NO 110
<211> LENGTH: 19
<212> TYPE: PRT
<213> ORGANISM: Homo sapiens
<220> FEATURE:
<221> NAME/KEY: misc_feature
<222> LOCATION: (1)..(19)
<223> OTHER INFORMATION: Marker: THRB

<400> SEQUENCE: 110

Asn Pro Asp Ser Ser Thr Thr Gly Pro Trp Cys Tyr Thr Thr Asp Pro
1               5                   10                  15

Thr Val Arg

<210> SEQ ID NO 111
<211> LENGTH: 12
<212> TYPE: PRT
<213> ORGANISM: Homo sapiens
<220> FEATURE:
<221> NAME/KEY: misc_feature
<222> LOCATION: (1)..(12)
<223> OTHER INFORMATION: Marker: TIMP1

<400> SEQUENCE: 111

Gly Phe Gln Ala Leu Gly Asp Ala Ala Asp Ile Arg
1               5                   10

<210> SEQ ID NO 112
<211> LENGTH: 12
<212> TYPE: PRT
<213> ORGANISM: Homo sapiens
```

```
<220> FEATURE:
<221> NAME/KEY: misc_feature
<222> LOCATION: (1)..(12)
<223> OTHER INFORMATION: Marker: TSP1

<400> SEQUENCE: 112

Phe Val Phe Gly Thr Thr Pro Glu Asp Ile Leu Arg
1               5                   10

<210> SEQ ID NO 113
<211> LENGTH: 17
<212> TYPE: PRT
<213> ORGANISM: Homo sapiens
<220> FEATURE:
<221> NAME/KEY: misc_feature
<222> LOCATION: (1)..(17)
<223> OTHER INFORMATION: Marker: TSP4

<400> SEQUENCE: 113

Asp Val Asp Ile Asp Ser Tyr Pro Asp Glu Glu Leu Pro Cys Ser Ala
1               5                   10                  15

Arg

<210> SEQ ID NO 114
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: Marker: TSP4

<400> SEQUENCE: 114

Ala Val Ala Glu Pro Gly Ile Gln Leu Lys
1               5                   10

<210> SEQ ID NO 115
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Marker: VTDB

<400> SEQUENCE: 115

Glu Leu Pro Glu His Thr Val Lys
1               5

<210> SEQ ID NO 116
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Marker: VTDB

<400> SEQUENCE: 116

Val Leu Glu Pro Thr Leu Lys
1               5

<210> SEQ ID NO 117
<211> LENGTH: 8
<212> TYPE: PRT
<213> ORGANISM: Homo sapiens
<220> FEATURE:
<221> NAME/KEY: misc_feature
```

```
<222> LOCATION: (1)..(8)
<223> OTHER INFORMATION: Marker: VTDB

<400> SEQUENCE: 117

Leu Cys Asp Asn Leu Ser Thr Lys
1               5

<210> SEQ ID NO 118
<211> LENGTH: 20
<212> TYPE: PRT
<213> ORGANISM: Homo sapiens
<220> FEATURE:
<221> NAME/KEY: misc_feature
<222> LOCATION: (1)..(20)
<223> OTHER INFORMATION: Marker: VTDB

<400> SEQUENCE: 118

Ser Cys Glu Ser Asn Ser Pro Phe Pro Val His Pro Gly Thr Ala Glu
1               5                   10                  15

Cys Cys Thr Lys
            20

<210> SEQ ID NO 119
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: Marker: VTDB

<400> SEQUENCE: 119

Ser Leu Gly Glu Cys Cys Asp Val Glu Asp Ser Thr Thr Cys Phe Asn
1               5                   10                  15

Ala Lys

<210> SEQ ID NO 120
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Marker: VTNC

<400> SEQUENCE: 120

Gln Pro Gln Phe Ile Ser Arg
1               5

<210> SEQ ID NO 121
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: Marker: ZA2G

<400> SEQUENCE: 121

Asp Ile Val Glu Tyr Tyr Asn Asp Ser Asn Gly Ser His Val Leu Gln
1               5                   10                  15

Gly Arg

<210> SEQ ID NO 122
<211> LENGTH: 7
<212> TYPE: PRT
```

```
<213> ORGANISM: Homo sapiens
<220> FEATURE:
<221> NAME/KEY: misc_feature
<222> LOCATION: (1)..(7)
<223> OTHER INFORMATION: Marker: ZPI

<400> SEQUENCE: 122

Val Val Asn Pro Thr Leu Leu
1               5

<210> SEQ ID NO 123
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: C1QC_HUMAN

<400> SEQUENCE: 123

Phe Gln Ser Val Phe Thr Val Thr Arg
1               5

<210> SEQ ID NO 124
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: ADIPO_HUMAN

<400> SEQUENCE: 124

Ile Phe Tyr Asn Gln Gln Asn His Tyr Asp Gly Ser Thr Gly Lys
1               5                   10                  15

<210> SEQ ID NO 125
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: CNDP1_HUMAN

<400> SEQUENCE: 125

Glu Trp Val Ala Ile Glu Ser Asp Ser Val Gln Pro Val Pro Arg
1               5                   10                  15

<210> SEQ ID NO 126
<211> LENGTH: 20
<212> TYPE: PRT
<213> ORGANISM: Homo sapiens
<220> FEATURE:
<221> NAME/KEY: misc_feature
<222> LOCATION: (1)..(20)
<223> OTHER INFORMATION: CNDP1_HUMAN

<400> SEQUENCE: 126

Ser Val Val Leu Ile Pro Leu Gly Ala Val Asp Asp Gly Glu His Ser
1               5                   10                  15

Gln Asn Glu Lys
            20

<210> SEQ ID NO 127
<211> LENGTH: 11
<212> TYPE: PRT
<213> ORGANISM: Homo sapiens
```

```
<220> FEATURE:
<221> NAME/KEY: misc_feature
<222> LOCATION: (1)..(11)
<223> OTHER INFORMATION: APOA4_HUMAN

<400> SEQUENCE: 127

Leu Val Pro Phe Ala Thr Glu Leu His Glu Arg
1               5                   10

<210> SEQ ID NO 128
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: CD14_HUMAN

<400> SEQUENCE: 128

Val Leu Ser Ile Ala Gln Ala His Ser Pro Ala Phe Ser Cys Glu Gln
1               5                   10                  15

Val Arg

<210> SEQ ID NO 129
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: TSP1_HUMAN

<400> SEQUENCE: 129

Ser Ile Thr Leu Phe Val Gln Glu Asp Arg
1               5                   10

<210> SEQ ID NO 130
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: K2C1_HUMAN

<400> SEQUENCE: 130

Ala Glu Ala Glu Ser Leu Tyr Gln Ser Lys
1               5                   10

<210> SEQ ID NO 131
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: TSP1_HUMAN

<400> SEQUENCE: 131

Asn Ala Leu Trp His Thr Gly Asn Thr Pro Gly Gln Val Arg
1               5                   10

<210> SEQ ID NO 132
<211> LENGTH: 10
<212> TYPE: PRT
<213> ORGANISM: Homo sapiens
<220> FEATURE:
<221> NAME/KEY: misc_feature
```

```
<222> LOCATION: (1)..(10)
<223> OTHER INFORMATION: CNDP1_HUMAN

<400> SEQUENCE: 132

Ala Ile His Leu Asp Leu Glu Glu Tyr Arg
1               5                   10

<210> SEQ ID NO 133
<211> LENGTH: 13
<212> TYPE: PRT
<213> ORGANISM: Homo sapiens
<220> FEATURE:
<221> NAME/KEY: misc_feature
<222> LOCATION: (1)..(13)
<223> OTHER INFORMATION: TSP1_HUMAN

<400> SEQUENCE: 133

Ala Gly Thr Leu Asp Leu Ser Leu Thr Val Gln Gly Lys
1               5                   10

<210> SEQ ID NO 134
<211> LENGTH: 13
<212> TYPE: PRT
<213> ORGANISM: Homo sapiens
<220> FEATURE:
<221> NAME/KEY: misc_feature
<222> LOCATION: (1)..(13)
<223> OTHER INFORMATION: CBG_HUMAN

<400> SEQUENCE: 134

Glu Glu Asn Phe Tyr Val Asp Glu Thr Thr Val Val Lys
1               5                   10

<210> SEQ ID NO 135
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: CHLE_HUMAN

<400> SEQUENCE: 135

Asp Asn Asn Ser Ile Ile Thr Arg
1               5

<210> SEQ ID NO 136
<211> LENGTH: 24
<212> TYPE: PRT
<213> ORGANISM: Homo sapiens
<220> FEATURE:
<221> NAME/KEY: misc_feature
<222> LOCATION: (1)..(24)
<223> OTHER INFORMATION: SHBG_HUMAN

<400> SEQUENCE: 136

Val Val Leu Ser Ser Gly Ser Gly Pro Gly Leu Asp Leu Pro Leu Val
1               5                   10                  15

Leu Gly Leu Pro Leu Gln Leu Lys
            20

<210> SEQ ID NO 137
<211> LENGTH: 12
<212> TYPE: PRT
<213> ORGANISM: Homo sapiens
<220> FEATURE:
<221> NAME/KEY: misc_feature
<222> LOCATION: (1)..(12)
```

```
<223> OTHER INFORMATION: TSP1_HUMAN

<400> SEQUENCE: 137

Asp Asn Cys Gln Tyr Val Tyr Asn Val Asp Gln Arg
1               5                  10

<210> SEQ ID NO 138
<211> LENGTH: 26
<212> TYPE: PRT
<213> ORGANISM: Homo sapiens
<220> FEATURE:
<221> NAME/KEY: misc_feature
<222> LOCATION: (1)..(26)
<223> OTHER INFORMATION: SHBG_HUMAN

<400> SEQUENCE: 138

Leu Phe Leu Gly Ala Leu Pro Gly Glu Asp Ser Ser Thr Ser Phe Cys
1               5                  10                  15

Leu Asn Gly Leu Trp Ala Gln Gly Gln Arg
            20                  25

<210> SEQ ID NO 139
<211> LENGTH: 20
<212> TYPE: PRT
<213> ORGANISM: Homo sapiens
<220> FEATURE:
<221> NAME/KEY: misc_feature
<222> LOCATION: (1)..(20)
<223> OTHER INFORMATION: FA11_HUMAN

<400> SEQUENCE: 139

His Asn Glu Val Trp His Leu Val Gly Ile Thr Ser Trp Gly Glu Gly
1               5                  10                  15

Cys Ala Gln Arg
            20

<210> SEQ ID NO 140
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: TSP1_HUMAN

<400> SEQUENCE: 140

Gly Pro Asp Pro Ser Ser Pro Ala Phe Arg
1               5                  10

<210> SEQ ID NO 141
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: PLF4_HUMAN

<400> SEQUENCE: 141

His Ile Thr Ser Leu Glu Val Ile Lys
1               5

<210> SEQ ID NO 142
<211> LENGTH: 9
<212> TYPE: PRT
<213> ORGANISM: Homo sapiens
<220> FEATURE:
```

```
<221> NAME/KEY: misc_feature
<222> LOCATION: (1)..(9)
<223> OTHER INFORMATION: SHBG_HUMAN

<400> SEQUENCE: 142

Leu Asp Val Asp Gln Ala Leu Asn Arg
1               5

<210> SEQ ID NO 143
<211> LENGTH: 18
<212> TYPE: PRT
<213> ORGANISM: Homo sapiens
<220> FEATURE:
<221> NAME/KEY: misc_feature
<222> LOCATION: (1)..(18)
<223> OTHER INFORMATION: TSP1_HUMAN

<400> SEQUENCE: 143

Phe Thr Gly Ser Gln Pro Phe Gly Gln Gly Val Glu His Ala Thr Ala
1               5                   10                  15

Asn Lys

<210> SEQ ID NO 144
<211> LENGTH: 9
<212> TYPE: PRT
<213> ORGANISM: Homo sapiens
<220> FEATURE:
<221> NAME/KEY: misc_feature
<222> LOCATION: (1)..(9)
<223> OTHER INFORMATION: Human Carbonic anhydrase 1

<400> SEQUENCE: 144

Gly Gly Pro Phe Ser Asp Ser Tyr Arg
1               5

<210> SEQ ID NO 145
<211> LENGTH: 8
<212> TYPE: PRT
<213> ORGANISM: Homo sapiens
<220> FEATURE:
<221> NAME/KEY: misc_feature
<222> LOCATION: (1)..(8)
<223> OTHER INFORMATION: Human Carbonic anhydrase 1

<400> SEQUENCE: 145

Asn Gly Pro Glu Gln Trp Ser Lys
1               5
```

METHODS OF DETECTING OSTEOARTHRITIS AND PREDICTING PROGRESSION THEREOF

CROSS-REFERENCE TO RELATED APPLICATIONS

This patent application is a national stage filing under 35 U.S.C. 371 of International Application No. PCT/US2016/016736, filed Feb. 5, 2016, which claims the benefit of priority of U.S. Provisional Patent Application No. 62/112,445 filed Feb. 5, 2015, and U.S. Provisional Patent Application No. 62/172,394 filed Jun. 8, 2015, all of which are incorporated herein by reference in their entireties.

SEQUENCE LISTING

A Sequence Listing accompanies this application and is incorporated herein by reference in its entirety. The Sequence Listing was filed with the application as a text file on Feb. 5, 2016.

INTRODUCTION

Osteoarthritis is a prevalent chronic disease that represents a large and growing global health burden of large unmet need with respect to diagnostics, prognostics and therapeutics. Based on data from the Global Burden of Disease 2010 Study, musculoskeletal conditions are the second greatest cause of disability, as measured by years lived with disability (YLDs) worldwide and across most regions of the world; the main contributors are low back pain (83.1 million YLDs), neck pain (33.6 million YLDs) and osteoarthritis (17.1 million YLDs) with osteoarthritis of the knee accounting for 83% of this total. Globally, osteoarthritis of the knee affects 251 million individuals, and back and neck pain (likely largely also attributable to osteoarthritis) currently affect 964 million people worldwide. In the US, according to the Centers for Disease Control, osteoarthritis affects an estimated 26.9 million US adults (estimates from 2005, up 28% from the estimated 21 million US adults impacted in 1990). As the US population continues to age and struggle with obesity, the incidence and prevalence of the disease is expected to continue to grow. Consequently, the annual cost of osteoarthritis to the US, estimated to be $89.1 billion in 2001, is anticipated to continue to grow.

Demographics and baseline characteristics are poor predictors of OA progression including age, sex, body mass index, knee pain, general bone mineral content, and joint space width at baseline. In a systematic literature review, it was noted that 25-75% of painful knees cannot be diagnosed as OA by x-ray. Bedson J and Croft P R, *BMC Musculoskelet Disord* 9:116 (2008). Moreover, knee pain has been reported to have only a 23% sensitivity and 88% specificity for the diagnosis of radiographic OA. Hart et al., Ann Rheum Dis 50(7):467-70 (1991). Bedson et al concluded that, "The results of knee x-rays should not be used in isolation when assessing individual patients with knee pain." Bedson J and Croft P R, *BMC Musculoskelet Disord* 9:116 (2008). Our goal was to develop a better means of diagnosing and predicting progression of knee osteoarthritis.

SUMMARY

Methods of diagnosis and predicting progression of osteoarthritis, and in particular knee osteoarthritis, are provided herein. In one aspect, methods of diagnosing osteoarthritis by measuring biomarkers are provided. The methods include measuring the level of a biomarker in a sample from the subject. The biomarker may be at least one biomarker selected from the group consisting of CRAC1 (CRTAC1), A2AP, A1BG, A2GL, AACT, ACTG, AMBP, APOB, APOE, B2MG, C1QC, C1R, C1RL, C4BPA, C4BPB, CD14, CD44, CERU, CFAB, CFAH, CFAI, CILP1, C1S, CNDP1, CO2, CO4B, CO5, CO6A3, CO8B, CO8G, CO9, coll3, COMP, CTX1a, CTX1b, CTX2, CTXi, CXCL7, ECM1, FA12, FA5, FBLN1, FBLN3, FCGBP, FCN3, FETUA, FINC, GELS, HA, HABP2, haptoglobin, HEMO, HEP2, HGFA, HRG, hyaluronan, IC1, ITIH1, ITIH4, KNG1, LAMA2, LUM, LYAM1, MASP1, PCOC1, PGCA, PHLD, PLF4, PLMN, PRG4, RET4, SAMP, SHBG, TENX, TETN, THBG, TIMP1, TSP1, TSP4, VTDB, VTNC, ZA2G, ZPI, or any combination thereof. The levels of the biomarker in the subject are then compared to the levels of the biomarker in a control subject or a reference level of the biomarker. The subject can then be diagnosed with osteoarthritis if the expression of any of the biomarkers is altered as compared to the reference level.

In another aspect, methods of predicting progression of osteoarthritis by measuring the expression levels of biomarkers in a sample from a subject are also provided. The biomarker may be at least one biomarker selected from the group consisting of A1BG, A2AP, A2GL, AACT, ACTG, AFAM, ANT3, APOB, APOH, B2MG, C1QC, C1R, C1RL, C4BPA, C4BPB, CD14, CD163, CD44, CERU, CFAB, CFAH, CFAI, C1S, CO2, CO4B, CO5, CO6A3, CO8B, coll3, CRAC1 (CRTAC1), CTX2, CXCL7, DOPO, ECM1, FA5, FA12, FBLN1, FCGBP, FCN3, FETUA, FINC, GELS, HABP2, haptoglobin, HEMO, HEP2, HGFA, HRG, hyaluronan, ITIH4, KLKB1, KNG1, LUM, LYAM1, PGCA, PHLD, PLF4, PLMN, PRG4, RET4, SAMP, TENX, TETN, THBG, THRB, TIMP1, TSP1, TSP4, VTDB, VTNC, or combinations thereof. The level of the biomarker in the sample is compared to a reference level of the biomarker. The comparison is then used to predict the progression of the osteoarthritis. A significant alteration in the level of any of the biomarkers as compared to the reference level is predictive of progression of osteoarthritis or indicative of risk of osteoarthritis progression.

DETAILED DESCRIPTION

Figure 1:
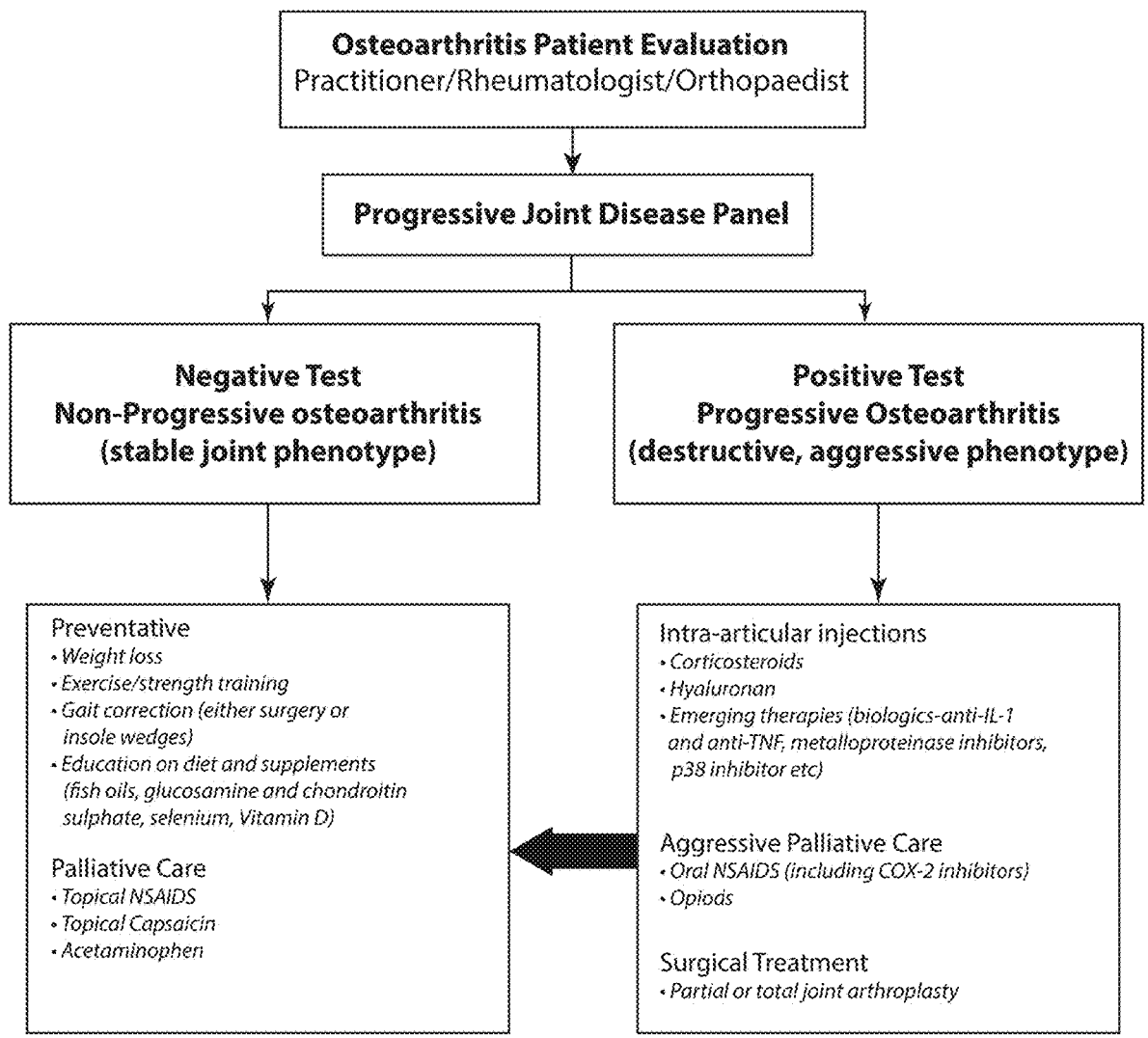
FIG. 1 is a flow chart showing how the biomarkers could be used to assist in diagnosing and predicting the progression of knee osteoarthritis and how this would be translated into a treatment plan.

Methods of diagnosing or predicting progression of osteoarthritis in a subject are provided. The methods all rely on detecting or determining the level of at least one biomarker or combinations of biomarkers in a sample from a subject. In some cases, the subject has knee pain or has already been diagnosed with knee osteoarthritis. The subject may also be diagnosed with, or suspected of having osteoarthritis in another joint other than the knee, such as the hip, back, hand, elbow, shoulder, neck or other joint in the subject. Suitably, the subject is a human, but subjects may include other non-human mammals such as domesticated animals.

Thus, the present methods permit the diagnosis and personalization of therapy or a treatment plan, wherein a subject's biomarker profile is predictive of, or indicative of, a diagnosis of osteoarthritis or risk of progression of osteoarthritis. The methods disclosed herein related to osteoarthritis can be used in combination with assessment of conventional clinical factors or measures, such as age, sex, body mass index or radiographic parameters; this is analogous to the practice for diagnosis or prognosis of rheumatoid arthritis by measuring rheumatoid factor and/or anti-cyclic citrullinated peptide and considering them in conjunction with morning stiffness, joint swelling and/or radiographic features of joint disease, etc. In this manner, the methods of the present disclosure permit a more accurate evaluation of osteoarthritis both at the level of diagnosis and of prognosis of progression of the disease.

In some embodiments, the method includes determining the levels of the biomarkers provided herein in Table 2a in a sample from a subject diagnosed with or suspected of having osteoarthritis. Biomarker levels in some instances may be normalized against the levels of all proteins in the sample, or against a reference or normalization protein(s) in the sample as discussed and exemplified in the Examples. The following set of peptides may be used as normalization peptides in the methods provided herein: TSP1, CNDP1, FA5, SHBG, PLF4, C1QC, ADIPO, APOA4, ACTG, CD14, K2C1, CBG, CHLE, FA11 or any combinations thereof. The level of the biomarkers is indicative of the prognosis for the progression of osteoarthritis in the subject or may be used for the diagnosis of osteoarthritis and may be used to develop a treatment plan or determine the effectiveness of a particular treatment.

In some embodiments, the methods disclosed herein further comprise measuring the level of at least one normalization peptide from a protein selected from TSP1, CNDP1, FA5, SHBG, PLF4, C1QC, ADIPO, APOA4, ACTG, CD14, K2C1, CBG, CHLE, FA11 or any combination thereof in a sample from a subject and normalizing the level of the biomarker in the sample from the subject and the reference level of the biomarker to the level of the normalization peptide in the sample and the reference prior to comparing the level of the biomarker in the sample to the reference level of the biomarker. In some embodiments, the normalization peptide comprises at least one of the sequences of Tables 12 or 13.

The early stages of osteoarthritis are characterized by pain in the affected joint and changes to the cartilage that lines the ends of the bones and cushions the joints. The changes may include thinning of the cartilage layer. Usually the pain in the early stages is well-managed with rest and topical or non-prescription ingestible anti-inflammatory pharmaceutical agents. Moderate osteoarthritis often involves pain with standing as well as when moving and may show bone thickening along joint margins. Treatment involves increased use of anti-inflammatory and anti-pain medications including NSAIDS and steroids. Progression to later stages may restrict the ability of the affected subject to move and to work and may require treatment with stronger pain medications such as opioids, injectable corticosteroids, lubrication injections, physical therapy and joint replacement surgery. Identifying patients likely to progress to a more severe form of the disease would aid medical professionals in determining the appropriate treatment options for individuals with osteoarthritis earlier in the disease course, before disability occurs and when the disease is more likely to be favorably impacted by treatment.

The methods of the present disclosure can also be used to assist in selecting appropriate courses of treatment and to identify patients that would benefit from a particular course of therapy. As shown in FIG. 1, if a subject is demonstrated, via evaluation of the biomarkers provided herein, to be likely to have non-progressive disease then the treatment plan on the left can be pursued which is non-invasive and includes non-pharmacologic therapy. If instead the subject is determined to be likely to have progressive osteoarthritis, then more aggressive treatment options can be pursued including injections or treatment with pharmaceuticals and surgery. Thus, the levels of the particular biomarkers described herein provide insight into which treatment regimens will be most effective for the subject. This information can be used to generate treatment plans for the subject to prolong an active, pain-free lifestyle and minimize side effects, adverse reactions or therapy related toxicity. Methods of developing a treatment plan for a subject with osteoarthritis are also provided herein. Treatment plans may be developed as shown in FIG. 1 using the predictions of the likelihood of progression of osteoarthritis. Methods of monitoring a treatment plan are also provided. The methods may be performed on a recurring basis in order to determine whether a particular treatment plan is effective in reducing and maintaining reduction of at least one symptom of osteoarthritis.

In some embodiments, the methods of the present disclosure may further include administering an anti-inflammatory or anti-pain therapeutic to the subject if the subject is diagnosed with osteoarthritis or predicted to have non-progressive or progressive disease. Suitable anti-inflammatory therapeutics are known to those skilled in the art and may include, without limitation, nonsteroidal anti-inflammatory drugs (NSAIDs), disease-modifying osteoarthritis drugs (DMOADs), disease-modifying antirheumatic drugs (DMARDs), corticosteroids, and hyaluronans. Several classes of DMARDs may be used in accordance with the present invention including, but not limited to, traditional DMARDs such as methotrexate, hydroxycholorquine, sulfasalazine, leflunomide, cyclophosphamide and azathioprine; biologics such as anti-IL-1 therapeutics, anti-TNF therapeutics, metalloproteinase inhibitors, p38 inhibitors, abatacept, adalimumab, anakinra, certolizumab pegol, etanercept, infliximab, golimumab and rituximab; and JAK inhibitors such as Tofacitinib. Suitable anti-pain therapeutics include, without limitation, non-opioid analgesics (e.g., acetaminophen), nonsteroidal anti-inflammatory drugs (NSAIDs), opioid analgesics, and co-analgesics and most likely in future, nerve growth factor inhibitors. Subjects having stable or non-progressive disease may be treated with topical or ingestible pain or anti-inflammatory medications. Subjects identified as having progressive destructive or aggressive disease likely to lead to joint destruction may be referred for injectable lubricant or biologic agent procedures, stronger pain medications such as opioids, bone-acting agents such as calcitonin, bisphosphonates and hormonal therapies, physical therapy, arthroscopic surgery, osteotomy, fibulectomy or joint replacement surgery.

Methods of treating osteoarthritis in a subject are provided. The methods of treating osteoarthritis may include administering a therapeutically effective amount of an anti-inflammatory or anti-pain therapeutic to the subject provided that the levels of at least one of the biomarkers listed in Table 2A in a sample from the subject was determined to be modified (increased or decreased) as compared to the reference level as shown in Table 2A or greater than/less than the threshold values reported in Table 2A, 2C or 2D to diagnose osteoarthritis or indicate the subject's disease is likely to progress.

In some embodiments, the age, gender and/or body mass index of the subject are also used in making the prediction of progression or diagnosis. In some embodiments described herein, diagnostic and prognostic performance of the biomarkers and/or other clinical parameters such as demographics including sex, age, BMI and cohort were assessed utilizing logistic regression to compute p-values and confidence intervals. These statistics were then used to calculate a Benjamini-Hochberg FDR threshold. A biomarker was considered a significant biomarker if the FDR passed 10%. Knee-level analysis required a paired evaluation and the generalized estimating equation method was used to account for the correlation structure and the significance of the biomarker was assessed by a Wald statistic. The statistical analysis used is described in the Examples section. Methods for assessing statistical significance are well known in the art and thus other methods may be used. In some aspects of the invention, a p-value of less than 0.05 constitutes statistical significance.

As used herein, the term "subject" and "patient" are used interchangeably and refer to both human and non-human animals. The term "non-human animals" as used in the disclosure includes all vertebrates, e.g., mammals and non-mammals, such as non-human primates, sheep, dog, cat, horse, cow, chickens, rodents, guinea pigs, amphibians, reptiles, and the like. Preferably and in some embodiments, the subject is a human patient. The subject may be a human patient with knee pain or already diagnosed with or suspected of having osteoarthritis.

The biomarkers of the present disclosure include proteins and genes encoding the proteins. The biomarkers analyzed are provided in Table 2B along with an indication of the commonly used abbreviations for each marker. Such biomarkers include the entire protein or peptide portions of the protein. As shown in the Examples, peptides from each of these proteins were identified as useful in the methods provided herein. The biomarker peptides used in the examples are shown in Table 2A. These biomarkers may be used alone in the methods or in combinations as described below.

Fragments and genetic variants of biomarkers are also encompassed by the present invention. "Fragment" is intended to include a portion of the amino acid sequence and hence a portion of the protein encoded thereby. A fragment or a biomarker peptide will generally encode at least 7, 8, 9, 10, 12, 15, 17, 20, 22, 25, 30 or more contiguous amino acids, or up to the total number of amino acids present in a full-length biomarker. "Variant" is intended to mean substantially similar sequences. Generally, variants of a particular biomarker of the invention will have at least about 80%, 85%, 90%, 91%, 92%, 93%, 94%, 95%, 96%, 97%, 98%, 99% or more amino acid identity to that biomarker as determined by amino acid alignment programs.

A "biomarker" is a protein or glycan whose level in a sample is altered compared to that of a normal or healthy sample or is indicative of a condition. The biomarkers disclosed herein are proteins or glycans whose levels correlate with osteoarthritis and can be used to predict the progression of the disease as well as diagnose the disease.

In particular embodiments, the methods for predicting progression of or diagnosing osteoarthritis in a subject include collecting a patient body sample. The sample may or may not include cells. In particular, the methods described herein may be performed without requiring a tissue sample or biopsy. "Sample" is intended to include any sampling of cells, tissues, or bodily fluids in which a level of a biomarker can be detected. Examples of such samples include, but are not limited to, blood, serum, urine, synovial fluid, saliva, or any other bodily secretion or derivative thereof. Blood can include whole blood, plasma (citrate, EDTA, heparin), serum, or any derivative of blood. Samples may be obtained from a patient by a variety of techniques available to those skilled in the art. Methods for collecting various samples are well known in the art. In some embodiments, the sample is serum, plasma, urine, or synovial fluid. In some embodiments, the sample is serum depleted of at least 7 major serum proteins. In some embodiments, the serum proteins depleted are selected from the group consisting of albumin, IgG, IgA, transferrin, haptoglobin, anti-trypsin, fibrinogen, alpha 2-macroglobulin, IgM, apolipoprotein AI, apolipoprotein AII, complement C3, and transthyretin.

Any methods available in the art for detecting the level of biomarkers are encompassed herein. The level of a biomarker of the invention can be detected using a peptide corresponding to the biomarker. "Measuring an expression level of" is intended to mean determining the quantity or presence of a biomarker (i.e., peptide) in a sample for at least one of the biomarkers of Table 2a. Thus, "measuring an expression level of" encompasses instances where a biomarker is determined not to be detectable due to failure to be produced, or due to production below the detection limit of the assay; "measuring an expression level of" also encompasses low, normal and high levels of detection. Measuring an expression level also includes instances where a marker is degraded or is more stable in a person with osteoarthritis or with progressive disease and is not limited to production of new peptide or the timing of peptide production.

Methods suitable for "measuring an expression level of" biomarkers are known to those of skill in the art and include, but are not limited to, ELISA, immunofluorescence, FACS analysis, Western blot, magnetic immunoassays, mass spectroscopy, gel electrophoresis, antibody-based microarrays and non-antibody-based microarrays or combinations of these methods. In the past, the gold standard for detection of growth factors and cytokines in blood was the use of ELISAs; however, multiplex technology and mass spectroscopy offer attractive alternative approaches for protein-based analyses. The advantages of multiplex technology compared to traditional ELISA assays are conservation of patient sample, and significant savings in cost, time and labor. In some embodiments, the biomarker is measured using an antibody-based capture method. In some embodiments, the biomarker is measured using mass spectrometry.

Several multiplex platforms currently exist. The Luminex bead-based systems are the most established, being used to detect circulating cytokines and growth factors in both mice and humans. This method is based on the use of microparticles that have been pre-coated with specific antibodies. These particles are then mixed with sample and the captured analytes are detected using specific secondary antibodies. This allows for up to 100 different analytes to be measured simultaneously in a single microplate well. The advantages of this flow cytometry-based method compared to traditional ELISA assays are in the conservation of patient samples as well as significant savings in terms of cost and labor. An alternative, plate-based system is produced by Meso Scale Discovery (MSD). This system utilizes its proprietary Multi-Array® and Multi-Spot® microplates with electrodes directly integrated into the plates. This enables the MSD system to have ultra-sensitive detection limits, high specificity, large dynamic range, and low background signal. Another plate-based multiplex system is the SearchLight Plus CCD Imaging System produced by Aushon Biosystems. This novel multiplexing technology allows for the measurement of up to 16 different analytes simultaneously in a single microplate well. The assay design is similar to a sandwich ELISA where the capture antibodies are pre-spotted into individual wells of a 96-well plate. Samples or standards are added which bind to the specific capture antibodies and are detected using Aushon's patented Super-Signal ELISA Femto Chemiluminescent Substrate. Still another method is SomaLogic which is a bead-based technology for multiplex quantification of proteins or protein fragments.

The term "probe" refers to any molecule that is capable of selectively binding to a specifically intended target biomolecule, for example, a protein encoded by or corresponding to a biomarker. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules. Detectable labels include, but are not limited to, any heterologous addition to the probe that can be used to detect the selectively bound probe. Examples of detectable labels include fluorescent and radiological labels as well as labels that can be detected because they have a specific binding partner (ligand/receptor interaction) such as biotin/avidin or a nucleic acid tag that may act as a barcode to bind and specifically identify a larger nucleic acid.

As used herein the term "predicting progression" or "a prediction of progression" refers to providing a probability-based analysis of risk for osteoarthritis progression in a particular subject. The prediction of progression of osteoarthritis is not a guarantee or absolute, only a statistically probable indication of the disease state of the subject. The term prediction of a "diagnosis" or "diagnosing" of osteoarthritis refers to providing a probability-based analysis of an osteoarthritis diagnosis in a particular subject. The prediction of a diagnosis of osteoarthritis is not a guarantee or absolute, only a statistically probable indication of the disease state of the subject.

The level of the biomarker in the sample from the subject is compared to a reference level of the biomarker. The reference level may be determined empirically such as illustrated in the Examples, by comparison to the levels found in a set of samples from subjects with known clinical outcomes or known to have or not have osteoarthritis. Alternatively, the reference level may be a level of the biomarker found in samples, such as serum samples, which becomes a standard and can be used as a predictor for new samples. The level of the biomarker in the sample from the subject may be increased or decreased (i.e., "altered") as compared to the reference level. The Examples and Tables provide information regarding how each biomarker is altered to indicate a diagnosis or to predict progression.

The predictive methods described herein may be combined to provide increased significance of the results, i.e. increased AUCs. For example, the levels of multiple markers may be determined in a sample from the subject and the results may have additional statistical or predictive power via the combination. The levels may be compared to the reference levels and a diagnosis or a prediction of risk of progression made. Several exemplary combinations are provided below and in the Examples, but any combination of 2, 3, 4, 5, 6, 7, 8, 9, 10 or more of the biomarkers may provide a prediction with increased accuracy and thus be beneficial.

Diagnosis

In some embodiments, the invention relates to a method of diagnosing osteoarthritis comprising measuring an expression level of at least one biomarker selected from the group consisting of CRAC1 (CRTAC1), A2AP, A1BG, A2GL, AACT, ACTG, AMBP, APOB, APOE, B2MG, C1QC, C1R, C1RL, C4BPA, C4BPB, CD14, CD44, CERU, CFAB, CFAH, CFAI, CILP1, C1S, CNDP1, CO2, CO4B, CO5, CO6A3, CO8B, CO8G, CO9, coll3, COMP, CTX1a, CTX1b, CTX2, CTXi, CXCL7, ECM1, FA12, FA5, FBLN1, FBLN3, FCGBP, FCN3, FETUA, FINC, GELS, HA, HABP2, haptoglobin, HEMO, HEP2, HGFA, HRG, hyaluronan, IC1, ITIH1, ITIH4, KNG1, LAMA2, LUM, LYAM1, MASP1, PCOC1, PGCA, PHLD, PLF4, PLMN, PRG4, RET4, SAMP, SHBG, TENX, TETN, THBG, TIMP1, TSP1, TSP4, VTDB, VTNC, ZA2G, ZPI, or any combination thereof in a sample from a subject; comparing the level of at least one biomarker in the sample to a reference level of the biomarker; and diagnosing the subject with osteoarthritis if the level of at least one biomarker is altered as compared to the reference level. In some embodiments, such methods further comprise developing a treatment plan for the subject if the subject is diagnosed with osteoarthritis.

In some embodiments, the biomarker is a combination of at least two of CRAC1, COMP, CO6A3, SHBG, PCOC1, CO8G, LUM, ACTG, CO5, A2AP, CO2, FA5, CERU, KNG1, HPLN1, CD14, CERU, CTX1a, CTX1b, VTNC, ZPI and haptoglobin and the diagnosis of osteoarthritis includes the presence of an osteophyte or a bone anabolic response. A combination of all the listed biomarkers or only two, three, four, five, six, seven, eight, nine, ten or more may also be used. In some embodiments, the biomarker is a combination of at least one of CRAC1, CXCL7, C4BPA, COMP, LUM, CO5, TIMP1, C4BPA, PCOC1, A2AP, CO2, FA5, HRG, CO6A3, VTDB, KNG1, HPLN1, CD14, CERU, CTX1a, CTX1b, PLF4, TETN, TSP1, PHLD, C4BPB, CFAI, SAMP, CO8B, ECM1, TSP4, CILP, APOE, IHA, CTX2, CTXi, hyaluronan and haptoglobin and the diagnosis of osteoarthritis includes the presence of worsening joint space narrowing indicative of cartilage or meniscal abnormality. A combination of all the listed biomarkers or only two, three, four, five, six, seven, eight, nine, ten or more may also be used. In some embodiments, the biomarker is a combination of at least one of CRAC1, SHBG, COMP, CO8G, PCOC1, CO6A3, LUM, CO5, A2AP, CO2, FA5, FBLN3, VTDB, KNG1, HPLN1, CD14, CERU, CTX1a, CTX1b, CTX2, CTXi, CFAH, TSP4 and haptoglobin and the diagnosis of osteoarthritis includes the progression of the Kellgren-Lawrence (KL) grade where progression is defined by a joint KL grade/score increasing to indicate a higher, i.e. worse, grade. A combination of all the listed biomarkers or only two, three, four, five, six, seven, eight, nine, ten or more may also be used. In some embodiments, the biomarker includes CRAC1, KNG1 and/or haptoglobin for diagnosis of osteoarthritis.

In some embodiments, the biomarkers measured comprise at least two biomarkers selected from the group consisting of CRAC1 (CRTAC1), CXCL7, CO8G, ACTG, CD44, CERU, CFAH, CFAI, CO6A3, CO8G, COMP, FINC, HRG, KNG1, PLF4, PRG4, SAMP, TSP4, and any combination thereof. A combination of all the listed biomarkers or only two, three, four, five, six, seven, eight, nine, ten or more may also be used. In some embodiments, the biomarkers measured comprise CRAC1 (CRTAC1) and CXCL7. In some embodiments, the biomarkers measured comprise CXCL7 and CO8G. In some embodiments, the biomarkers measured comprise CO8G and CRAC1. In still further embodiments, the biomarkers measured comprise CRAC1 (CRTAC1), CXCL7, and CO8G.

In some embodiments, the biomarkers measured comprise at least two biomarkers selected from the group consisting of CRAC1 (CRTAC1), A2AP, ACTG, APOE, C1QC, C4BPB, CD14, CFAI, CO5, CO6A3, CO8G, col13, CXCL7, FA5, FCGBP, FINC, GELS, HA, HEMO, KNG1, PCOC1, TENX, VTDB, or any combination thereof. In some embodiments, the biomarkers measured comprise at least two biomarkers selected from the group consisting of CRAC1 (CRTAC1), A2AP, ACTG, APOE, C1QC, C4BPB, CFAI, CO5, CO6A3, CO8G, CXCL7, FA5, FCGBP, FINC, GELS, PCOC1, TENX, or any combination thereof. In some embodiments, the biomarkers measured comprise CRAC1 (CRTAC1), A2AP, ACTG, APOE, C1QC, C4BPB, CFAI, CO5, CO6A3, CO8G, CXCL7, FA5, FCGBP, FINC, GELS, PCOC1, and TENX. In some embodiments, the biomarkers measured comprise at least two biomarkers selected from the group consisting of CD14, col13, HA, HEMO, KNG1, VTDB or any combination thereof. In some embodiments, the biomarkers measured comprise at least two biomarkers selected from the group consisting of CRAC1 (CRTAC1), COMP, CO6A3, CO8G, CXCL7, or any combination thereof. In some embodiments, the biomarkers measured comprise CRAC1 (CRTAC1), COMP, CO6A3, CO8G, and CXCL7.

In some embodiments, the biomarkers measured comprise at least two biomarkers selected from the group consisting of CRAC1 (CRTAC1), CXCL7, C4BPA, COMP, LUM, CO5, TIMP1, or any combination thereof. In some embodiments, the biomarkers measured comprise CRAC1 (CRTAC1) and CXCL7. In further such embodiments, the biomarkers measured further comprise C4BPA and/or COMP. In still further such embodiments, the biomarkers measured further comprise LUM, CO5, and/or TIMP1.

In some embodiments, the biomarkers measured comprise at least two biomarkers selected from the group consisting of CRAC1 (CRTAC1), SHBG, COMP, CO8G, PCOC1, CO6A3, LUM, or any combination thereof. In some embodiments, the biomarkers measured comprise CRAC1 (CRTAC1) and SHBG. In further such embodiments, the biomarkers measured further comprise COMP and/or CO8G. In still further such embodiments, the biomarkers measured further comprise PCOC1, CO6A3, and/or LUM. In some embodiments, the biomarkers measured comprise CRAC1 (CRTAC1) and COMP. In further such embodiments, the biomarkers measured further comprise CO6A3 and/or SHBG.

In some embodiments, the biomarkers measured comprise at least two biomarkers selected from the group consisting of CRAC1 (CRTAC1), C4BPA, LUM, CO5, PCOC1, CXCL7, COMP, or any combination thereof. In some embodiments, the biomarkers measured comprise CRAC1 (CRTAC1) and CXCL7. In further such embodiments, the biomarkers measured further comprise C4BPA and/or LUM. In still further such embodiments, the biomarkers measured further comprise CO5, PCOC1, and/or COMP.

In some embodiments, the biomarkers measured comprise at least two biomarkers selected from the group consisting of CRAC1 (CRTAC1), PCOC1, CO8G, LUM, COMP, CO6A3, CO5, ACTG or any combination thereof. In some embodiments, the biomarkers measured comprise CRAC1 (CRTAC1) and PCOC1. In further such embodiments, the biomarkers measured further comprise COMP and/or CO8G. In still further such embodiments, the biomarkers measured further comprise LUM, CO6A3, and/or CO5. In some embodiments, the biomarkers measured comprise CRAC1 (CRTAC1) and COMP. In further such embodiments, the biomarkers measured further comprise CO6A3 and/or PCOC1. In still further such embodiments, the biomarkers measured comprise CO8G, ACTG, and/or CO5.

In some embodiments, the biomarkers measured comprise at least two biomarkers selected from the group consisting of A2AP, CO2, COMP, FA5, CO5, CRAC1 (CRTAC1), SHBG, or any combination thereof. In some embodiments, the biomarkers measured comprise A2AP and CO2. In further such embodiments, the biomarkers measured further comprise COMP and/or FA5. In still further such embodiments, the biomarkers measured further comprise CO5, CRAC1 (CRTAC1), and/or SHBG.

In some embodiments, the biomarkers measured comprise at least two biomarkers selected from the group consisting of A2AP, FA5, CO2, CO5, COMP, SHBG, CO6A3, or any combination thereof. In some embodiments, the biomarkers measured comprise A2AP and FA5. In further such embodiments, the biomarkers measured further comprise CO5 and/or CO2. In still further such embodiments, the biomarkers measured further comprise COMP, SHBG, and/or CO6A3. In some embodiments, the biomarkers measured comprise at least two biomarkers selected from the group consisting of A2AP, CRAC1 (CRTAC1), CO2, COMP, FA5, CO5, or any combination thereof. In some embodiments, the biomarkers measured comprise A2AP and CO2. In further such embodiments, the biomarkers measured further comprise COMP and/or CRAC1 (CRTAC1). In some embodiments, the biomarkers measured comprise A2AP, CRAC1 (CRTAC1), and CO2. In further such embodiments, the biomarkers measured further comprise FA5. In still further such embodiments, the biomarkers measured further comprise COMP and/or CO5.

In some embodiments, the biomarkers measured comprise a peptide sequence listed in Table 2A or 2C. In some embodiments, the subject is diagnosed with osteoarthritis if the level of at least one biomarker is altered as shown in Table 2A or 2C.

Prognosis

In some embodiments, the invention relates to a method of predicting progression of osteoarthritis comprising measuring an expression level of at least one biomarker selected from the group consisting of A1BG, A2AP, A2GL, AACT, ACTG, AFAM, ANT3, APOB, APOH, B2MG, C1QC, C1R, C1RL, C4BPA, C4BPB, CD14, CD163, CD44, CERU, CFAB, CFAH, CFAI, C1S, CO2, CO4B, CO5, CO6A3, CO8B, col13, CRAC1 (CRTAC1), CTX2, CXCL7, DOPO, ECM1, FA5, FA12, FBLN1, FCGBP, FCN3, FETUA, FINC, GELS, HABP2, haptoglobin, HEMO, HEP2, HGFA, HRG, hyaluronan, ITIH4, KLKB1, KNG1, LUM, LYAM1, PGCA, PHLD, PLF4, PLMN, PRG4, RET4, SAMP, TENX, TETN, THBG, THRB, TIMP1, TSP1, TSP4, VTDB, VTNC, or combinations thereof in a sample from a subject; comparing the level of the biomarker in the sample to a reference level of the biomarker; and predicting the progression of the osteoarthritis, wherein altered levels of any of the biomarkers as compared to the reference level is indicative of progression of the osteoarthritis. In some embodiments, such methods further comprise developing a treatment plan for the subject based on the prediction of progression of the osteoarthritis.

In some embodiments, the biomarker is a combination of at least two of PLF4, CXCL7, ANT3, AACT, THRB, ITIH4, CO8B, PLMN, PRG4, C4BPA, C4BPB, A2AP, LYAM1, CO8G, KLKB1, hyaluronan and haptoglobin and the prediction of osteoarthritis progression includes osteophyte growth or a bone anabolic response. A combination of all the listed biomarkers or only two, three, four, five, six, seven, eight, nine, ten or more may also be used. In some embodiments, the biomarker is a combination of at least two of PGCA, APOH, SAMP, AACT, CFAH, PHLD, TSP1, THRB, HRG, CO4B, FCN3, CD44, TSP4, TETN, FINC, ECM1, HEMO, CD163, CERU, TIMP1, A1BG, THBG, A2GL, FBLN1, CO5, B2MG, FETUA and haptoglobin and the prediction of osteoarthritis progression includes worsening joint space narrowing. A combination of all the listed biomarkers or only two, three, four, five, six, seven, eight, nine, ten or more may also be used. In some embodiments, the biomarker is a combination of at least one of CFAH, SAMP, TSP1, HEP2, C1R, APOB, FINC, PGCA, AACT, KNG1, A2AP, CO6A3, HGFA, CO2, PRG4, DOPO, CD44, CERU, VTDB, and haptoglobin and the prediction of osteoarthritis progression includes progression by the Kellgren-Lawrence (KL) grading scale (progression is defined as joint KL score increasing to a higher or worse grade). A combination of all the listed biomarkers or only two, three, four, five, six, seven, eight, nine, ten or more may also be used. In some embodiments, the biomarkers include CO8B, haptoglobin and/or PLF4 and the prediction relates to the progression of osteoarthritis.

In some embodiments, the biomarkers measured comprise at least two biomarkers selected from the group consisting of ACTG, ANT3, CD44, CERU, CFAH, CFAI, CO8B, CXCL7, CO6A3, CRAC1 (CRTAC1), FINC, haptoglobin, HRG, KLKB1, PLF4, PRG4, SAMP, TSP4 and any combination thereof. A combination of all the listed biomarkers or only two, three, four, five, six, seven, eight, nine, ten or more may also be used. In some embodiments, the biomarkers measured comprise at least two biomarkers selected from the group consisting of PLF4, CFAH, and ANT3. In still further embodiments, the biomarkers measured comprise PLF4, CFAH, and ANT3. In some embodiments, the biomarkers measured comprise at least two biomarkers selected from the group consisting of ANT3, CD14, CD163, CD44, CERU, CFAH, CO8B, coll3, CRAC1 (CRTAC1), CTX2, CXCL7, haptoglobin, HEMO, HRG, KLKB1, LYAM1, VTDB, or any combination thereof. In some embodiments, the biomarkers measured comprise at least two biomarkers selected from the group consisting of ANT3, CFAH, CO8B, CRAC1 (CRTAC1), CXCL7, HRG, KLKB1, LYAM1, or any combination thereof. In some embodiments, the biomarkers measured comprise at least two biomarkers selected from the group consisting of CFAH, CO8B, CRAC1 (CRTAC1), HRG, or any combination thereof. In some embodiments, the biomarkers measured comprise CFAH, CO8B, CRAC1 (CRTAC1), and HRG. In some embodiments, the biomarkers measured comprise at least two biomarkers selected from the group consisting of ANT3, CO8B, CXCL7, KLKB1, LYAM1, or any combination thereof. In some embodiments, the biomarkers measured comprise ANT3, CO8B, CXCL7, KLKB1, and LYAM1. In some embodiments, the biomarkers measured comprise at least two biomarkers selected from CD14, CD163, CD44, CERU, coll3, CTX2, haptoglobin, HEMO, VTDB or any combination thereof. In some embodiments, the biomarkers measured comprise at least two biomarkers selected from the group consisting of ACTG, ANT3, CD44, CERU, CFAH, CFAI, CO8B, FINC, HRG, KLKB1, PLF4, PRG4, SAMP, TSP4 or any combination thereof. In some embodiments, the biomarkers measured comprise ACTG, ANT3, CD44, CERU, CFAH, CFAI, CO8B, FINC, HRG, KLKB1, PLF4, PRG4, SAMP, and TSP4.

In some embodiments, the biomarkers measured comprise at least two biomarkers selected from the group consisting of ANT3, CERU, CFAH, CO8B, FINC, HRG, PLF4, PRG4, SAMP, TSP4 or any combination thereof. In some embodiments, the biomarkers measured comprise ANT3, CERU, CFAH, CO8B, FINC, HRG, PLF4, PRG4, SAMP, and TSP4. In some embodiments, the biomarkers measured comprise at least two biomarkers selected from the group consisting of ACTG, ANT3, CD44, CFAI, CO8B, KLKB1, PLF4, or any combination thereof. In some embodiments, the biomarkers measured further comprise ACTG, ANT3, CD44, CFAI, CO8B, KLKB1, and PLF4.

In some embodiments, the biomarkers measured comprise at least two biomarkers selected from the group consisting of PGCA, APOH, SAMP, AACT, CFAH, PHLD, TSP1, THRB, or any combination thereof. In some embodiments, the biomarkers measured comprise SAMP and AACT. In further such embodiments, the biomarkers measured further comprise PGCA and/or APOH. In still further such embodiments, the biomarkers measured further comprise CFAH, PHLD, TSP1, and/or THRB. The prognosis includes joint space narrowing.

In some embodiments, the biomarkers measured comprise at least two biomarkers selected from the group consisting of CFAH, SAMP, TSP1, HEP2, C1R, APOB, FINC, HEP2, PGCA, or any combination thereof. In some embodiments, the biomarkers measured comprise CFAH and SAMP. In further such embodiments, the biomarkers measured further comprise TSP1 and/or APOB. In still further such embodiments, the biomarkers measured further comprise HEP2, C1R, FINC, HEP2, and/or PGCA. The prediction includes KL grade.

In some embodiments, the biomarkers measured comprise at least two biomarkers selected from the group consisting of PLF4, CXCL7, ANT3, AACT, THRB, ITIH4, CO8B, PLMN, or any combination thereof. In some embodiments, the biomarkers measured comprise PLF4 and AACT. In further such embodiments, the biomarkers measured further comprise CXCL7 and/or ANT3. In still further such embodiments, the biomarkers measured further comprise THRB, ITIH4, CO8B, and/or PLMN. The prediction includes osteophyte growth.

In some embodiments, the biomarkers measured comprise at least two biomarkers selected from the group consisting of TSP1, CFAH, THRB, HRG, APOH, AACT, PHLD, AACT, or any combination thereof. In some embodiments, the biomarkers measured comprise TSP1 and CFAH. In further such embodiments, the biomarkers measured further comprise THRB and/or APOH. In still further such embodiments, the biomarkers measured further comprise HRG, AACT, PHLD, and/or AACT. The prediction includes joint space narrowing.

In some embodiments, the biomarkers measured comprise at least two biomarkers selected from the group consisting of CFAH, TSP1, SAMP, APOB, AACT, C1R, or any combination thereof. In some embodiments, the biomarkers measured comprise CFAH and SAMP. In further such embodiments, the biomarkers measured further comprise TSP1 and/or AACT. In still further such embodiments, the biomarkers measured further comprise APOB and/or C1R. The prediction includes the KL grade.

In some embodiments, the biomarkers measured comprise at least two biomarkers selected from the group consisting of CO8B, PLF4, PRG4, ANT3, C4BPA, CXCL7, C4BPA, or any combination thereof. In some embodiments, the biomarkers measured comprise CO8B and PLF4. In further such embodiments, the biomarkers measured further comprise PRG4 and/or ANT3. In still further such embodiments, the biomarkers measured further comprise C4BPA, CXCL7, and/or C4BPA. The prediction may include osteophyte growth.

In some embodiments, the biomarkers measured comprise at least two biomarkers selected from the group consisting of CO4B, FCN3, CO8B, FINC, PGCA, TSP4, TETN, or any combination thereof. In some embodiments, the biomarkers measured comprise CO8B and CO4B. In further such embodiments, the biomarkers measured further comprise FINC and/or FCN3. In still further such embodiments, the biomarkers measured further comprise PGCA, TSP4, and/or TETN. The prognosis may include joint space narrowing.

In some embodiments, the biomarkers measured comprise at least two biomarkers selected from the group consisting of A2AP, KNG1, HGFA, PRG4, AFAM, DOPO, FINC, CO8B, or any combination thereof. In some embodiments, the biomarkers measured comprise KNG1 and HGFA. In further such embodiments, the biomarkers measured further comprise A2AP and/or CO8B. In still further such embodiments, the biomarkers measured further comprise PRG4, AFAM, DOPO, and/or FINC. The prediction includes a KL grade determination.

In some embodiments, the biomarkers measured comprise at least two biomarkers selected from the group consisting of CXCL7, C4BPA, C4BPB, A2AP, ITIH4, PLMN, HRG, or any combination thereof. In some embodiments, the biomarkers measured comprise CXCL7 and C4BPA. In further such embodiments, the biomarkers measured further comprise C4BPB and/or A2AP. In still further such embodiments, the biomarkers measured further comprise ITIH4, PLMN, and/or HRG. The prediction includes osteophyte growth.

In some embodiments, the biomarkers measured comprise at least two biomarkers selected from the group consisting of PGCA, CO4B, TENX, FCN3, C4BPA, TSP1, CO8B, HRG, or any combination thereof. In some embodiments, the biomarkers measured comprise CO4B and PGCA. In further such embodiments, the biomarkers measured further comprise TENX and/or C4BPA. In still further such embodiments, the biomarkers measured further comprise FCN3, TSP1, CO8B, and/or HRG. The prognosis may include joint space narrowing.

In some embodiments, the biomarkers measured comprise at least two biomarkers selected from the group consisting of KNG1, HGFA, A2AP, FA5, TSP1, PGCA, TENX, FINC, or any combination thereof. In some embodiments, the biomarkers measured comprise KNG1 and HGFA. In further such embodiments, the biomarkers measured further comprise A2AP and/or PGCA. In still further such embodiments, the biomarkers measured further comprise FA5, TSP1, TENX, and/or FINC. The prediction includes KL grade prediction.

In some embodiments, the biomarkers measured comprise at least two biomarkers selected from the group consisting of C4BPA, C4BPB, CXCL7, LYAM1, A2AP, TSP1, FINC, or any combination thereof. In some embodiments, the biomarkers measured comprise C4BPA and CXCL7. In further such embodiments, the biomarkers measured further comprise C4BPB and/or LYAM1. In still further such embodiments, the biomarkers measured further comprise A2AP, TSP1, and/or FINC. The prediction includes osteophyte growth.

In some embodiments, the biomarkers measured comprise a peptide sequence listed in Table 2A, 2C or 2D. In some embodiments, a prediction of progression of the osteoarthritis in the subject is made if the level of at least one biomarker is altered as compared to the reference level as shown in Table 2A or 2D. In some embodiments, a diagnosis of osteoarthritis or a prediction of progression of the osteoarthritis in the subject is made if the level of at least one biomarker is greater or less than the threshold values shown in Table 2A or 2C. In some embodiments, the biomarkers comprise the sequences listed in the Tables included herein. The various embodiments described herein may be combined or used individually.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. As another example, if it is stated that the biomarkers measured comprise "at least one (or any other number)" biomarker selected from a particular group it is intended that values such as "at least two," "at least three," "at least four," etc. (up until the maximum allowed by the statement) are expressly enumerated in the specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

For this project, candidate prognostic and diagnostic biomarkers in non-depleted (normal serum) and depleted serum (serum treated to deplete one or more abundant serum proteins as described more fully below) were evaluated by mass spectrometry. We tested a multiple reaction monitoring (MRM) panel developed on the basis of three discovery proteomics experiments: in synovial fluid, urine and depleted serum. Below we describe the results for a cohort of 124; approximately two-thirds of the subjects were selected on the basis of knee osteoarthritis with either knee OA progression or stability (non-progression) and the remaining one-third of subjects were controls without knee osteoarthritis.

Subjects and Methods
  Cohorts:
  Subjects were selected from two cohorts, the Prediction of Osteoarthritis Progression (POP) cohort, and the Genetics of Generalized Osteoarthritis (GOGO) cohort. Kraus et al., *Ann Rheum Dis* 68(11):1673-9 (2009); Kraus et al., *Osteoarthritis Cartilage* 15(2):120-7 (2007). In brief, POP was a single site study at Duke with 159 subjects recruited on the basis of symptomatic radiographic knee OA of at least one knee; a total of 138 subjects (87%) returned for 3-year follow-up. Knee synovial fluid (from both knees when possible), serum (2 hour post-prandial) and urine (second morning void) were obtained at each evaluation. GOGO was a multi-site (7 sites) study with 2728 subjects recruited on the basis of two siblings with hand OA (defined as 3 joint radiographic KL≥2 grade distributed bilaterally). Knee, hip and spine radiographs were obtained. A total of 1329 subjects from 4 sites returned for follow-up at a mean 3.8 years (range 1.4-6.5 years). Serum (two hour post-prandial) and urine (second morning void or time recorded if other than this) were obtained at each evaluation. The demographics are shown in Table 1 for the patient subsets used for each aspect of biomarker discovery and validation.

Phenotypes
Phenotypes were based on 2 features from knee radiographs (joint space narrowing (JSN) and osteophyte (OST)) evaluated at 2 levels (knee based and person-based). JSN, indicative of cartilage and/or meniscal extrusion loss (cartilage and/or meniscal catabolism), and osteophyte, indicative of bone formation at the margins of the joint (joint tissue anabolism), were graded on a scale 0-3 using a standardized atlas with 0 being normal and 1, 2, and 3 representing increasing severity. Altman R D and Gold G E, *Osteoarthritis Cartilage* 15 Suppl A:A1-56 (2007). The medial and lateral compartments of the knee were graded for JSN (yielding a maximum score of 6 per knee joint); the four margins of the knee were graded for OST (yielding a maximum score of 12 per knee joint). Progression was defined as a one unit change over time in these variables at a knee level or person level. A Diagnosis of OA was defined as any OA represented by a score of greater than or equal to 1 for these variables at a knee level or person level. In addition, a half-century old definition of OA, the Kellgren Lawrence grade, scored on a 0-4 scale, was also evaluated for a one unit change (defining progression) or any OA (defined as KL≥2). Kellgren J H and Lawrence J S, *Ann Rheum Dis* 16(4):494-502 (1957). Controls for each phenotype were defined as a knee or person that did not meet the minimal definition.

TABLE 1

Patient demographics for sample sets used in experiments.

| C = control<br>NP = non-progressor<br>P = progressor | Number for JSN<br>Person knee<br>C/NP/P | Number for OST<br>Person knee<br>C/NP/P | Mean Age,<br>SD (range)<br>years | Gender<br>% female | Mean BMI,<br>SD (range)<br>kg/m² |
|---|---|---|---|---|---|
| SF Proteomics<br>(N = 23) | 1/12/10<br>9/16/21 | 3/5/15<br>9/16/21 | 67 ± 12<br>(43-80) | 74% | 30.4 ± 5.8<br>(23-47) |
| Urine Proteomics<br>(N = 45) | 14/16/15<br>32/36/22 | 16/9/20<br>37/23/30 | 62 ± 12<br>(41 to 81) | 76% | 29.3 ± 6.6<br>(18.6-50.0) |
| Urine ELISA<br>(N = 118) | 47/32/33<br>109/65/52 | 40/24/48<br>94/66/66 | 65 ± 10<br>(41-86) | 59% | 28.7 ± 6.6<br>(18.6-61.7) |
| Serum MRM Validation<br>(N = 40) | 4/16/20<br>13/38/29 | 3/11/26<br>10/30/40 | 63 ± 12<br>(42-80) | 78% | 30.0 ± 6.1<br>(20-50) |
| Serum MRM and ELISA<br>(N = 124) | 50/34/38<br>116/69/61 | 41/37/54<br>98/72/76 | 64 ± 10<br>(41-86) | 82% | 27.6 ± 6.1<br>(18.6-61.7) |

C = control'
NP = non-progressor;
P = progressor;
SF = synovial fluid;
MRM = multiple reaction monitoring Statistical Methods
Two classes of methods were used, inferential methods and predictive methods, depending on the structure of the data. For person-level analysis, logistic regression was used to compute p-values and confidence intervals. Covariates included age, sex, BMI, and cohort. The effect of a biomarker was added to a model containing these covariates and a likelihood-ratio test was used to assess the significance of the biomarker after accounting for the covariates. A biomarker was considered significant if it surpassed a Benjamini-Hochberg FDR threshold of 10%. We defined person level phenotypes as follows: a person-level control as both knees normal; a person level osteoarthritis diagnosis as at least one knee with osteoarthritis; a person level knee osteoarthritis progressor as having at least one knee that has progressive osteoarthritis over time; and a person level non-progressor as having neither knee progressing over time. For a knee-level analysis the dependence arising from paired observations must be considered. We used the generalized estimating equation (GEE) method to account for the correlation structure. A biomarker was added to a model containing base covariates and its significance was assessed by a Wald statistic.

We evaluated the capability of the biomarkers described herein to predict or diagnose osteoarthritis based on its separate features consisting of: cartilage and/or meniscal extrusion or loss (reflected in radiographic joint space narrowing), an anabolic repair response (reflected in radiographic osteophyte presence and growth), and the Kellgren-Lawrence grade of disease (reflecting both osteophyte and joint space narrowing).

Predictive models were used to assess discrimination through the AUC. We used feature selection coupled with ridge regression, a form of penalized regression, for all models implemented in the glmnet R package. Penalized regression is often used for predictive models to constrain the size of coefficients to lessen the effects of overfitting the data. Feature selection consisted of selecting the 8 markers with the lowest p-values, which is a simple but effective method for the numbers of peptides in the current data set. Leave-one-out cross-validation was used in which selecting tuning parameters and carrying out feature selection was repeated at each iteration of cross-validation to mimic the process of fitting a model to new data. In sum, all multi-marker AUCs have been properly cross-validated. For knee-level (paired) analysis, the leave-one-out cross-validation scheme was modified to a leave-sample-out scheme so that the test set was independent of the training set. Of note, an AUC 0.80≈sensitivity and specificity of 75% (depending on clinical context) and odds ratio 9-10. Qoronfleh et al., *Drug Discovery World Winter:*19-28 (2011).

The mean and SD values of ELISA results are natural log values for two of the serum markers that had skewed distributions (Hyaluronan and Ceruloplasmin), and all the urine biomarkers. None of the other serum markers were log transformed. Some values are negative because they are natural log transformations of values less than 1. In particular, all of the urine values were normalized prior to the analysis. Two separate ways of normalizing the urine values were tested: 1) by dividing the urine biomarker level by the creatinine value and taking the natural log [urine 1 variation], and 2) by dividing the urine biomarker level by the creatinine level and the cystatin level and taking the natural log [urine 2 variation]. In this case it is possible for some values to be negative because the natural log of a fraction is <0.

Of note, for the MRM analyses, the same amount of heavy labeled peptide was spiked into depleted and non-depleted serum; in retrospect, approximately one third this amount would have been more appropriate for non-depleted serum as it would have more closely approximated amounts of the biomarkers targeted for quantification in the non-depleted serum.

Results

1. Technical Validation

To assess analytical variation across all of the targeted analytes, a cost effective strategy for quality control (QC) was adopted a priori for this project. This consisted of creating a representative quality control sample by pooling equal portions of all patient samples within a particular matrix (i.e. synovial fluid, urine or serum). This approach allows for any matrix-specific interferences to be included in the technical variation calculations.

Figure 2:
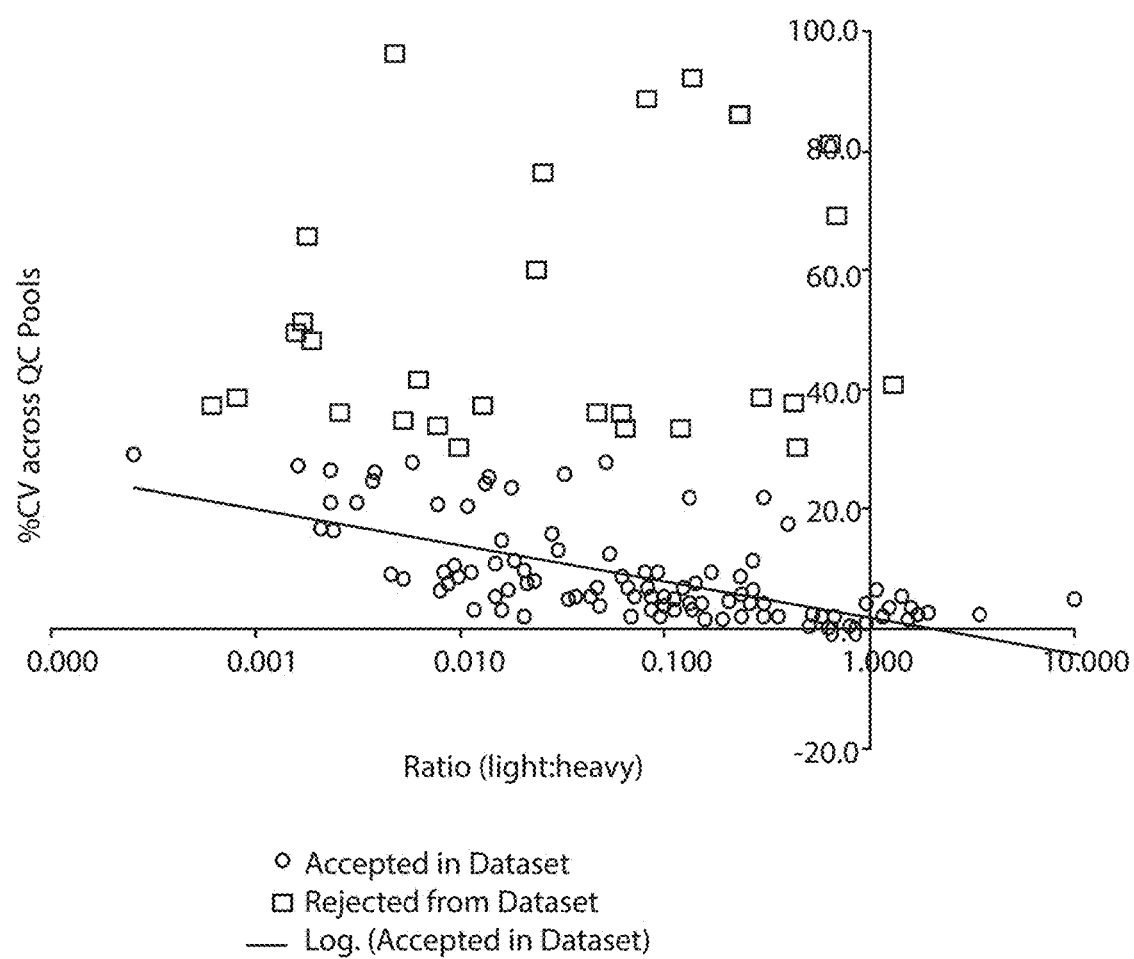
FIG. 2 is a dot plot showing the coefficients of variation for each of the tested peptides and those colored blue and clustering near the log based line were included for further analysis and those in red were not included in the dataset.

The analytical measurements were made from this QC sample many times throughout the analysis of the cohort samples. This allowed the measurement of the reproducibility of the quantification for the exact species of interest at the concentration levels where they are found in the sample. The closer an absolute signal is to its limit of detection or lower limit of quantification, the lower the expected reproducibility (or greater the expected variability). For this study we defined the acceptable upper limit of variability of repeated measurements of any analyte within a sample to be 30% relative to the standard deviation. This limit was based on our expectation that any real biological or treatment group dependent variation would achieve this level of variability or higher; this threshold is consistent with a range of coefficients of variation (CVs 20-35%) for proteomics studies deemed acceptable in a recent summary of a workshop held at the National Institutes of Health with representatives from the multiple communities developing and employing targeted mass spectrometry assays. Carr et al., *Mol Cell Proteomics* 13(3):907-17 (2014). FIG. 2 (above) plots CVs for each of the 147 targeted analytes representing 99 proteins (as a ratio of the heavy to light peptides) across all analyses of the QC sample; of note this does not include the 6 Alcohol Dehydrogenase control peptides. The blue dots represent peptides accepted into the final MRM panel of 146 analytes; the red dots represent the peptides rejected from the final dataset for analysis. As expected, the CVs (blue dots) tend to increase at lower ratios because their quantity approaches the lower limit of quantification for these analytes. The red dots show no correlation to ratio, as their quantification is likely confounded by matrix interferences.

2. Proteomics Results

For this project, candidate prognostic and diagnostic biomarkers were identified by three means: through discovery proteomics experiments in synovial fluid and urine by liquid chromatography mass spectrometry (LC/MS); and a discovery proteomics experiment in depleted serum (serum depleted of the 14 most abundant serum proteins. Based on this work, we selected a potential list of 155 peptides corresponding to 110 proteins for MRM assay development. The MRM assay was evaluated in synovial fluid (pooled samples from 3 progressor and 3 non-progressor knee OA patients) and test sera (3 progressor and 3 non-progressor knee OA patient samples for both depleted and non-depleted serum). Of the original 155 peptides, a total of 146 peptides from 99 proteins were detectable in these test samples and selected for final validation in depleted and non-depleted serum of 124 patients by MRM. Additionally, ELISA based analyses were used to evaluate some prognostic and diagnostic biomarker candidates when commercial ELISA kits were available for a biomarker of interest.

As described above, a final total of 146 peptides (99 proteins) were evaluated in this study by mass spectrometry. Below are listed the results from serum proteomic analysis of the non-depleted serum and the MARS14 depleted serum. MARS14 depleted serum is serum after it has been subjected to a column absorption to remove 14 of the most abundant serum proteins such that the abundance of these proteins does not interfere with the measurement and analysis of other serum proteins. The 14 depleted proteins include the following: albumin, IgG, IgA, transferrin, haptoglobin, antitrypsin, fibrinogen, alpha 2-macroglobulin, IgM, apolipoprotein AI, apolipoprotein AII, complement C3, and transthyretin. To date, more extensive statistical analyses have been performed on the non-depleted serum because results were stronger than with the depleted serum; in general results are consistent between the two. We also experimented with the use of a normalization peptide (actin) in one case (diagnosis of knee level Osteoarthritis) and it showed a slight improvement in AUCs. Further normalization peptides are reported below. A total of 19 of 97 of the panel of OA proteins were predicted to be involved in the pathogenesis of OA and might have the potential to be 'direct biomarkers' of OA; 1 of these 19 was associated with development of a connective tissue disorder; and 16 of the 19 were linked to the process of post-translational modification, protein degradation and synthesis in OA cartilage. A summary of the markers and corresponding peptides for the proteomic results discussed below is shown in Tables 2A, 2B, 2C and 2D.

TABLE 2A

Summary of Markers and Corresponding Peptides; lower case marker names in peptide sequence column indicate markers that were detected by ELISA. All markers listed were found to have a statistically significant association (p-value < 0.05) with osteoarthritis diagnosis, prediction of osteoarthritis progression, or both.

| Marker | Accession No. | Peptide Sequence(s) | SEQ ID NO: X | Diagnos (/ug total protein) | Prognos (/ug total protein) |
|---|---|---|---|---|---|
| CRAC1 | Q9NQ79 | GVASLFAGR | 1 | > | > |
| (CRTAC1) | | SSPYYALR | 2 | > | > |
| A1BG | P04217 | IFFHLNAVALG DGGHYTCR | 3 | > | |
| A2AP | P08697 | SPPGVCSR | 4 | > | |
| | | LCQDLGPGAFR | 5 | < | |
| A2GL | P02750 | VAAGAFQGLR | 6 | > | |
| | | ALGHLDLSGNR | 7 | > | |
| AACT | P01011 | ADLSGITGAR | 8 | | > |
| | | NLAVSQVVHK | 9 | | > |
| | | EQLSLLDR | 10 | | > |
| ACTG | P63261 | VAPEEHPVLLT EA PLNPK | 11 | < | |
| AFAM | P43652 | VNCLQTR | 12 | | |
| AMBP | P02760 | AFIQLWAFDAV K | 13 | | |
| ANT3 | P01008 | ATEDEGSEQK | 14 | | < |
| APOB | P04114 | LAIPEGK | 15 | < | > |
| | | WNFYYSPQSSP DK | 16 | | |

TABLE 2A-continued

Summary of Markers and Corresponding Peptides; lower case marker names in peptide sequence column indicate markers that were detected by ELISA. All markers listed were found to have a statistically significant association (p-value < 0.05) with osteoarthritis diagnosis, prediction of osteoarthritis progression, or both.

| Marker | Accession No. | Peptide Sequence(s) | SEQ ID NO: X | Diagnos (/ug total protein) | Prognos (/ug total protein) |
|---|---|---|---|---|---|
| APOE | P02649 | LQAEAFQAR | 17 | > | |
| APOH | P02749 | ATFGCHDGYSL DGPEEIECTK | 18 | | > |
| B2MG | P61769 | VEHSDLSFSK | 19 | | |
| C1QC | P02747 | VVTFCGHTSK | 20 | <, > | |
| C1R | P00736 | NIGEFCGK | 21 | | |
| | | GLTLHLK | 22 | | > |
| | | GYGFYTK | 23 | | > |
| C1RL | Q9NZP8 | GSEAINAPGDN PAK | 24 | | |
| C4BPA | P04003 | LSLEIEQLELQ R | 25 | > | |
| | | GVGWSHPLPQC EIVK | 26 | > | > |
| C4BPB | P20851 | SQCLEDHTWAP PF | 27 | > | |
| | | PICK | | | |
| CD14 | | cd14 | | | |
| CD163 | | cd163 | | | |
| CD44 | P16070 | YGFIEGHVVIP R | 28 | > | |
| | | cd44 | | | |
| CERU | P00450 | HYYIAAEEIIW NY APSGIDIFTK | 29 | < | |
| | | cerulo | | | |
| | | EYTDASFTNR | 30 | | |
| | | DIASGLIGPLI ICK | 31 | | |
| | | GAYPLSIEPIG VR | 32 | | |
| | | EVGPTNADPVC LAK | 33 | | |
| CFAB | P00751 | QLNEINYEDHK | 34 | | |
| CFAH | P08603 | CLPVTAPENGK | 35 | | > |
| CFAI | P05156 | HGNTDSEGIVE VK | 36 | > | > |
| | | AQLGDLPWQVA IK | 37 | > | |

TABLE 2A-continued

Summary of Markers and Corresponding Peptides; lower case marker names in peptide sequence column indicate markers that were detected by ELISA. All markers listed were found to have a statistically significant association (p-value < 0.05) with osteoarthritis diagnosis, prediction of osteoarthritis progression, or both.

| Marker | Accession No. | Peptide Sequence(s) | SEQ ID NO: X | Diagnos (/ug total protein) | Prognos (/ug total protein) |
|---|---|---|---|---|---|
| CILP1 | O75339 | IVGPLEVNVR | 38 | | |
| C1S | P09871 | LLEVPEGR | 39 | | > |
| CNDP1 | Q96KN2 | ALEQDLPVNIK | 40 | | |
| CO2 | P06681 | SSGQWQTPGATR | 41 | < | |
| | | DGNDHSLWR | 42 | | > |
| CO4B | P0C0L5 | LVNGQSHISLSK | 43 | | |
| CO5 | P01031 | GIYGTISR | 44 | > | > |
| | | TLLPVSKPEIR | 45 | > | > |
| | | IIHFGTR | 46 | > | |
| | | FSYSSGHVHLSSENK | 47 | | |
| | | SYFPESWLWEVHLVPR | 48 | | |
| CO6A3 | P12111 | EVQVFEITENSAK | 49 | > | |
| | | LLPSFVSSENAFYLSPDIR | 50 | | |
| CO8B | P07358 | GILNEIK | 51 | > | > |
| CO8G | P07360 | QLYGDTGVLGR | 52 | > | > |
| CO9 | P02748 | FTPTETNK | 53 | | |
| coll3 | | coll3 | | | |
| COMP | P49747 | NALWHTGDTESQVR | 54 | > | |
| | | SSTGPGEQLR | 55 | > | |
| | | SNPDQADVDHDFVGDACDSDQDQDGDGHQDSR | 56 | | |
| CTX1a | | ctx1a_ctx1b | | | |
| CTX1b | | ctx1a_ctx1b | | | |
| CTX2 | | ctx2 | | | |
| CTXi | | ctxi | | | |
| CXCL7 | P02775 | NIQSLEVIGK | 57 | > | > |
| DOPO | P09172 | VISTLEEPTPQCPTSQGR | 58 | | |
| ECM1 | Q16610 | FCEAEFSVK | 59 | > | |
| FA12 | P00748 | CLEVEGHR | 60 | | |
| FA5 | P12259 | SEAYNTFSER | 61 | > | |
| | | EFNPLVIVGLSK | 62 | > | |
| FBLN1 | P23142 | TGYYFDGISR | 63 | | |
| FBLN3 | Q12805 | NPCQDPYILTPENR | 64 | > | |
| | | ADQVCINLR | 65 | > | |
| FCGBP | Q9Y6R7 | VTASSPVAVLSGHSCAQK | 66 | | |
| FCN3 | O75636 | TFAHYATFR | 67 | | |
| FETUA | P02765 | HTLNQIDEVK | 68 | | |
| | | FSVVYAK | 69 | | > |
| FINC | P02751 | EYLGAICSCTCFGGQR | 70 | | > |
| | | IGDTWSK | 71 | | > |
| GELS | P06396 | GGVASGFK | 72 | > | |
| HA | | HA | | | |
| HABP2 | Q14520 | FCEIGSDDCYVGDGYSYR | 73 | | |
| | | GQCLITQSPPYYR | 74 | > | |
| haptoglobin | | Hapto | | | |
| HEMO | P02790 | QGHNSVFLIK | 75 | | |
| | | hemopexin | | | |
| HEP2 | P05546 | NFGYTLR | 76 | | > |
| | | FTVDRPFLFLIYEHR | 77 | | > |
| HGFA | Q04756 | YIPYTLYSVFNPSDHDLVLIR | 78 | | |
| HRG | P04196 | DSPVLIDFFEDTER | 79 | > | |
| | | GGEGTGYFVDFSVR | 80 | | |

TABLE 2A-continued

Summary of Markers and Corresponding Peptides; lower case marker names in peptide sequence column indicate markers that were detected by ELISA. All markers listed were found to have a statistically significant association (p-value < 0.05) with osteoarthritis diagnosis, prediction of osteoarthritis progression, or both.

| Marker | Accession No. | Peptide Sequence(s) | SEQ ID NO: X | Diagnos (/ug total protein) | Prognos (/ug total protein) |
|---|---|---|---|---|---|
|  |  | YWNDCEPPDSR | 81 |  | > |
|  |  | GEVLPLPEANFPS FPLPHHK | 82 |  |  |
|  |  | SSTTKPPFKPHGSR | 83 |  |  |
| hyaluronan |  | hyaluronan |  |  |  |
| IC1 | P05155 | LVLLNAIYLSAK | 84 |  |  |
| ITIH1 | P19827 | VTFQLTYEEVLK | 85 |  |  |
| ITIH4 | Q14624 | FKPTLSQQQK | 86 |  | > |
| KLKB1 | P03952 | VSEGNHDIALIK | 87 |  | > |
| KNG1 | P01042 | LDDDLEHQGGHVLDHGHK | 88 | > |  |
|  |  | kinno |  |  |  |
| LAMA2 | P24043 | TPYNILSSPDYVGVTK | 89 |  |  |
| LUM | P51884 | ILGPLSYSK | 90 | > |  |
|  |  | VANEVTLN | 91 | > |  |
|  |  | SLEDLQLTHNK | 92 |  |  |
| LYAM1 | P14151 | AEIEYLEK | 93 |  |  |
| MASP1 | P48740 | TGVITSPDFPNPYPK | 94 |  |  |
| PCOC1 | Q15113 | TGGLDLPSPPTGASLK | 95 | > |  |
| PGCA | P16112 | VSLPNYPAIPSD ATLEVQSLR | 96 | < | > |
|  |  | EVVLLVATEGR | 97 |  |  |
| PHLD | P80108 | FGSSLITVR | 98 | > | > |
| PLF4 | P02776 | ICLDLQAPLYK | 99 | > | > |
| PLMN | P00747 | HSIFTPETNPR | 100 |  | > |
| PRG4 | Q92954 | ITEVWGIPSPIDTVFTR | 101 |  | > |
|  |  | DQYYNIDVPSR | 102 |  | > |
| RET4 | P02753 | LIVHNGYCDGR | 103 |  | > |
| SAMP | P02743 | AYSDLSR | 104 | > | > |
| SHBG | P04278 | IALGGLLFPASNLR | 105 | < |  |
| TENX | P22105 | TVTVEDLEPGK | 106 |  |  |
| TETN | P05452 | TFHEASEDCISR | 107 | > |  |
| THBG | P05543 | NALALFVLPK | 108 |  |  |
|  |  | AVLHIGEK | 109 |  |  |
| THRB | P00734 | NPDSSTTGPWCYTTDPTVR | 110 |  | > |
| TIMP1 | P01033 | GFQALGDAADIR | 111 | > | > |
| TSP1 | P07996 | FVFGTTPEDILR | 112 | > | > |
| TSP4 | P35443 | DVDIDSYPDEEL PCSAR | 113 | > |  |
|  |  | AVAEPGIQLK | 114 |  |  |
| VTDB | P02774 | vitd_binding |  |  |  |
|  |  | ELPEHTVK | 115 |  |  |
|  |  | VLEPTLK | 116 |  |  |
|  |  | LCDNLSTK | 117 |  |  |
|  |  | SCESNSPFPVHPG TAECCTK | 118 |  |  |
|  |  | SLGECCDVEDST TCFNAK | 119 |  |  |
| VTNC | P04004 | QPQFISR | 120 | < |  |
| ZA2G | P25311 | DIVEYYNDSNGSHVLQGR | 121 |  |  |
| ZPI | Q9UK55 | VVNPTLL | 122 |  | > |

TABLE 2B

Peptide key

| | | Protein name | Biology |
|---|---|---|---|
| A1BG | P04217 | Alpha-1B-glycoprotein | Plasma protein |
| A2AP | P08697 | Alpha-2-antiplasmin | Acute phase serine protease inhibitor |
| A2GL | P02750 | Leucine-rich alpha-2-glycoprotein | Plasma protein |
| AACT | P01011 | Alpha-1-antichymotrypsin | Acute phase serine protease inhibitor |
| ACTG | P63261 | Actin, cytoplasmic 2 | Cytoskeleton component |
| AFAM | P43652 | Afamin | Vitamin E binding protein |
| AMBP | P02760 | Protein AMBP | Inter-alpha-trypsin inhibitor (a serpin) |
| ANGT | P01019 | Angiotensinogen | regulator of blood pressure, body fluid and electrolyte homeostasis |
| ANT3 | P01008 | Antithrombin-III | serine protease inhibitor in blood coagulation |
| APOB | P04114 | Apolipoprotein B-100 | major protein constituent of chylomicrons, LDL and VLDL |
| APOE | P02649 | Apolipoprotein E | binding, internalization, and catabolism of lipoprotein particles |
| APOH | P02749 | Beta-2-glycoprotein 1 | Heparin sulphate binding plasma protein |
| B2MG | P61769 | Beta-2-microglobulin | Component of the class I MHC |
| BTD | P43251 | Biotinidase | release of biotin from biocytin |
| C1QC | P02747 | Complement C1q subcomponent subunit C | Complement pathway |
| C1R | P00736 | Complement C1r subcomponent | Complement pathway |
| C1RL | Q9NZP8 | Complement C1r subcomponent-like protein | Mediates the proteolytic cleavage of HP/haptoglobin in the ER |
| C1S | P09871 | Complement C1s subcomponent | Complement pathway |
| C4BPA | P04003 | C4b-binding protein alpha chain | Complement pathway |
| C4BPB | P20851 | C4b-binding protein beta chain | Complement pathway |
| CD44 | P16070 | CD44 | HA cell surface binding receptor |
| CERU | P00450 | Ceruloplasmin | ferroxidase activity and iron transport across the cell membrane |
| CFAB | P00751 | Complement factor B | Complement pathway |
| CFAH | P08603 | Complement factor H | Complement pathway |
| CFAI | P05156 | Complement factor I | Complement pathway |
| CILP1 | O75339 | Cartilage intermediate layer protein 1 | Cartilage protein |
| CNDP1 | Q96KN2 | Beta-Ala-His dipeptidase | Serum metaloproteinase |
| CO2 | P06681 | Complement C2 | Complement pathway |
| CO4B | P0C0L5 | Complement C4-B | Complement pathway |
| CO5 | P01031 | Complement C5 | Complement pathway |
| CO5A1 | P20908 | Collagen alpha-1(V) chain | Type V fibular collagen |
| CO5A1 | P20908 | Complement component C6 | Complement pathway |
| CO6 | P13671 | Complement component C6 | Complement pathway |
| CO6A3 | P12111 | Collagen alpha-3(VI) chain | Collagen VI, cell binding |
| CO8B | P07358 | Complement component C8 beta chain | Complement pathway |
| CO8G | P07360 | Complement component C8 gamma chain | Complement pathway |
| CO9 | P02748 | Complement component C9 | Complement pathway |
| CO9A3 | Q14050 | Collagen alpha-3(IX) chain | Type IX collagen |
| COMP | P49747 | Cartilage oligomatrix protein | Cartilage ECM protein |
| COOA1 | Q17RW2 | Collagen alpha-1(XXIV) chain | Fibular collagen XIV |
| CRAC1 CRTAC | Q9NQ79 | Cartilage acidic protein 1 | ECM protein found in cartilage, bone and lung |
| CSPG2 | P13611 | Versican core protein | ECM protein binds HA |
| CXCL7 | P02775 | Platelet basic protein | stimulates DNA synthesis, mitosis, glycolysis, cAMP accumulation, prostaglandin E2, and synthesis of HA and GAG |
| DOPO | P09172 | Dopamine beta-hydroxylase | Conversion of dopamine to noradrenaline |
| ECM1 | Q16610 | Extracellular matrix protein 1 | Involved in endochondral bone formation as negative regulator of bone mineralization |
| F13B | P05160 | Coagulation factor XIII B chain | Glycoprotein involved in blood coagulation |

TABLE 2B-continued

Peptide key

| | | Protein name | Biology |
|---|---|---|---|
| FA12 | P00748 | Coagulation factor XII | Serine proteinase involved in blood coagulation |
| FA5 | P12259 | Coagulation factor V | Blood coagulation, Hemostasis |
| FBLN1 | P23142 | Fibulin-1 | ECM protein |
| FBLN3 | Q12805 | EGF-containing fibulin-like extracellular matrix protein 1 | Fibulin-3, ECM protein, May function as a negative regulator of chondrocyte differentiation |
| FCGBP | Q9Y6R7 | IgGFc-binding protein | May be involved in the maintenance of the mucosal structure |
| FCN3 | O75636 | Ficolin-3 | May function in innate immunity |
| FETUA | P02765 | Alpha-2-HS-glycoprotein | influences the mineral phase of bone |
| FINC | P02751 | Fibronectin | ECM multiple roles |
| FREM2 | Q5SZK8 | FRAS1-related extracellular matrix protein 2 | Cell membrane adhesion protein |
| GELS | P06396 | Gelsolin | Plasma protein |
| HABP2 | Q14520 | Hyaluronan-binding protein 2 | Plasma serine proteinase |
| HEMO | P02790 | Hemopexin | Binds heme and transports it to the liver |
| HEP2 | P05546 | Heparin cofactor 2 | Blood coagulation, Chemotaxis, hemostatsis |
| HGFA | Q04756 | Hepatocyte growth factor activator | Activates hepatocyte growth factor |
| HPLN1 | P10915 | Hyaluronan and proteoglycan link protein 1 | Link protein, cartilage ECM HA binding protein |
| HRG | P04196 | Histidine-rich glycoprotein | Angiogenesis, Blood coagulation, Chemotaxis, Fibrinolysis, Hemostasis |
| IC1 | P05155 | Plasma protease C1 inhibitor | SERPING1 inhibits C1 of complement |
| IRK4 | P48050 | Inward rectifier potassium channel 4 | Potassium channel |
| ITIH1 | P19827 | Inter-alpha-trypsin inhibitor heavy chain H1 | Protease inhibitor, Serine protease inhibitor, binds HA |
| ITIH4 | Q14624 | Inter-alpha-trypsin inhibitor heavy chain H4 | Acute phase protein |
| KIZ | Q2M2Z5 | Centrosomal protein kizuna | Centrosomal protein |
| KLKB1 | P03952 | Plasma kallikrein | Serine protease |
| KNG1 | P01042 | Kininogen-1 | Protease inhibitor, Thiol protease inhibitor, Vasoactive, Vasodilator |
| LAMA2 | P24043 | Laminin subunit alpha-2 | Cell ECM binding |
| LUM | P51884 | Lumican | Cartilage ECM protein |
| LYAM1 | P14151 | L-selectin | rolling of leukocytes |
| MASP1 | P48740 | Mannan-binding lectin serine protease 1 | Lectin complement pathway |
| MAST3 | O60307 | Microtubule-associated serine/threonine-protein kinase 3 | Cytoplasmic enzyme |
| PCOC1 | Q15113 | Procollagen C-endopeptidase enhancer 1 | Type 1 collagen fibril formation |
| PGBM | P98160 | Perlecan | ECM protein |
| PGCA | P16112 | Aggrecan core protein | Cartilage ECM HA binding protein |
| PGRP2 | Q96PD5 | N-acetylmuramoyl-L-alanine amidase | May play a scavenger role by digesting biologically active peptidoglycan |
| PHLD | P80108 | Phosphatidylinositol-glycan-specific phospholipase D | hydrolyzes the inositol phosphate linkage in proteins |
| PLF4 | P02776 | Platelet factor 4 | Released during platelet aggregation |
| PLMN | P00747 | Plasminogen | Blood coagulation, Fibrinolysis, Hemostasis. Tissue remodeling |
| PRG4 | Q92954 | Proteoglycan 4 | Lubricin, cartilage ECM protein |
| PRLD2 | Q8N945 | PRELI domain containing 2 | Mitrochondrial |
| PZP | P20742 | Pregnancy zone protein | inhibit all four classes of proteinases |
| RET4 | P02753 | Retinol-binding protein 4 | Retinol transporter protein |
| RTN4 | Q9NQC3 | Reticulon-4 | neurogenesis |
| RUNX2 | Q13950 | Runt-related transcription factor 2 | osteoblastic differentiation and skeletal morphogenesis |
| SAMP | P02743 | Serum amyloid P-component | Can interact with DNA and histones and may scavenge nuclear material released from damaged circulating cells |
| SEPP1 | P49908 | Selenoprotein P | Selenium transport and ECM antioxidant |
| SHBG | P04278 | Sex hormone-binding globulin | androgen transport protein |

TABLE 2B-continued

Peptide key

| | | Protein name | Biology |
|---|---|---|---|
| SPTA2 | Q13813 | Spectrin alpha chain, non-erythrocytic 1 | Ca depended cytoskeletal re-organization |
| TENX | P22105 | Tenascin X | Anti-adhesive ECM glycoprotein |
| TETN | P05452 | Tetranectin | Plasma protein |
| THBG | P05543 | Thyroxine-binding globulin | Major thyroid hormone transport protein in serum. |
| THRB | P00734 | Prothrombin | Acute phase, Blood coagulation, Hemostasis |
| TIMP1 | P01033 | Tissue inhibitor metalloproteinase 1 | MMP inhibitor |
| TNR6C | Q9HCJ0 | trinucleotide repeat containing 6C | miRNA silencing |
| TSP1 | P07996 | Thrombospondin 1 | Cell/cell/matrix binding |
| TSP4 | P35443 | Thrombospondin-4 | Mediates cell/cell and cell/matrix adhesion |
| VTDB | P02774 | Vitamin D-binding protein | Vitamin D transporter protein |
| VTNC | P04004 | vitronectin | Cell/matrix adhesion factor |
| ZA2G | P25311 | Zinc-alpha-2-glycoprotein | Stimulates lipid degradation in adipocytes |
| ZPI | Q9UK55 | Protein Z-dependent protease inhibitor | Blood coagulation, Hemostasis |

TABLE 2C

Diagnostic Data (OA = Osteoarthritis, C = Control)

Diagnostic Data

MRM markers; non-depleted Serum; knee

| phenotype (SEQ ID NO: X) | OAmean | OAsd | Cmean | Csd |
|---|---|---|---|---|
| Knee_JSN_Pheno_Q9NQ79_CRAC1_GVASLFAGR (1) | −5.3467 | 0.31328 | −5.5677 | 0.29133 |
| Knee_JSN_Pheno_P02775_CXCL7_NIQSLEVIGK (57) | −1.579 | 0.26191 | −1.8924 | 0.78391 |
| Knee_JSN_Pheno_P04217_A1BG_IFFHLNAVALGDGGHYTCR (3) | 0.01795 | 0.2559 | −0.0399 | 0.22048 |
| Knee_JSN_Pheno_P02776_PLF4_ICLDLQAPLYK (99) | −2.6781 | 0.31999 | −2.9236 | 0.74256 |
| Knee_JSN_Pheno_P05452_TETN_TFHEASEDCISR (107) | −2.7375 | 0.23026 | −2.824 | 0.23499 |
| Knee_JSN_Pheno_P01033_TIMP1_GFQALGDAADIR (111) | −5.5478 | 0.39529 | −5.7389 | 0.421 |
| Knee_JSN_Pheno_P49747_COMP_NALWHTGDTESQVR (54) | −5.2222 | 0.39632 | −5.4563 | 0.48604 |
| Knee_JSN_Pheno_P04003_C4BPA_LSLEIEQLELQR (25) | −0.6158 | 0.24333 | −0.732 | 0.21636 |
| Knee_JSN_Pheno_P07996_TSP1_FVFGTTPEDILR (112) | −3.9111 | 0.33405 | −4.1246 | 0.70016 |
| Knee_JSN_Pheno_P80108_PHLD_FGS_S_LITVR (98) | −3.9109 | 0.31233 | −4.0202 | 0.295 |
| Knee_JSN_Pheno_P16112_PGCA_VSLPNYPAIPSDATLEVQSLR (96) | −8.5077 | 0.60466 | −8.3027 | 0.59736 |
| Knee_JSN_Pheno_P04003_C4BPA_GVGWSHPLPQCEIVK (26) | −0.6333 | 0.30499 | −0.7658 | 0.27236 |
| Knee_JSN_Pheno_P01031_CO5_GIYGTISR (44) | −2.6335 | 0.19845 | −2.727 | 0.18412 |
| Knee_JSN_Pheno_P51884_LUM_ILGPLSYSK (90) | −2.2931 | 0.18757 | −2.381 | 0.17292 |

TABLE 2C-continued

Diagnostic Data (OA = Osteoarthritis, C = Control)

| | | | | |
|---|---|---|---|---|
| Knee_JSN_Pheno_P01031_CO5_TLLPVSK PEIR (45) | −2.6148 | 0.19708 | −2.7026 | 0.18569 |
| Knee_JSN_Pheno_P07360_CO8G_QLYGD TGVLGR (52) | −4.6571 | 0.35419 | −4.8008 | 0.38448 |
| Knee_JSN_Pheno_P20851_C4BPB_SQCLE DHTWAPPFPICK (27) | −2.4987 | 0.25857 | −2.6078 | 0.24415 |
| Knee_JSN_Pheno_P01031_CO5_IIHFGTR (46) | −2.4834 | 0.2052 | −2.5725 | 0.19137 |
| Knee_JSN_Pheno_P05156_CFAI_HGNTDS EGIVEVK (36) | −2.1353 | 0.23576 | −2.2203 | 0.2542 |
| Knee_JSN_Pheno_P02743_SAMP_AYSDL SR (104) | −1.172 | 0.26186 | −1.3063 | 0.39507 |
| Knee_JSN_Pheno_Q9NQ79_CRAC1_SSPY YALR (2) | −5.3076 | 0.32576 | −5.4371 | 0.30832 |
| Knee_JSN_Pheno_Q15113_PCOC1_TGGL DLPSPPTGASLK (95) | −5.0009 | 0.19706 | −5.0763 | 0.17589 |
| Knee_JSN_Pheno_P12259_FA5_SEAYNTF SER (61) | −4.6902 | 0.23862 | −4.7772 | 0.27625 |
| Knee_JSN_Pheno_P51884_LUM_VANEVT LN (91) | −1.3903 | 0.22821 | −1.4664 | 0.22184 |
| Knee_JSN_Pheno_P04278_SHBG_IALGGL LFPASNLR (105) | −4.7876 | 0.75918 | −4.5138 | 0.65685 |
| Knee_KL_Pheno_Q9NQ79_CRAC1_GVAS LFAGR (1) | −5.36 | 0.30055 | −5.634 | 0.28483 |
| Knee_KL_Pheno_Q9NQ79_CRAC1_SSPY YALR (2) | −5.2986 | 0.30834 | −5.5093 | 0.30855 |
| Knee_KL_Pheno_P07360_CO8G_QLYGDT GVLGR (52) | −4.6643 | 0.36247 | −4.8469 | 0.3723 |
| Knee_KL_Pheno_P49747_COMP_NALWH TGDTESQVR (54) | −5.2483 | 0.40041 | −5.5027 | 0.51099 |
| Knee_KL_Pheno_P07358_CO8B_GILNEIK (51) | −4.337 | 0.36071 | −4.4394 | 0.33841 |
| Knee_KL_Pheno_P04004_VTNC_QPQFIS R(120) | −2.5841 | 0.32518 | −2.4986 | 0.31075 |
| Knee_KL_Pheno_P04278_SHBG_IALGGL LFPASNLR (105) | −4.7795 | 0.74084 | −4.415 | 0.62606 |
| Knee_KL_Pheno_P02775_CXCL7_NIQSLE VIGK (57) | −1.6465 | 0.43393 | −1.8899 | 0.80079 |
| Knee_KL_Pheno_Q15113_PC0C1_TGGLD LPSPPTGASLK (95) | −5.0083 | 0.20352 | −5.0934 | 0.14771 |
| Knee_KL_Pheno_P12111_CO6A3_EVQVF EITENSAK (49) | −5.7888 | 0.27059 | −5.9159 | 0.24476 |
| Knee_KL_Pheno_P51884_LUM_ILGPLSY SK (90) | −2.3063 | 0.18911 | −2.3918 | 0.16554 |
| Knee_KL_Pheno_P02743_SAMP_AYSDLS R(104) | −1.195 | 0.2826 | −1.317 | 0.41746 |
| Knee_KL_Pheno_P01031_CO5_IIHFGTR (46) | −2.5003 | 0.21274 | −2.5762 | 0.17348 |
| Knee_KL_Pheno_P51884_LUM_VANEVT LN (91) | −1.4005 | 0.22997 | −1.4781 | 0.21611 |
| Knee_KL_Pheno_P01031_CO5_GIYGTISR (44) | −2.6535 | 0.21307 | −2.7265 | 0.15017 |

TABLE 2C-continued

| Diagnostic Data (OA = Osteoarthritis, C = Control) | | | | |
|---|---|---|---|---|
| Knee_KL_Pheno_P04003_C4BPA_LSLEIE QLELQR (25) | -0.6435 | 0.25492 | -0.7256 | 0.18876 |
| Knee_OST_Pheno_Q9NQ79_CRAC1_GVA SLFAGR (1) | -5.353 | 0.30661 | -5.5993 | 0.28726 |
| Knee_OST_Pheno_Q9NQ79_CRAC1_SSP YYALR (2) | -5.2892 | 0.30785 | -5.4886 | 0.31058 |
| Knee_OST_Pheno_P04004_VTNC_QPQFIS R(120) | -2.5963 | 0.31787 | -2.4944 | 0.32087 |
| Knee_OST_Pheno_P49747_COMP_NALW HTGDTESQVR (54) | -5.2442 | 0.40004 | -5.467 | 0.50102 |
| Knee_OST_Pheno_P04278_SHBG_IALGG LLFPASNLR (105) | -4.7799 | 0.74413 | -4.4746 | 0.65493 |
| Knee_OST_Pheno_P12111_C06A3_EVQV FEITENSAK (49) | -5.7842 | 0.27689 | -5.9018 | 0.24009 |
| Knee_OST_Pheno_Q15113_PCOC1_TGGL DLPSPPTGASLK (95) | -5.0092 | 0.20737 | -5.078 | 0.15463 |
| MRM markers; non-depleted Serum; person | | | | |
| Knee_JSN_person_Pheno_P00450_CERU_ HYYIAAEEIIWNYAPSGIDIFTK (29) | 0.65572 | 0.24983 | 0.76035 | 0.27569 |
| Knee_JSN_person_Pheno_P01031_C05_GI YGTISR (44) | -2.6381 | 0.20909 | -2.7346 | 0.16563 |
| Knee_JSN_person_Pheno_P01031_C05_II HFGTR (46) | -2.4887 | 0.21661 | -2.5783 | 0.17261 |
| Knee_JSN_person_Pheno_P01031_C05_TL LPVSKPEIR (45) | -2.6187 | 0.20754 | -2.7103 | 0.16802 |
| Knee_JSN_person_Pheno_P01033_TIMP1_ GFQALGDAADIR (111) | -5.5604 | 0.40065 | -5.7497 | 0.42285 |
| Knee_JSN_person_Pheno_P02743_SAMP_ AYSDLSR (104) | -1.1745 | 0.27542 | -1.3229 | 0.39912 |
| Knee_JSN_person_Pheno_P02775_CXCL7_ NIQSLEVIGK (57) | -1.5899 | 0.27108 | -1.924 | 0.83168 |
| Knee_JSN_person_Pheno_P02776_PLF4_IC LDLQAPLYK (99) | -2.6915 | 0.33412 | -2.9413 | 0.78317 |
| Knee_JSN_person_Pheno_P04003_C4BPA_ GVGWSHPLPQCEIVK (26) | -0.6459 | 0.33432 | -0.7677 | 0.2194 |
| Knee_JSN_person_Pheno_P04003_C4BPA_ LSLEIEQLELQR (25) | -0.6165 | 0.25436 | -0.7484 | 0.18988 |
| Knee_JSN_person_Pheno_P04217_A1BG_I FFHLNAVALGDGGHYTCR (3) | 0.00845 | 0.27983 | -0.0351 | 0.17265 |
| Knee_JSN_person_Pheno_P04278_SHBG_I ALGGLLFPASNLR (105) | -4.7677 | 0.77275 | -4.501 | 0.62726 |
| Knee_JSN_person_Pheno_P07360_CO8G_ QLYGDTGVLGR (52) | -4.6695 | 0.36108 | -4.8047 | 0.38572 |
| Knee_JSN_person_Pheno_P07996_TSP1_F VFGTTPEDILR (112) | -3.9283 | 0.35544 | -4.1322 | 0.73241 |
| Knee_JSN_person_Pheno_P12259_FA5_SE AYNTFSER (61) | -4.6923 | 0.24286 | -4.7873 | 0.27747 |
| Knee_JSN_person_Pheno_P20851_C4BPB_ SQCLEDHTWAPPFPICK (27) | -2.5112 | 0.27892 | -2.6064 | 0.21459 |
| Knee_JSN_person_Pheno_P49747_COMP_ NALWHTGDTESQVR (54) | -5.2389 | 0.40342 | -5.4677 | 0.49665 |

TABLE 2C-continued

| Diagnostic Data (OA = Osteoarthritis, C = Control) | | | | |
|---|---|---|---|---|
| Knee_JSN_person_Pheno_P51884_LUM_ILGPLSYSK (90) | −2.2943 | 0.18871 | −2.3925 | 0.16777 |
| Knee_JSN_person_Pheno_P51884_LUM_VANEVTLN (91) | −1.3877 | 0.23105 | −1.4815 | 0.21506 |
| Knee_JSN_person_Pheno_Q15113_PCOC1_TGGLDLPSPPTGASLK (95) | −4.9982 | 0.19726 | −5.0915 | 0.16919 |
| Knee_JSN_person_Pheno_Q9NQ79_CRAC1_GVASLFAGR (1) | −5.3647 | 0.31833 | −5.5753 | 0.28924 |
| Knee_JSN_person_Pheno_Q9NQ79_CRAC1_SSPYYALR (2) | −5.3165 | 0.32877 | −5.4439 | 0.30529 |
| Knee_KL_person_Pheno_P01031_CO5_GIYGTISR (44) | −2.6531 | 0.21059 | −2.7391 | 0.14588 |
| Knee_KL_person_Pheno_P01031_CO5_IIHFGTR (46) | −2.4986 | 0.21063 | −2.5922 | 0.1707 |
| Knee_KL_person_Pheno_P02743_SAMP_AYSDLSR (104) | −1.1947 | 0.27677 | −1.3369 | 0.44546 |
| Knee_KL_person_Pheno_P02775_CXCL7_NIQSLEVIGK (57) | −1.6407 | 0.42587 | −1.9424 | 0.85113 |
| Knee_KL_person_Pheno_P04278_SHBG_IALGGLLFPASNLR (105) | −4.7405 | 0.75939 | −4.4535 | 0.59653 |
| Knee_KL_person_Pheno_P05156_CFAI_AQLGDLPWQVAIK (37) | −2.3816 | 0.24298 | −2.5067 | 0.27195 |
| Knee_KL_person_Pheno_P05156_CFAI_HGNTDSEGIVEVK (36) | −2.1467 | 0.24629 | −2.247 | 0.24236 |
| Knee_KL_person_Pheno_P07360_CO8G_QLYGDTGVLGR (52) | −4.6628 | 0.36307 | −4.8793 | 0.36711 |
| Knee_KL_person_Pheno_P12111_CO6A3_EVQVFEITENSAK (49) | −5.7924 | 0.26658 | −5.927 | 0.25429 |
| Knee_KL_person_Pheno_P12259_FA5_SEAYNTFSER (61) | −4.7013 | 0.24808 | −4.8058 | 0.27986 |
| Knee_KL_person_Pheno_P49747_COMP_NALWHTGDTESQVR (54) | −5.2524 | 0.39475 | −5.5326 | 0.5373 |
| Knee_KL_person_Pheno_P51884_LUM_ILGPLSYSK (90) | −2.3066 | 0.18753 | −2.4043 | 0.16517 |
| Knee_KL_person_Pheno_P51884_LUM_VANEVTLN (91) | −1.3978 | 0.22966 | −1.497 | 0.21235 |
| Knee_KL_person_Pheno_Q15113_PCOC1_TGGLDLPSPPTGASLK (95) | −5.0045 | 0.20633 | −5.116 | 0.11555 |
| Knee_KL_person_Pheno_Q9NQ79_CRAC1_GVASLFAGR (1) | −5.365 | 0.30117 | −5.6649 | 0.27366 |
| Knee_KL_person_Pheno_Q9NQ79_CRAC1_SSPYYALR (2) | −5.2981 | 0.31394 | −5.5437 | 0.28344 |
| Knee_KL_person_Pheno_Q9UK55_ZPI_VVNPTLL (122) | −3.0199 | 0.13919 | −3.0653 | 0.15335 |
| Knee_OST_person_Pheno_P02775_CXCL7_NIQSLEVIGK (57) | −1.6482 | 0.43797 | −1.8835 | 0.8009 |
| Knee_OST_person_Pheno_P04004_VTNC_QPQFISR (120) | −2.5885 | 0.33293 | −2.4911 | 0.29601 |
| Knee_OST_person_Pheno_P07360_CO8G_QLYGDTGVLGR (52) | −4.6736 | 0.37267 | −4.8264 | 0.36566 |
| Knee_OST_person_Pheno_P12111_CO6A3_EVQVFEITENSAK (49) | −5.7868 | 0.27448 | −5.9182 | 0.2382 |

TABLE 2C-continued

| Diagnostic Data (OA = Osteoarthritis, C = Control) | | | | |
|---|---|---|---|---|
| Knee_OST_person_Pheno_P49747_COMP_NALWHTGDTESQVR (54) | -5.2438 | 0.39886 | -5.5084 | 0.51353 |
| Knee_OST_person_Pheno_P63261_ACTG_VAPEEHPVLLTEAPLNPK (11) | -4.1926 | 0.28264 | -4.0727 | 0.29266 |
| Knee_OST_person_Pheno_Q15113_PCOC1_TGGLDLPSPPTGASLK (95) | -5.0081 | 0.2103 | -5.0927 | 0.13171 |
| Knee_OST_person_Pheno_Q9NQ79_CRAC1_GVASLFAGR (1) | -5.357 | 0.3055 | -5.6367 | 0.27386 |
| Knee_OST_person_Pheno_Q9NQ79_CRAC1_SSPYYALR (2) | -5.2931 | 0.3177 | -5.5175 | 0.28595 |
| Knee_OST_person_Pheno_Q9UK55_ZPI_VVNPTLL (122) | -3.0144 | 0.12597 | -3.0693 | 0.1705 |
| MRM markers; depleted Serum; person; actin | | | | |
| Knee_JSN_person_Pheno_P02776_PLF4_ICLDLQAPLYK (99) | 0.01106 | 0.56919 | -0.0167 | 0.52339 |
| Knee_JSN_person_Pheno_P06396_GELS_GGVASGFK (72) | 0.01656 | 0.24249 | -0.0285 | 0.2353 |
| Knee_JSN_person_Pheno_P08697_A2AP_SPPGVCSR (4) | 0.20908 | 0.55165 | -0.3041 | 0.41444 |
| Knee_JSN_person_Pheno_P08697_A2AP_LCQDLGPGAFR (5) | -0.1708 | 0.72306 | 0.24376 | 0.29575 |
| Knee_JSN_person_Pheno_P04114_APOB_LAIPEGK (15) | -0.0027 | 0.32783 | 0.01013 | 0.3457 |
| Knee_JSN_person_Pheno_P02649_APOE_LQAEAFQAR (17) | 0.08819 | 0.4891 | -0.1192 | 0.48267 |
| Knee_JSN_person_Pheno_P02747_C1QC_VVTFCGHTSK (20) | -0.0366 | 0.91229 | 0.08887 | 0.78024 |
| Knee_JSN_person_Pheno_P05156_CFAI_AQLGDLPWQVAIK (37) | 0.01703 | 0.2518 | -0.0191 | 0.24696 |
| Knee_JSN_person_Pheno_P06681_CO2_SSGQWQTPGATR (41) | -0.1684 | 0.76581 | 0.25677 | 0.27432 |
| Knee_JSN_person_Pheno_P01031_CO5_GIYGTISR (44) | -0.0594 | 0.43213 | 0.09809 | 0.26792 |
| Knee_JSN_person_Pheno_P12111_CO6A3_EVQVFEITENSAK (49) | 0.05255 | 0.2943 | -0.0797 | 0.23417 |
| Knee_JSN_person_Pheno_P07360_CO8G_QLYGDTGVLGR (52) | 0.05261 | 0.30651 | -0.0672 | 0.31322 |
| Knee_JSN_person_Pheno_Q9NQ79_CRAC1_SSPYYALR (2) | 0.08623 | 0.38824 | -0.1257 | 0.34708 |
| Knee_JSN_person_Pheno_Q9NQ79_CRAC1_GVASLFAGR (1) | 0.09636 | 0.33552 | -0.1408 | 0.33742 |
| Knee_JSN_person_Pheno_P12259_FA5_SEAYNTFSER (61) | -0.0749 | 0.41656 | 0.11694 | 0.26129 |
| Knee_JSN_person_Pheno_Q12805_FBLN3_ADQVCINLR (65) | 0.05341 | 0.36555 | -0.0956 | 0.29821 |
| Knee_JSN_person_Pheno_P01042_KNG1_LDDDLEHQGGHVLDHGHK (88) | 0.0016 | 0.76436 | 0.0537 | 0.40236 |
| Knee_JSN_person_Pheno_Q15113_PCOC1_TGGLDLPSPPTGASLK (95) | 0.04065 | 0.28654 | -0.0545 | 0.28022 |
| Knee_JSN_person_Pheno_P80108_PHLD_FGSSLITVR (98) | 0.06571 | 0.6118 | -0.1345 | 0.52321 |

TABLE 2C-continued

| Diagnostic Data (OA = Osteoarthritis, C = Control) | | | | |
|---|---|---|---|---|
| Knee_JSN_person_Pheno_P02743_SAMP_AYSDLSR (104) | 0.04589 | 0.26942 | -0.075 | 0.30542 |
| Knee_JSN_person_Pheno_P05452_TETN_TFHEASEDCISR (107) | 0.02835 | 0.28053 | -0.0469 | 0.25301 |
| Knee_JSN_person_Pheno_P01033_TIMP1_GFQALGDAADIR (111) | 0.04351 | 0.34846 | -0.052 | 0.19604 |
| Knee_JSN_person_Pheno_P49747_COMP_SSTGPGEQLR (55) | -0.1264 | 0.55906 | 0.20054 | 0.42498 |
| Knee_JSN_person_Pheno_P35443_TSP4_DVDIDSYPDEELPCSAR (113) | 0.07752 | 0.49144 | -0.1112 | 0.35704 |
| Knee_JSN_person_Pheno_Q12805_FBLN3_NPCQDPYILTPENR (64) | 0.06224 | 0.39736 | -0.1043 | 0.27103 |
| Knee_KL_person_Pheno_P02776_PLF4_ICLDLQAPLYK (99) | 0.01508 | 0.56529 | -0.0374 | 0.51299 |
| Knee_KL_person_Pheno_P06396_GELS_GGVASGFK (72) | 0.01122 | 0.24343 | -0.0334 | 0.2305 |
| Knee_KL_person_Pheno_P23142_FBLN1_TGYYFDGISR (63) | 0.01083 | 0.28993 | -0.0576 | 0.25805 |
| Knee_KL_person_Pheno_P08697_A2AP_SPPGVCSR (4) | 0.15955 | 0.57776 | -0.3861 | 0.22829 |
| Knee_KL_person_Pheno_P08697_A2AP_LCQDLGPGAFR (5) | -0.1189 | 0.68515 | 0.28116 | 0.2684 |
| Knee_KL_person_Pheno_P02649_APOE_LQAEAFQAR (17) | 0.07706 | 0.46658 | -0.1739 | 0.52368 |
| Knee_KL_person_Pheno_P02747_C1QC_VVTFCGHTSK (20) | -0.0097 | 0.88292 | 0.07314 | 0.81026 |
| Knee_KL_person_Pheno_P16070_CD44_YGFIEGHVVIPR (28) | 0.01844 | 0.2285 | -0.0494 | 0.20504 |
| Knee_KL_person_Pheno_P08603_CFAH_CLPVTAPENGK (35) | 0.02996 | 0.26309 | -0.0792 | 0.20569 |
| Knee_KL_person_Pheno_P06681_CO2_SSGQWQTPGATR (41) | -0.1153 | 0.72103 | 0.29553 | 0.25057 |
| Knee_KL_person_Pheno_P01031_CO5_GIYGTISR (44) | -0.0458 | 0.42048 | 0.12717 | 0.22113 |
| Knee_KL_person_Pheno_P12111_CO6A3_EVQVFEITENSAK (49) | 0.03803 | 0.28928 | -0.0966 | 0.22546 |
| Knee_KL_person_Pheno_Q9NQ79_CRAC1_SSPYYALR (2) | 0.0889 | 0.37549 | -0.2157 | 0.32057 |
| Knee_KL_person_Pheno_Q9NQ79_CRAC1_GVASLFAGR (1) | 0.09367 | 0.3324 | -0.2277 | 0.30339 |
| Knee_KL_person_Pheno_P12259_FA5_SEAYNTFSER (61) | -0.0563 | 0.40341 | 0.14727 | 0.23078 |
| Knee_KL_person_Pheno_Q12805_FBLN3_ADQVCINLR (65) | 0.04385 | 0.35046 | -0.1311 | 0.30663 |
| Knee_KL_person_Pheno_Q15113_PCOC1_TGGLDLPSPPTGASLK (95) | 0.04197 | 0.27951 | -0.0952 | 0.28438 |
| Knee_KL_person_Pheno_P01033_TIMP1_GFQALGDAADIR (111) | 0.02734 | 0.33457 | -0.0504 | 0.17746 |
| Knee_KL_person_Pheno_P49747_COMP_SSTGPGEQLR (55) | -0.08 | 0.57743 | 0.21684 | 0.31976 |
| Knee_KL_person_Pheno_P35443_TSP4_DVDIDSYPDEELPCSAR (113) | 0.06604 | 0.47366 | -0.1577 | 0.34252 |

TABLE 2C-continued

| Diagnostic Data (OA = Osteoarthritis, C = Control) | | | | |
|---|---|---|---|---|
| Knee_KL_person_Pheno_Q12805_FBLN3_NPCQDPYILTPENR (64) | 0.04932 | 0.37969 | −0.1385 | 0.26628 |
| Knee_OST_person_Pheno_P06396_GELS_GGVASGFK (72) | 0.01502 | 0.24089 | −0.035 | 0.23657 |
| Knee_OST_person_Pheno_P08697_A2AP_SPPGVCSR (4) | 0.14605 | 0.57584 | −0.2877 | 0.39295 |
| Knee_OST_person_Pheno_P08697_A2AP_LCQDLGPGAFR (5) | −0.1351 | 0.70192 | 0.26055 | 0.27125 |
| Knee_OST_person_Pheno_P63261_ACTG_VAPEEHPVLLTEAPLNPK (11) | −3.0367 | 0.27282 | −2.9771 | 0.25759 |
| Knee_OST_person_Pheno_P02747_C1QC_VVTFCGHTSK (20) | 0.01463 | 0.89969 | 0.01413 | 0.78594 |
| Knee_OST_person_Pheno_P06681_CO2_SSGQWQTPGATR (41) | −0.1157 | 0.72985 | 0.2422 | 0.34386 |
| Knee_OST_person_Pheno_P01031_CO5_GIYGTISR (44) | −0.0524 | 0.42324 | 0.11753 | 0.24644 |
| Knee_OST_person_Pheno_P12111_CO6A3_EVQVFEITENSAK (49) | 0.04953 | 0.26305 | −0.1016 | 0.28306 |
| Knee_OST_person_Pheno_Q9NQ79_CRAC1_SSPYYALR (2) | 0.08684 | 0.38283 | −0.1715 | 0.33148 |
| Knee_OST_person_Pheno_Q9NQ79_CRAC1_GVASLFAGR (1) | 0.09341 | 0.33665 | −0.1849 | 0.31822 |
| Knee_OST_person_Pheno_P12259_FA5_SEAYNTFSER (61) | −0.067 | 0.40428 | 0.14172 | 0.25122 |
| Knee_OST_person_Pheno_Q12805_FBLN3_ADQVCINLR (65) | 0.04391 | 0.35403 | −0.1082 | 0.31055 |
| Knee_OST_person_Pheno_Q15113_PCOC1_TGGLDLPSPPTGASLK (95) | 0.03371 | 0.28161 | −0.0608 | 0.2897 |
| Knee_OST_person_Pheno_P05452_TETN_TFHEASEDCISR (107) | 0.01949 | 0.27559 | −0.0453 | 0.2601 |
| Knee_OST_person_Pheno_P49747_COMP_SSTGPGEQLR (55) | −0.0702 | 0.58158 | 0.15842 | 0.3793 |
| Knee_OST_person_Pheno_P35443_TSP4_DVDIDSYPDEELPCSAR (113) | 0.0712 | 0.47712 | −0.1384 | 0.35618 |
| Knee_OST_person_Pheno_Q12805_FBLN3_NPCQDPYILTPENR (64) | 0.046 | 0.3822 | −0.1073 | 0.28853 |
| ELISA markers; knee; GEE | | | | |
| Knee_JSN_Pheno_cd14_serum | 2575.92 | 697.218 | 2248.74 | 613.423 |
| Knee_JSN_Pheno_1HA_serum | 5.71988 | 0.85584 | 5.11415 | 0.75264 |
| Knee_JSN_Pheno_cerulo_urine_urine1 | 0.5915 | 0.79293 | 1.01494 | 0.92315 |
| Knee_JSN_Pheno_kinno_serum | 294.282 | 121.894 | 399.274 | 235.284 |
| Knee_JSN_Pheno_cerulo_urine_urine2 | −8.792 | 1.27149 | −8.0153 | 1.54441 |
| Knee_JSN_Pheno_hapto_serum | 1333.67 | 757.365 | 1072.78 | 642.54 |
| Knee_JSN_Pheno_ctx1a_ctx_1b_urine2 | −15.333 | 2.20557 | −14.262 | 2.50326 |
| Knee_JSN_Pheno_ctx1a_ctx1b_urine1 | −5.9539 | 1.36704 | −5.2837 | 1.54433 |
| Knee_JSN_Pheno_vitd_binding_serum | 939.199 | 593.361 | 1196.78 | 705.038 |
| Knee_KL_Pheno_kinno_serum | 295.263 | 119.804 | 441.7 | 259.637 |
| Knee_KL_Pheno_cd14_serum | 2546.19 | 715.028 | 2169.76 | 514.811 |

TABLE 2C-continued

| Diagnostic Data (OA = Osteoarthritis, C = Control) | | | | |
|---|---|---|---|---|
| Knee_KL_Pheno_1HA_serum | 5.63111 | 0.81308 | 5.01795 | 0.7993 |
| Knee_KL_Pheno_cerulo_urine_urine2 | −8.6707 | 1.29058 | −7.9629 | 1.63572 |
| Knee_KL_Pheno_ctx1a_ctx_1b_urine2 | −15.234 | 2.22103 | −14.065 | 2.56318 |
| Knee_KL_Pheno_ctx1a_ctx_1b_urine1 | −5.8997 | 1.38261 | −5.1219 | 1.56123 |
| Knee_KL_Pheno_vitd_binding_serum | 960.501 | 602.213 | 1263.09 | 725.301 |
| Knee_OST_Pheno_kinno_serum | 287.479 | 113.997 | 436.257 | 249.333 |
| Knee_OST_Pheno_cerulo_urine_urine2 | −8.6634 | 1.28494 | −8.0895 | 1.61516 |
| Knee_OST_Pheno_1HA_serum | 5.61496 | 0.81508 | 5.11291 | 0.83713 |
| Knee_OST_Pheno_ctx1a_ctx1b_urine2 | −15.23 | 2.21429 | −14.263 | 2.55727 |
| Knee_OST_Pheno_ctx1a_ctx1b_urine1 | −5.9052 | 1.38361 | −5.2423 | 1.55556 |
| Knee_OST_Pheno_cd14_serum | 2525.14 | 699.29 | 2262.88 | 613.837 |
| Knee_OST_Pheno_ctx2_urine1 | −5.0633 | 0.67926 | −5.3241 | 0.66827 |
| Knee_OST_Pheno_vitd_binding_serum | 969.878 | 616.484 | 1204.18 | 702.73 |
| ELISA markers; knee; person | | | | |
| Knee_JSN_person_Pheno_cd14_serum | 2602.29 | 697.192 | 2162.75 | 564.587 |
| Knee_JSN_person_Pheno_cerulo_urine_urine1 | 0.57459 | 0.78943 | 1.10486 | 0.92437 |
| Knee_JSN_person_Pheno_cerulo_urine_urine2 | −8.8113 | 1.25771 | −7.8761 | 1.56237 |
| Knee_JSN_person_Pheno_1HA_serum | 5.69895 | 0.82885 | 5.06371 | 0.77171 |
| Knee_JSN_person_Pheno_kinno_serum | 294.293 | 122.788 | 412.385 | 243.775 |
| Knee_JSN_person_Pheno_ctx1a_ctx1b_urine2 | −15.324 | 2.21534 | −14.121 | 2.52557 |
| Knee_JSN_person_Pheno_ctxi_urine2 | −12.991 | 1.55032 | −12.262 | 1.85502 |
| Knee_JSN_person_Pheno_ctx1a_ctx1b_urine1 | −5.9456 | 1.37228 | −5.1932 | 1.55878 |
| Knee_JSN_person_Pheno_ctxi_urine1 | −3.613 | 0.77049 | −3.2866 | 0.82608 |
| Knee_JSN_person_Pheno_vitd_binding_serum | 946.698 | 594.172 | 1224.92 | 721.843 |
| Knee_KL_person_Pheno_kinno_serum | 296.711 | 124.85 | 455.818 | 265.551 |
| Knee_KL_person_Pheno_cd14_serum | 2530.04 | 710.539 | 2149.83 | 508.765 |
| Knee_KL_person_Pheno_1HA_serum | 5.61727 | 0.80017 | 4.97511 | 0.83057 |
| Knee_KL_person_Pheno_cerulo_urine_urine2 | −8.6167 | 1.33156 | −7.9782 | 1.65722 |
| Knee_KL_person_Pheno_vitd_binding_serum | 981.978 | 620.479 | 1258.48 | 725.875 |
| Knee_KL_person_Pheno_ctx1a_ctx1b_urine1 | −5.8193 | 1.4108 | −5.1917 | 1.60826 |
| Knee_OST_person_Pheno_kinno_serum | 291.557 | 123.07 | 452.669 | 256.211 |
| Knee_OST_person_Pheno_cd14_serum | 2520.46 | 709.306 | 2223.94 | 573.96 |
| Knee_OST_person_Pheno_1HA_serum | 5.601 | 0.79819 | 5.05754 | 0.87099 |
| Knee_OST_person_Pheno_ctx1a_ctx1b_urine1 | −5.8403 | 1.42891 | −5.2499 | 1.55116 |

TABLE 2D

| Prognostic Data (P = Progressor, NP = non-Progressor) | | | | |
|---|---|---|---|---|
| Prognostic Data | | | | |
| Phenotype (SEQ ID NO: X) | Pmean | Psd | NPmean | NPsd |
| MRM markers; nondepleted serum; knee; GEE | | | | |
| Knee_JSN_Pheno_P08603_CFAH_CLPVTAPENGK (35) | −1.8733 | 0.18394 | −1.9774 | 0.25529 |
| Knee_JSN_Pheno_P02749_APOH_ATFGCHDGYSLDGPEEIECTK (18) | 0.21648 | 0.18367 | 0.10653 | 0.27925 |
| Knee_JSN_Pheno_P04196_HRG_YWNDCEPPDSR (81) | −2.3987 | 0.25856 | −2.4794 | 0.35586 |
| Knee_JSN_Pheno_P01011_AACT_NLAVSQVVHK (9) | 0.06855 | 0.2493 | −0.0534 | 0.25394 |
| Knee_JSN_Pheno_P01011_AACT_ADLSGITGAR (8) | 0.00169 | 0.23843 | −0.1136 | 0.23088 |
| Knee_JSN_Pheno_P02753_RET4_LIVHNGYCDGR (103) | −1.328 | 0.26527 | −1.4141 | 0.29284 |
| Knee_JSN_Pheno_P02743_SAMP_AYSDLSR (104) | −1.1083 | 0.2406 | −1.2255 | 0.26865 |
| Knee_JSN_Pheno_P00734_THRB_NPDSSTTGPWCYTTDPTVR (110) | −1.2674 | 0.3453 | −1.399 | 0.36795 |
| Knee_JSN_Pheno_P01011_AACT_EQLSLLDR (10) | 0.64266 | 0.24252 | 0.52223 | 0.25274 |
| Knee_JSN_Pheno_Q14624_ITIH4_FKPTLSQQQK (86) | −1.1111 | 0.21404 | −1.1857 | 0.24724 |
| Knee_JSN_Pheno_P07996_TSP1_FVFGTTPEDILR (112) | −3.8418 | 0.26133 | −3.9693 | 0.37682 |
| Knee_JSN_Pheno_P16112_PGCA_VSLPNYPAIPSDATLEVQSLR (96) | −8.3507 | 0.5464 | −8.6397 | 0.6233 |
| Knee_KL_Pheno_P08603_CFAH_CLPVTAPENGK (35) | −1.8514 | 0.15151 | −1.9889 | 0.26845 |
| Knee_KL_Pheno_P80108_PHLD_FGSSLITVR (98) | −3.8693 | 0.223 | −3.9931 | 0.33846 |
| Knee_KL_Pheno_P02743_SAMP_AYSDLSR (104) | −1.0849 | 0.2601 | −1.2417 | 0.27982 |
| Knee_KL_Pheno_P01031_CO5_TLLPVSKPER (45) | −2.5743 | 0.17657 | −2.6595 | 0.21099 |
| Knee_KL_Pheno_P01031_CO5_GIYGTISR (44) | −2.586 | 0.17701 | −2.6822 | 0.22119 |
| Knee_KL_Pheno_P04003_C4BPA_GVGWSHPLPQCEIVK (26) | −0.6009 | 0.26167 | −0.7042 | 0.35265 |
| Knee_KL_Pheno_P02753_RET4_LIVHNGYCDGR (103) | −1.318 | 0.28743 | −1.405 | 0.27131 |
| Knee_KL_Pheno_P02749_APOH_ATFGCHDGYSLDGPEEIECTK (18) | 0.21968 | 0.20833 | 0.12004 | 0.27085 |
| Knee_KL_Pheno_P07996_TSP1_FVFGTTPEDILR (112) | −3.818 | 0.24999 | −4.0312 | 0.51382 |
| Knee_KL_Pheno_P02765_FETUA_FSVVYAK (69) | 0.47776 | 0.1871 | 0.42755 | 0.18126 |
| Knee_KL_Pheno_P00734_THRB_NPDSSTTGPWCYTTDPTVR (110) | −1.2604 | 0.36827 | −1.4032 | 0.36302 |
| Knee_KL_Pheno_P00736_C1R_GLTLHLK (22) | −1.5768 | 0.17668 | −1.6834 | 0.23557 |

TABLE 2D-continued

Prognostic Data (P = Progressor, NP = non-Progressor)

| | | | | |
|---|---|---|---|---|
| Knee_KL_Pheno_P01011_AACT_NLAVSQVVHK (9) | 0.09174 | 0.25744 | −0.0404 | 0.25316 |
| Knee_KL_Pheno_P00736_C1R_GYGFYTK (23) | −2.4711 | 0.1838 | −2.5691 | 0.21992 |
| Knee_KL_Pheno_P09871_C1S_LLEVPEGR (39) | −2.3873 | 0.16142 | −2.4663 | 0.17408 |
| Knee_KL_Pheno_P04114_APOB_LAIPEGK (15) | −1.1379 | 0.23634 | −1.2751 | 0.2705 |
| Knee_KL_Pheno_P01011_AACT_ADLSGITGAR (8) | 0.0238 | 0.24725 | −0.0937 | 0.22724 |
| Knee_KL_Pheno_P05546_HEP2_NFGYTLR (76) | −0.3486 | 0.23541 | −0.4828 | 0.22968 |
| Knee_KL_Pheno_P05156_CFAI_HGNTDSEGIVEVK (36) | −2.0777 | 0.19407 | −2.1776 | 0.26138 |
| Knee_KL_Pheno_P02751_FINC_EYLGAICSCTCFGGQR (70) | −1.5794 | 0.37426 | −1.7745 | 0.50563 |
| Knee_KL_Pheno_P02751_FINC_IGDTWSK (71) | −1.9724 | 0.28416 | −2.1392 | 0.44287 |
| Knee_OST_Pheno_P02776_PLF4_ICLDLQAPLYK (99) | −2.6274 | 0.32402 | −2.8927 | 0.54107 |
| Knee_OST_Pheno_P01011_AACT_EQLSLLDR (10) | 0.63078 | 0.24078 | 0.5271 | 0.24313 |
| Knee_OST_Pheno_P01011_AACT_ADLSGITGAR (8) | −0.0125 | 0.22315 | −0.1117 | 0.22687 |
| Knee_OST_Pheno_P01008_ANT3_ATEDEGSEQK (14) | 5.43145 | 0.39014 | 5.62562 | 0.4794 |
| Knee_OST_Pheno_P01011_AACT_NLAVSQVVHK (9) | 0.04359 | 0.24761 | −0.0522 | 0.24691 |
| Knee_OST_Pheno_P02775_CXCL7_NIQSLEVIGK (57) | −1.5495 | 0.28583 | −1.7827 | 0.54969 |
| Knee_OST_Pheno_Q9NQ79_CRAC1_SSPYYALR (2) | −5.2482 | 0.31894 | −5.3319 | 0.29197 |
| Knee_OST_Pheno_Q14624_ITIH4_FKPTLSQQQK (86) | −1.1228 | 0.21444 | −1.2061 | 0.25212 |
| Knee_OST_Pheno_P00747_PLMN_HSIFTPETNPR (100) | −0.9833 | 0.22029 | −1.0623 | 0.23109 |
| Knee_OST_Pheno_P07996_TSP1_FVFGTTPEDILR (112) | −3.8992 | 0.3198 | −4.0688 | 0.58725 |
| Knee_OST_Pheno_P01031_CO5_GIYGTISR (44) | −2.6246 | 0.18727 | −2.6943 | 0.23962 |
| Knee_OST_Pheno_P00734_THRB_NPDSSTTGPWCYTTDPTVR (110) | −1.3017 | 0.35587 | −1.4473 | 0.37127 |
| Knee_OST_Pheno_P04003_C4BPA_GVGWSHPLPQCEIVK (26) | −0.6339 | 0.29939 | −0.7455 | 0.37048 |

MRM markers; nondepleted serum; knee; person

| | | | | |
|---|---|---|---|---|
| Knee_JSN_person_Pheno_P04196_HRG_YWNDCEPPDSR (81) | −2.3884 | 0.28937 | −2.5389 | 0.3736 |
| Knee_JSN_person_Pheno_P08603_CFAH_CLPVTAPENGK (35) | −1.8864 | 0.19324 | −2.0163 | 0.29792 |
| Knee_JSN_person_Pheno_P00734_THRB_NPDSSTTGPWCYTTDPTVR (110) | −1.2579 | 0.34881 | −1.4555 | 0.39541 |

TABLE 2D-continued

| Prognostic Data (P = Progressor, NP = non-Progressor) | | | | |
|---|---|---|---|---|
| Knee_JSN_person_Pheno_P02749_APOH_ ATFGCHDGYSLDGPEEIECTK (18) | 0.21115 | 0.20133 | 0.09183 | 0.30327 |
| Knee_JSN_person_Pheno_P07996_TSP1_F VFGTTPEDILR (112) | −3.8365 | 0.27116 | −4.0282 | 0.40996 |
| Knee_JSN_person_Pheno_P01011_AACT_ ADLSGITGAR (8) | −0.0089 | 0.24667 | −0.1122 | 0.22344 |
| Knee_KL_person_Pheno_P08603_CFAH_ CLPVTAPENGK (35) | −1.8612 | 0.15652 | −2.0084 | 0.27151 |
| Knee_KL_person_Pheno_P04003_C4BPA_ GVGWSHPLPQCEIVK (26) | −0.5958 | 0.26047 | −0.7189 | 0.35023 |
| Knee_KL_person_Pheno_P00734_THRB_ NPDSSTTGPWCYTTDPTVR (110) | −1.2649 | 0.35943 | −1.4086 | 0.36133 |
| Knee_KL_person_Pheno_P02743_SAMP_ AYSDLSR (104) | −1.0876 | 0.27091 | −1.2492 | 0.26573 |
| Knee_KL_person_Pheno_P07996_TSP1_F VFGTTPEDILR (112) | −3.8132 | 0.25135 | −4.0374 | 0.51953 |
| Knee_KL_person_Pheno_P01033_TIMP1_ GFQALGDAADIR (111) | −5.4698 | 0.473 | −5.666 | 0.36542 |
| Knee_KL_person_Pheno_P01011_AACT_ NLAVSQVVHK (9) | 0.0924 | 0.26356 | −0.0471 | 0.24199 |
| Knee_KL_person_Pheno_P01011_AACT_ ADLSGITGAR (8) | 0.02557 | 0.24965 | −0.1008 | 0.21807 |
| Knee_KL_person_Pheno_P00736_C1R_GL TLHLK (22) | −1.5842 | 0.19482 | −1.6865 | 0.22542 |
| Knee_KL_person_Pheno_P00736_C1R_GY GFYTK (23) | −2.474 | 0.19643 | −2.572 | 0.20978 |
| Knee_KL_person_Pheno_P04114_APOB_L AIPEGK (15) | −1.1494 | 0.23247 | −1.2804 | 0.26849 |
| Knee_KL_person_Pheno_P01011_AACT_ EQLSLLDR (10) | 0.662 | 0.25482 | 0.54442 | 0.24088 |
| Knee_KL_person_Pheno_P05546_HEP2_F TVDRPFLFLIYEHR (77) | −1.0844 | 0.30497 | −1.2083 | 0.25962 |
| Knee_KL_person_Pheno_P05546_HEP2_N FGYTLR (76) | −0.3694 | 0.24506 | −0.4742 | 0.2235 |
| Knee_OST_person_Pheno_P02776_PLF4_I CLDLQAPLYK (99) | −2.6369 | 0.35736 | −2.9409 | 0.55151 |
| Knee_OST_person_Pheno_P02775_CXCL7_ NIQSLEVIGK (57) | −1.556 | 0.31036 | −1.8293 | 0.58207 |
| Knee_OST_person_Pheno_P07358_CO8B_ GILNEIK (51) | −4.2578 | 0.31545 | −4.5185 | 0.43523 |
| Knee_OST_person_Pheno_P01008_ANT3_ ATEDEGSEQK (14) | 5.44905 | 0.40304 | 5.69097 | 0.46458 |
| Knee_OST_person_Pheno_P02751_FINC_ EYLGAICSCTCFGGQR (70) | −1.6448 | 0.41689 | −1.8881 | 0.56808 |
| Knee_OST_person_Pheno_P02751_FINC_I GDTWSK (71) | −2.0429 | 0.42336 | −2.2089 | 0.36074 |
| Knee_OST_person_Pheno_P07996_TSP1_ FVFGTTPEDILR (112) | −3.8963 | 0.33583 | −4.1239 | 0.64185 |
| Knee_OST_person_Pheno_P07360_CO8G_ QLYGDTGVLGR (52) | −4.6125 | 0.3262 | −4.7935 | 0.43203 |
| Knee_OST_person_Pheno_Q92954_PRG4_ DQYYNIDVPSR (102) | −4.4216 | 0.33795 | −4.6091 | 0.37538 |

TABLE 2D-continued

| Prognostic Data (P = Progressor, NP = non-Progressor) | | | | |
|---|---|---|---|---|
| Knee_OST_person_Pheno_Q92954_PRG4_ITEVWGIPSPIDTVFTR (101) | −4.087 | 0.38455 | −4.3242 | 0.46606 |
| Knee_OST_person_Pheno_P03952_KLKB1_VSEGNHDIALIK (87) | −1.9461 | 0.24557 | −2.097 | 0.31923 |
| Knee_OST_person_Pheno_P04196_HRG_YWNDCEPPDSR (81) | −2.4096 | 0.26503 | −2.5521 | 0.35484 |
| Knee_OST_person_Pheno_P08603_CFAH_CLPVTAPENGK (35) | −1.9136 | 0.21584 | −2.0406 | 0.29389 |
| Knee_OST_person_Pheno_P04003_C4BPA_GVGWSHPLPQCEIVK (26) | −0.6346 | 0.32245 | −0.804 | 0.33093 |
| Knee_OST_person_Pheno_P06681_CO2_DGNDHSLWR (42) | −3.1113 | 0.23486 | −3.2284 | 0.23677 |
| ELISA markers; knee; GEE | | | | |
| Knee_JSN_Pheno_hapto_serum | 1606.88 | 817.954 | 1107.57 | 624.568 |
| Knee_JSN_Pheno_cd44_serum | 150.65 | 27.9062 | 167.947 | 45.6712 |
| Knee_JSN_Pheno_hemopexin_serum | 1550.7 | 222.741 | 1419.74 | 270.341 |
| Knee_JSN_Pheno_cd163_serum | 821.961 | 284.381 | 881.345 | 302.904 |
| Knee_JSN_Pheno_vitd_binding_serum | 809.959 | 554.359 | 1047.53 | 607.144 |
| Knee_JSN_Pheno_lcerulo_serum | 6.58372 | 0.6484 | 6.80215 | 0.64846 |
| Knee_JSN_Pheno_1HA_serum | 5.63002 | 0.93682 | 5.79114 | 0.78678 |
| Knee_JSN_Pheno_tbg_serum | 15.2226 | 5.21314 | 16.5391 | 4.14235 |
| Knee_JSN_Pheno_ctx_lbeta_urine1 | −3.0961 | 0.84019 | −3.2716 | 0.86223 |
| Knee_JSN_Pheno_ctx1a_ctx1b_urine1 | −6.0929 | 1.3862 | −5.8491 | 1.3537 |
| Knee_JSN_Pheno_cd14_serum | 2581.92 | 660.618 | 2571.06 | 730.345 |
| Knee_JSN_Pheno_comp_serum | 1624.31 | 586.104 | 1666.57 | 614.388 |
| Knee_JSN_Pheno_hapto_urine_urine1 | −1.8209 | 1.93942 | −2.104 | 1.75651 |
| Knee_JSN_Pheno_hapto_urine_urine2 | −11.306 | 2.02314 | −11.512 | 1.87493 |
| Knee_JSN_Pheno_ctx1a_ctx1b_urine2 | −15.535 | 2.27897 | −15.179 | 2.15288 |
| Knee_JSN_Pheno_ctx_lbeta_urine2 | −12.538 | 1.23799 | −12.603 | 1.30309 |
| Knee_JSN_Pheno_ctx2_urine1 | −5.007 | 0.89173 | −5.1513 | 0.59994 |
| Knee_JSN_Pheno_ctx2_urine2 | −14.449 | 1.04709 | −14.485 | 1.13908 |
| Knee_JSN_Pheno_ctxi_urine1 | −3.6442 | 0.78839 | −3.5905 | 0.75005 |
| Knee_JSN_Pheno_ctxi_urine2 | −13.087 | 1.59755 | −12.921 | 1.54536 |
| Knee_JSN_Pheno_coll3_serum | 23.7345 | 3.40834 | 23.5759 | 3.41947 |
| Knee_JSN_Pheno_cerulo_urine_urine2 | −8.767 | 1.30124 | −8.8112 | 1.25825 |
| Knee_JSN_Pheno_kinno_serum | 290.915 | 142.942 | 297.069 | 102.493 |
| Knee_JSN_Pheno_cerulo_urine_urine1 | 0.67532 | 0.8622 | 0.52831 | 0.73697 |
| Knee_KL_Pheno_lcerulo_serum_serum | 6.51632 | 0.69437 | 6.87555 | 0.60683 |
| Knee_KL_Pheno_hapto_serum | 1579.83 | 865.189 | 1144.89 | 625.329 |
| Knee_KL_Pheno_cd44_serum | 155.42 | 35.625 | 167.649 | 42.8249 |
| Knee_KL_Pheno_hapto_urine_urine2 | −10.901 | 2.05767 | −11.662 | 1.90504 |
| Knee_KL_Pheno_vitd_binding_serum | 905.41 | 563.381 | 983.619 | 618.757 |

TABLE 2D-continued

| Prognostic Data (P = Progressor, NP = non-Progressor) | | | | |
|---|---|---|---|---|
| Knee_KL_Pheno_ctx_lbeta_urine2 | −12.416 | 1.4272 | −12.628 | 1.20552 |
| Knee_KL_Pheno_ctx2_urine1 | −5.2374 | 0.91413 | −5.0238 | 0.64339 |
| Knee_KL_Pheno_tbg_serum | 16.1841 | 4.51185 | 16.4486 | 4.63061 |
| Knee_KL_Pheno_cd14_serum | 2661.92 | 691.486 | 2499.09 | 722.077 |
| Knee_KL_Pheno_ctx1a_ctx1b_urine2 | −14.695 | 2.6064 | −15.428 | 2.04488 |
| Knee_KL_Pheno_ctxi_urine2 | −12.666 | 1.85633 | −13.046 | 1.42449 |
| Knee_KL_Pheno_cerulo_urine_urine1 | 0.73544 | 0.86068 | 0.67915 | 0.82822 |
| Knee_KL_Pheno_hapto_urine_urine1 | −1.7817 | 1.86541 | −2.1445 | 1.86244 |
| Knee_KL_Pheno_ctx2_urine2 | −14.334 | 1.12639 | −14.478 | 1.10132 |
| Knee_KL_Pheno_cerulo_urine_urine2 | −8.3612 | 1.43515 | −8.7819 | 1.22296 |
| Knee_KL_Pheno_cd163_serum | 890.667 | 308.31 | 827.306 | 270.548 |
| Knee_KL_Pheno_comp_serum | 1805.5 | 696.916 | 1603.06 | 549.065 |
| Knee_KL_Pheno_kinno_serum | 306.848 | 150.277 | 290.86 | 106.542 |
| Knee_KL_Pheno_1HA_serum | 5.59659 | 0.86984 | 5.64353 | 0.79587 |
| Knee_KL_Pheno_hemopexin_serum | 1589.28 | 253.919 | 1477.24 | 372.807 |
| Knee_KL_Pheno_ctx1a_ctx1b_urine1 | −5.6508 | 1.58585 | −5.9889 | 1.29875 |
| Knee_KL_Pheno_coll3_serum | 24.4897 | 3.53911 | 23.6109 | 3.59543 |
| Knee_KL_Pheno_ctxi_urine1 | −3.5684 | 0.91432 | −3.5921 | 0.69628 |
| Knee_KL_Pheno_ctx_lbeta_urine1 | −3.2978 | 0.91008 | −3.169 | 0.85943 |
| Knee_OST_Pheno_1HA_serum | 5.47246 | 0.88898 | 5.76204 | 0.70844 |
| Knee_OST_Pheno_hapto_serum | 1386.54 | 779.479 | 1103.49 | 611.724 |
| Knee_OST_Pheno_cd163_serum | 794.197 | 276.997 | 892.772 | 285.564 |
| Knee_OST_Pheno_cd44_serum | 158.26 | 37.0897 | 172.328 | 44.3459 |
| Knee_OST_Pheno_tbg_serum | 15.7036 | 5.16053 | 16.9976 | 4.04741 |
| Knee_OST_Pheno_cerulo_urine_urine2 | −8.8172 | 1.30041 | −8.5072 | 1.26027 |
| Knee_OST_Pheno_ctx1a_ctx1b_urine1 | −6.0859 | 1.30181 | −5.7273 | 1.44766 |
| Knee_OST_Pheno_ctxi_urine1 | −3.6674 | 0.79932 | −3.5154 | 0.72453 |
| Knee_OST_Pheno_comp_serum | 1565.03 | 476.409 | 1736.8 | 679.457 |
| Knee_OST_Pheno_hemopexin_serum | 1546.7 | 357.536 | 1481.31 | 359.671 |
| Knee_OST_Pheno_ctx1a_ctx1b_urine2 | −15.493 | 2.15187 | −14.962 | 2.26187 |
| Knee_OST_Pheno_ctxi_urine2 | −13.101 | 1.60025 | −12.784 | 1.49467 |
| Knee_OST_Pheno_cerulo_urine_urine1 | 0.61404 | 0.8256 | 0.77457 | 0.8674 |
| Knee_OST_Pheno_vitd_binding_serum | 1004.24 | 643.216 | 934.067 | 589.759 |
| Knee_OST_Pheno_cd14_serum | 2535.59 | 667.835 | 2514.55 | 734.427 |
| Knee_OST_Pheno_ctx_lbeta_urine2 | −12.619 | 1.34067 | −12.536 | 1.23706 |
| Knee_OST_Pheno_ctx2_urine2 | −14.451 | 1.0706 | −14.383 | 1.10635 |
| Knee_OST_Pheno_kinno_serum | 291.233 | 113.953 | 283.484 | 114.836 |
| Knee_OST_Pheno_hapto_urine_urine2 | −11.556 | 2.16059 | −11.38 | 1.86644 |
| Knee_OST_Pheno_ctx2_urine1 | −5.0195 | 0.72808 | −5.1065 | 0.63031 |

TABLE 2D-continued

Prognostic Data (P = Progressor, NP = non-Progressor)

| | | | | |
|---|---|---|---|---|
| Knee_OST_Pheno_lcerulo_serum | 6.75596 | 0.61035 | 6.83172 | 0.67827 |
| Knee_OST_Pheno_hapto_urine_urine1 | −2.0969 | 1.86438 | −2.0368 | 1.86182 |
| Knee_OST_Pheno_coll3_serum | 23.707 | 3.64127 | 24.2162 | 3.52646 |
| Knee_OST_Pheno_ctx_1beta_urine1 | −3.177 | 0.88927 | −3.2504 | 0.90828 |

ELISA markers; knee; person

| | | | | |
|---|---|---|---|---|
| Knee_JSN_person_Pheno_hapto_serum | 1603.35 | 829.077 | 996.543 | 480.362 |
| Knee_JSN_person_Pheno_cd44_serum | 152.974 | 28.6622 | 171.635 | 47.738 |
| Knee_JSN_person_Pheno_lcerulo_serum_serum | 6.55994 | 0.64513 | 6.88947 | 0.63355 |
| Knee_JSN_person_Pheno_vitd_binding_serum | 824.727 | 563.488 | 1075.84 | 606.629 |
| Knee_JSN_person_Pheno_hemopexin_serum | 1529.95 | 229.779 | 1415.63 | 301.975 |
| Knee_JSN_person_Pheno_cd163_serum | 814.817 | 288.557 | 887.965 | 320.78 |
| Knee_JSN_person_Pheno_tbg_serum | 15.2671 | 4.85939 | 16.9759 | 4.25425 |
| Knee_JSN_person_Pheno_hapto_urine_urine1 | −1.6798 | 1.87231 | −2.2666 | 1.73415 |
| Knee_JSN_person_Pheno_hapto_urine_urine2 | −11.113 | 1.984 | −11.68 | 1.81184 |
| Knee_JSN_person_Pheno_1HA_serum | 5.61905 | 0.89867 | 5.78457 | 0.75377 |
| Knee_JSN_person_Pheno_cd14_serum | 2642.04 | 662.952 | 2560.2 | 739.359 |
| Knee_JSN_person_Pheno_ctx2_urine1 | −4.9732 | 0.82227 | −5.2162 | 0.63565 |
| Knee_JSN_person_Pheno_ctx_1beta_urine1 | −3.0907 | 0.88169 | −3.313 | 0.90923 |
| Knee_JSN_person_Pheno_ctx2_urine2 | −14.351 | 1.11176 | −14.602 | 1.10084 |
| Knee_JSN_person_Pheno_ctx_1beta_urine2 | −12.469 | 1.28896 | −12.694 | 1.26058 |
| Knee_JSN_person_Pheno_cerulo_urine_urine1 | 0.6837 | 0.90088 | 0.46547 | 0.656 |
| Knee_JSN_person_Pheno_cerulo_urine_urine2 | −8.6944 | 1.39072 | −8.9319 | 1.11398 |
| Knee_JSN_person_Pheno_ctx1a_ctx1b_urine1 | −6.0306 | 1.43529 | −5.8607 | 1.32367 |
| Knee_JSN_person_Pheno_ctxi_urine2 | −13.005 | 1.6566 | −12.977 | 1.4598 |
| Knee_JSN_person_Pheno_comp_serum | 1679.54 | 599.743 | 1633.04 | 649.199 |
| Knee_JSN_person_Pheno_ctx1a_ctx1b_urine2 | −15.409 | 2.3739 | −15.236 | 2.07455 |
| Knee_JSN_person_Pheno_ctxi_urine1 | −3.6268 | 0.81623 | −3.5992 | 0.73473 |
| Knee_JSN_person_Pheno_coll3_serum | 23.6763 | 3.52326 | 23.7218 | 3.58698 |
| Knee_JSN_person_Pheno_kinno_serum | 291.262 | 138.289 | 297.648 | 105.434 |
| Knee_KL_person_Pheno_hapto_serum | 1600.51 | 862.418 | 1130.33 | 601.341 |
| Knee_KL_person_Pheno_lcerulo_serum_serum | 6.58129 | 0.69665 | 6.87527 | 0.62344 |
| Knee_KL_person_Pheno_vitd_binding_serum | 863.701 | 542.634 | 1040.08 | 651.991 |
| Knee_KL_person_Pheno_cd44_serum | 157.132 | 40.4298 | 167.18 | 40.7173 |

TABLE 2D-continued

Prognostic Data (P = Progressor, NP = non-Progressor)

| | | | | |
|---|---|---|---|---|
| Knee_KL_person_Pheno_hapto_urine_urine2 | −10.809 | 2.00864 | −11.637 | 1.93665 |
| Knee_KL_person_Pheno_ctx_1beta_urine2 | −12.378 | 1.37454 | −12.639 | 1.23375 |
| Knee_KL_person_Pheno_tbg_serum | 16.0036 | 4.84965 | 16.8026 | 4.64742 |
| Knee_KL_person_Pheno_cd14_serum | 2636.39 | 682.689 | 2477.81 | 723.986 |
| Knee_KL_person_Pheno_hapto_urine_urine1 | −1.6427 | 1.80641 | −2.1936 | 1.86267 |
| Knee_KL_person_Pheno_cd163_serum | 863.405 | 311.188 | 828.269 | 274.802 |
| Knee_KL_person_Pheno_ctxi_urine2 | −12.642 | 1.7623 | −12.988 | 1.4886 |
| Knee_KL_person_Pheno_ctx1a_ctx1b_urine2 | −14.701 | 2.49009 | −15.301 | 2.14653 |
| Knee_KL_person_Pheno_ctx2_urine2 | −14.272 | 1.10587 | −14.488 | 1.16679 |
| Knee_KL_person_Pheno_cerulo_urine_urine2 | −8.3301 | 1.46313 | −8.7435 | 1.26323 |
| Knee_KL_person_Pheno_comp_serum | 1794.71 | 730.993 | 1613.72 | 541.515 |
| Knee_KL_person_Pheno_ctx2_urine1 | −5.1635 | 0.88338 | −5.0676 | 0.67814 |
| Knee_KL_person_Pheno_cerulo_urine_urine1 | 0.77872 | 0.94037 | 0.68227 | 0.79315 |
| Knee_KL_person_Pheno_hemopexin_serum | 1563.53 | 274.345 | 1474.19 | 372.59 |
| Knee_KL_person_Pheno_ctx1beta_urine1 | −3.2369 | 0.88412 | −3.2204 | 0.87136 |
| Knee_KL_person_Pheno_coll3_serum | 24.4696 | 3.42393 | 23.524 | 3.72776 |
| Knee_KL_person_Pheno_kinno_serum | 300.616 | 147.734 | 295.027 | 115.194 |
| Knee_KL_person_Pheno_ctx1a_ctx1b_urine1 | −5.6758 | 1.5659 | −5.8843 | 1.34559 |
| Knee_KL_person_Pheno_1HA_serum | 5.66124 | 0.89792 | 5.59917 | 0.76519 |
| Knee_KL_person_Pheno_ctxi_urine1 | −3.5329 | 0.8692 | −3.5709 | 0.72404 |
| Knee_OST_person_Pheno_hapto_serum | 1322.97 | 762.45 | 1107.02 | 566.902 |
| Knee_OST_person_Pheno_ctxi_urine1 | −3.658 | 0.80638 | −3.393 | 0.69443 |
| Knee_OST_person_Pheno_hemopexin_serum | 1550.32 | 394.039 | 1417.66 | 240.545 |
| Knee_OST_person_Pheno_ctx1a_ctx1b_urine1 | −6.0124 | 1.35475 | −5.5033 | 1.53767 |
| Knee_OST_person_Pheno_tbg_serum | 16.1968 | 4.99907 | 17.3638 | 4.31623 |
| Knee_OST_person_Pheno_ctxi_urine2 | −13.038 | 1.6066 | −12.509 | 1.54218 |
| Knee_OST_person_Pheno_cerulo_urine_urine2 | −8.754 | 1.31091 | −8.2981 | 1.39088 |
| Knee_OST_person_Pheno_ctx1a_ctx1b_urine2 | −15.355 | 2.20092 | −14.61 | 2.43526 |
| Knee_OST_person_Pheno_comp_serum | 1590.05 | 483.543 | 1772.73 | 757.186 |
| Knee_OST_person_Pheno_ctx_1beta_urine2 | −12.637 | 1.33736 | −12.307 | 1.18124 |
| Knee_OST_person_Pheno_cd14_serum | 2592.97 | 695.535 | 2380.79 | 727.765 |
| Knee_OST_person_Pheno_cerulo_urine_urine1 | 0.62306 | 0.85367 | 0.83754 | 0.8564 |
| Knee_OST_person_Pheno_ctx2_urine2 | −14.458 | 1.06195 | −14.214 | 1.25659 |

TABLE 2D-continued

| Prognostic Data (P = Progressor, NP = non-Progressor) | | | | |
|---|---|---|---|---|
| Knee_OST_person_Pheno_1HA_serum | 5.56184 | 0.86152 | 5.67931 | 0.66442 |
| Knee_OST_person_Pheno_kinno_serum | 301.275 | 116.42 | 271.699 | 136.201 |
| Knee_OST_person_Pheno_vitd_binding_serum | 1018.49 | 635.383 | 918.883 | 609.159 |
| Knee_OST_person_Pheno_coll3_serum | 23.8769 | 3.69506 | 23.7534 | 3.49101 |
| Knee_OST_person_Pheno_cd44_serum | 161.529 | 39.9551 | 167.546 | 43.4789 |
| Knee_OST_person_Pheno_cd163_serum | 834.289 | 292.216 | 837.768 | 287.367 |
| Knee_OST_person_Pheno_ctx_1beta_urine1 | −3.2442 | 0.9187 | −3.183 | 0.81553 |
| Knee_OST_person_Pheno_hapto_urine_une2 | −11.442 | 2.13675 | −11.4 | 1.75876 |
| Knee_OST_person_Pheno_hapto_urine_une1 | −2.0095 | 1.86826 | −2.2442 | 1.8478 |
| Knee_OST_person_Pheno_lcerulo_serum_serum | 6.78475 | 0.6028 | 6.76521 | 0.72645 |
| Knee_OST_person_Pheno_ctx2_urine1 | −5.0812 | 0.75831 | −5.0836 | 0.7278 |

2a. Non-Depleted Serum Proteomics (Analysis Using Calculated Ratios)

2a.1. Progression Analysis

The most significant results are summarized in Tables 3-4 below; these are the results on which the multimarker AUC calculations are based. These Tables list the AUCs achieved in ROC curves for the biomarker alone—$AUC_{BM}$, and the AUC for the full model achieved for the biomarker with demographics (age, gender, BMI and cohort)—$AUC_{full}$, and their corresponding p values.

In brief, markers were identified that could identify JSN progression modestly (best single biomarker AUC 0.65; multimarker AUC 0.55) and OST more strongly (best single biomarker AUC 0.67; multimarker AUC 0.61). Considering only the biomarker (peptide) capability and prediction of knee level progression, 6 peptides achieved AUC≥0.65 for JSN progression (PGCA, APOH, AACT ×3 peptides, and PHLD), 2 peptides for OST progression (PLF4 and CSCL7), and 6 peptides for KL progression (CFAH, SAMP, HEP2 ×2 peptides, C1R, APOB). The multimarker AUCs for person level progression were somewhat stronger than for knee level progression (Table 3 compared with Table 4) with multimarker AUC 0.67 for OST progression. Considering only the biomarker (peptide) capability and prediction of person level progression, the highest single biomarker AUC was achieved for CXCL7 with AUC 0.70 for prediction of OST. $AUC_{BM}$ in the tables below refers to the AUC with the biomarker alone; $AUC_{full}$ in the tables refers to the AUC calculated when the biomarker and the age, gender and BMI of the subject were considered.

TABLE 3

Top 10 peptides for prediction of knee level Progression from non-depleted serum. Multimarker AUCs based on top 8 peptides.

| OST AUCs and p values for peptides | Peptides predicting OST (SEQ ID NO: X) Multi-marker AUC = 0.61 | JSN AUCs and p values for peptides | Peptides predicting JSN (SEQ ID NO: X) Multi-marker AUC = 0.55 | KL AUCs and p values for peptides | Peptides predicting KL (SEQ ID NO: X) Multi-marker AUC = 0.50 |
|---|---|---|---|---|---|
| $0.67_{BM}/0.69_{full}$ (p = 0.001/0.002) | PLF4 (99) | $0.62_{BM}/0.70_{full}$ (p = 0.019/0.076) | PGCA (96) | $0.67_{BM}/0.82_{full}$ (p = 0.003/0.004) | CFAH (35) |
| $0.67_{BM}/0.67_{full}$ (p = 0.0099/0.013) | CXCL7 (57) | $0.62_{BM}/0.73_{full}$ (p = 0.029/0.016) | APOH (18) | $0.65_{BM}/0.79_{full}$ (p = 0.009/0.018) | SAMP (104) |
| $0.62_{BM}/0.63_{full}$ (p = 0.012/0.006) | ANT3 (14) | $0.61_{BM}/0.70_{full}$ (p = 0.011/0.027) | SAMP (104) | $0.62_{BM}/0.80_{full}$ (p = 0.016/0.029) | TSP1 (112) |
| $0.62_{BM}/0.65_{full}$ (p = 0.008/0.003) | AACT (8) | $0.65_{BM}/0.71_{full}$ (p = 0.029/0.044) | AACT (10) | $0.66_{BM}/0.79_{full}$ (p = 0.021/0.138) | HEP2 (76) |
| $0.63_{BM}/0.65_{full}$ (p = 0.01/0.002) | AACT (10) | $0.64_{BM}/0.71_{full}$ (p = 0.021/0.023) | AACT (8) | $0.65_{BM}/0.80_{full}$ (p = 0.022/0.035) | C1R (22) |
| $0.63_{BM}/0.62_{full}$ (p = 0.031/0.053) | THRB (110) | $0.63_{BM}/0.65_{full}$ (p = 0.01/0.002) | AACT (9) | $0.65_{BM}/0.77_{full}$ (p = 0.019/0.073) | APOB (15) |
| $0.61_{BM}/0.63_{full}$ (p = 0.017/0.008) | AACT (9) | $0.63_{BM}/0.71_{full}$ (p = 0.015/0.021) | CFAH (35) | $0.63_{BM}/0.76_{full}$ (p = 0.039/0.74) | FINC (71) |
| $0.59_{BM}/0.62_{full}$ (p = 0.0397/0.040) | ITIH4 (86) | $0.66_{BM}/0.69_{full}$ (p = 0.065/0.075) | PHLD (98) | $0.66_{BM}/0.80_{full}$ (p = 0.061/0.173) | HEP2 (77) |

TABLE 3-continued

Top 10 peptides for prediction of knee level Progression from non-depleted serum. Multimarker AUCs based on top 8 peptides.

| OST AUCs and p values for peptides | Peptides predicting OST (SEQ ID NO: X) Multi-marker AUC = 0.61 | JSN AUCs and p values for peptides | Peptides predicting JSN (SEQ ID NO: X) Multi-marker AUC = 0.55 | KL AUCs and p values for peptides | Peptides predicting KL (SEQ ID NO: X) Multi-marker AUC = 0.50 |
|---|---|---|---|---|---|
| $0.59_{BM}/0.62_{full}$ (p = 0.061/0.063) | CO8B (51) | $0.59_{BM}/0.68_{full}$ (p = 0.040/0.139) | TSP1 (112) | $0.61_{BM}/0.77_{full}$ (p = 0.072/0.439) | PGCA (96) |
| $0.60_{BM}/0.62_{full}$ (p = 0.046/0.044) | PLMN (100) | $0.64_{BM}/0.71_{full}$ (p = 0.068/0.041) | THRB (110) | $0.62_{BM}/0.77_{full}$ (p = 0.044/0.33) | FINC (70) |

These multimarker AUCs are based on the top 8 peptides and cross-validated as described in the statistical methods. BM is the AUC for the biomarker alone; full is the AUC for the biomarker plus demographics (age, gender, and BMI).

TABLE 4

Top 8 peptides for prediction of person level Progression from non-depleted serum.

| OST AUCs and p values for peptides | Peptides predicting OST (SEQ ID NO: X) Multi-marker AUC = 0.67 | JSN AUCs and p values for peptides | Peptides predicting JSN (SEQ ID NO: X) Multi-marker AUC = 0.50 | KL AUCs and p values for peptides | Peptides predicting KL (SEQ ID NO: X) Multi-marker AUC = 0.57 |
|---|---|---|---|---|---|
| $0.69_{BM}/0.70_{full}$ (p = 0.003/0.007) | CO8B (51) | $0.63_{BM}/0.70_{full}$ (p = 0.020/0.038) | TSP1 (112) | $0.68_{BM}/0.69_{full}$ (p = 0.005/0.005) | CFAH (35) |
| $0.70_{BM}/0.71_{full}$ (p = 0.004/0.005) | PLF4 (99) | $0.66_{BM}/0.70_{full}$ (p = 0.025/0.015) | CFAH (35) | $0.62_{BM}/0.64_{full}$ (p = 0.014/0.044) | TSP1 (112) |
| $0.66_{BM}/0.67_{full}$ (p = 0.017/0.059) | PRG4 (101) | $0.69_{BM}/0.69_{full}$ (p = 0.025/0.027) | THRB (110) | $0.67_{BM}/0.67_{full}$ (p = 0.007/0.038) | SAMP (104) |
| $0.64_{BM}/0.66_{full}$ (p = 0.024/0.055) | PRG4 (102) | $0.59_{BM}/0.68_{full}$ (p = 0.054/0.011) | HRG (81) | $0.65_{BM}/0.68_{full}$ (p = 0.027/0.128) | APOB (15) |
| $0.64_{BM}/0.71_{full}$ (p = 0.018/0.019) | ANT3 (14) | $0.62_{BM}/0.68_{full}$ (p = 0.048/0.029) | APOH (18) | $0.64_{BM}/0.67_{full}$ (p = 0.015/0.049) | AACT (9) |
| $0.64_{BM}/0.66_{full}$ (p = 0.029/0.122) | C4BPA (26) | $0.62_{BM}/0.67_{full}$ (p = 0.064/0.042) | AACT (8) | $0.64_{BM}/0.66_{full}$ (p = 0.017/0.061) | AACT (8) |
| $0.71_{BM}/0.73_{full}$ (p = 0.006/0.007) | CXCL7 (57) | $0.66_{BM}/0.67_{full}$ (p = 0.054/0.080) | PHLD (98) | $0.66_{BM}/0.68_{full}$ (p = 0.032/0.083) | C1R (22) |
| $0.63_{BM}/0.66_{full}$ (p = 0.051/0.187) | C4BPA (25) | $0.60_{BM}/0.67_{full}$ (p = 0.079/0.059) | AACT (9) | $0.66_{BM}/0.67_{full}$ (p = 0.031/0.095) | C1R (23) |

These multimarker AUCs are based on the top 8 peptides and cross-validated as described in the statistical methods. BM is the AUC for the biomarker alone; full is the AUC for the biomarker plus demographics (age, gender, and BMI).

2a.2. Diagnostic Analysis—

By multimarker cross-validated AUCs, markers were identified that could diagnose quite strongly at a knee level and person level, all definitions of Osteoarthritis including JSN (AUC 0.71 knee level, 0.66 person level), OST (AUC 0.70 knee level and person level) and KL grade (AUC 0.77 knee level and 0.74 person level). Considering only the biomarker (peptide) capability and prediction of knee level diagnosis, 2 peptides achieved AUC≥0.65 for a JSN diagnosis (CRTAC1 (also denoted as CRAC1) and CO5), 2 peptides for an OST diagnosis (CRTAC1 ×2 peptides), and 3 peptides for a KL based diagnosis (CRTAC1 ×2 peptides and SHBG). Considering only the biomarker (peptide) capability and prediction of person-level diagnosis, 5 peptides achieved AUC≥0.65 for a JSN diagnosis (CRTAC1, C4BPA, LUM, CO5 and PCOC1), 1 peptide for an OST diagnosis (CRTAC1 peptides), and all 8 top peptides for a KL based diagnosis (CRTAC1 ×2 peptides, PCOC1, CO8G, LUM, COMP, CO6A3 and CO5). The highest single biomarker AUCs for diagnosis were achieved for CRTAC1 (peptide GVASLFAGR) for all definitions of osteoarthritis with AUCs for the biomarker alone ranging from 0.67-0.71 and AUCs ranging form 0.80-0.88 with addition of demographics (age, gender and BMI). One Q9NQ79_CRAC1 (CRTAC1 encoded) peptide, corresponding to Cartilage Acidic Protein 1 (aliases include ASPIC and CEP-68), an extracellular matrix protein found in cartilage, bone and lung, passed a false discovery rate (FDR) threshold (that accounts for multiple testing) of <0.01 as a diagnostic of osteoarthritis based on OST or KL grade (knee and person level) and for JSN (knee level).

TABLE 5

Top 8 peptides for prediction of knee level Diagnosis from non-depleted serum.

| OST AUCs and p values for peptides | Peptides diagnosing OST (SEQ ID NO: X) Multi-marker AUC = 0.70 | JSN AUCs and p values for peptides | Peptides diagnosing JSN (SEQ ID NO: X) Multi-marker AUC = 0.71 | KL AUCs and p values for peptides | Peptides diagnosing KL (SEQ ID NO: X) Multi marker AUC = 0.77 |
|---|---|---|---|---|---|
| $0.71_{BM}/0.82_{full}$ (p = 1.60E−06/0.0001) | CRAC1 (1) | $0.68_{BM}/0.85_{full}$ (p = 1.45E−05/0.001) | CRAC1 (1) | $0.74_{BM}/0.88_{full}$ (p = 7.91E−07/6.77E−05) | CRAC1 (1) |
| $0.66_{BM}/0.80_{full}$ (p = 5.77E−05/0.0007) | CRAC1 (2) | $0.61_{BM}/0.83_{full}$ (p = 0.0002/0.004) | CXCL7 (57) | $0.67_{BM}/0.86_{full}$ (p = 6.61E−05/0.0006) | CRAC1 (2) |
| $0.62_{BM}/0.77_{full}$ (p = 0.005/0.036) | COMP (54) | $0.63_{BM}/0.83_{full}$ (p = 0.001/0.029) | C4BPA (25) | $0.65_{BM}/0.83_{full}$ (p = 0.003/0.049) | SHBG (105) |
| $0.63_{BM}/0.77_{full}$ (p = 0.015/0.149) | CO6A3 (49) | $0.63_{BM}/0.83_{full}$ (p = 0.002/0.019) | COMP (54) | $0.64_{BM}/0.84_{full}$ (p = 0.003/0.017) | COMP (54) |
| $0.63_{BM}/0.77_{full}$ (p = 0.009/0.0997) | SHBG (105) | $0.63_{BM}/0.83_{full}$ (p = 0.003/0.054) | LUM (90) | $0.62_{BM}/0.85_{full}$ (p = 0.004/0.016) | CO8G (52) |
| $0.59_{BM}/0.76_{full}$ (p = 0.016/0.245) | PCOC1 (95) | $0.65_{BM}/0.84_{full}$ (p = 0.008/0.0515) | CO5 (44) | $0.63_{BM}/0.83_{full}$ (p = 0.006/0.118) | PCOC1 (95) |
| $0.57_{BM}/0.77_{full}$ (p = 0.052/0.203) | CO8G (52) | $0.61_{BM}/0.83_{full}$ (p = 0.004/0.018) | TIMP1 (111) | $0.64_{BM}/0.83_{full}$ (p = 0.015/0.120) | CO6A3 (49) |
| $0.58_{BM}/0.76_{full}$ (p = 0.059/0.602) | LUM (90) | $0.64_{BM}/0.83_{full}$ (p = 0.005/0.047) | C4BPA (26) | $0.62_{BM}/0.83_{full}$ (p = 0.007/0.153) | LUM (90) |

These multimarker AUCs are based on the top 8 peptides and cross-validated as described in the statistical methods. Data above in bold denote results passing an FDR multiple testing threshold of 0.05 to 0.01. BM is the AUC for the biomarker alone; full is the AUC for the biomarker plus demographics (age, gender, and BMI).

TABLE 6

Top 8 peptides for prediction of person level Diagnosis from non-depleted serum.

| OST AUCs and p values for peptides | Peptides diagnosing OST (SEQ ID NO: X) Multi-marker AUC = 0.70 | JSN AUCs and p values for peptides | Peptides diagnosing JSN (SEQ ID NO: X) Multi-marker AUC = 0.66 | KL AUCs and p values for peptides | Peptides diagnosing KL (SEQ ID NO: X) Multi-marker AUC = 0.74 |
|---|---|---|---|---|---|
| $0.74_{BM}/0.84_{full}$ (p = 1.86E−06/5.43E−05) | CRAC1 (1) | $0.67_{BM}/0.80_{full}$ (p = 0.0002/0.015) | CRAC1 (1) | $0.76_{BM}/0.88_{full}$ (p = 8.05E−07/1.42E−05) | CRAC1 (1) |
| $0.69_{BM}/0.82_{full}$ (p = 0.00019/0.0009) | CRAC1 (2) | $0.66_{BM}/0.78_{full}$ (p = 0.002/0.014) | C4BPA (25) | $071/0.85_{full}$ (p = 8.37E−05/7.31E−05) | CRAC1 (2) |
| $0.64_{BM}/0.78_{full}$ (p = 0.002/0.026) | COMP (54) | $0.65_{BM}/0.76_{full}$ (p = 0.004/0.038) | LUM (90) | $0.66_{BM}/0.81_{full}$ (p = 0.002/0.044) | PCOC1 (95) |
| $0.64_{BM}/0.77_{full}$ (p = 0.0096/0.099) | CO6A3 (49) | $0.67_{BM}/0.77_{full}$ (p = 0.007/0.047) | CO5 (44) | $0.65_{BM}/0.82_{full}$ (p = 0.003/0.010) | CO8G (52) |
| $0.61_{BM}/0.77_{full}$ (p = 0.017/0.208) | PCOC1 (95) | $0.66_{BM}/0.77_{full}$ (p = 0.006/0.101) | PCOC1 (95) | $0.65_{BM}/0.80_{full}$ (p = 0.008/0.139) | LUM (90) |
| $0.59_{BM}/0.77_{full}$ (p = 0.032/0.129) | CO8G (52) | $0.60_{BM}/0.78_{full}$ (p = 0.001/0.012) | CXCL7 (57) | $0.65_{BM}/0.81_{full}$ (p = 0.002/0.015) | COMP (54) |
| $0.63_{BM}/0.77_{full}$ (p = 0.031/0.180) | ACTG (11) | $0.63_{BM}/0.76_{full}$ (p = 0.006/0.052) | COMP (54) | $0.65_{BM}/0.80_{full}$ (p = 0.011/0.097) | CO6A3 (49) |
| $0.63_{BM}/0.76_{full}$ (p = 0.095/0.799) | CO5 (44) | $0.64_{BM}/0.78_{full}$ (p = 0.0002/0.015) | CO5 (45) | $0.66_{BM}/0.80_{full}$ (p = 0.030/0.449) | CO5 (44) |

These multimarker AUCs are based on the top 8 peptides and cross-validated as described in the statistical methods. Data above in bold denote results passing an FDR multiple testing threshold of 0.05 to 0.01. BM is the AUC for the biomarker alone; full is the AUC for the biomarker plus demographics (age, gender, and BMI).

2b. Depleted Serum Proteomics (Using Original Ratios)

2b.1. Progression Analysis

TABLE 7

Top 8 peptides for prediction of knee level Progression from depleted serum. Multimarker AUCs based on top 8 peptides.

| Peptides predicting OST (SEQ ID NO: X) Multimarker AUC = 0.50 knee level/0.61 person level | Peptides predicting JSN (SEQ ID NO: X) Multimarker AUC = 0.50 knee and person level | Peptides predicting KL (SEQ ID NO: X) Multimarker AUC = 0.50 knee and person level |
|---|---|---|
| CXCL7 (57) | CO4B (43) | KNG1 (88) |
| C4BPA (25) | PGCA (97) | A2AP (4) |
| C4BPB (27) | FCN3 (67) | CO6A3 (50) |
| C4BPA (26) | CD44 (28) | A2AP (5) |
| ITIH4 (86) | TSP4 (113) | HGFA (78) |
| PLMN (100) | TETN (107) | CO2 (41) |
| A2AP (5) | FINC (71) | PRG4 (102) |
| LYAM1 (93) | ECM1 (59) | DOPO (58) |

2b.2. Diagnostic Analysis—

TABLE 8

Top 8 peptides for prediction of knee level Diagnosis from depleted serum. Multimarker AUCs based on top 8 peptides.

| Peptides diagnosing OST (SEQ ID NO: X) Multimarker AUC = 0.74 knee level/0.77 person level | Peptides diagnosing JSN (SEQ ID NO: X) Multimarker AUC = 0.67 knee level/0.77 person level | Peptides diagnosing KL (SEQ ID NO: X) Multimarker AUC = 0.75 knee level/0.89 person level |
|---|---|---|
| A2AP (4) | A2AP (4) | A2AP (4) |
| A2AP (5) | A2AP (5) | CO2 (41) |
| CO2 (41) | CO2 (41) | CRAC1 (1) |
| FA5 (61) | FA5 (61) | CRAC1 (2) |
| CO5 (44) | CRAC1 (1) | FA5 (61) |
| CRAC1 (1) | COMP (55) | CO6A3 (49) |
| CRAC1 (2) | CRAC1 (2) | CO5 (44) |
| CERU (33) | HRG (79) | COMP (55) |

TABLE 9

Top 8 peptides for prediction of person level Diagnosis from depleted serum and using actin normalization. Multimarker AUCs based on top 8 peptides.

| | | | | Peptides diagnosing KL (SEQ ID NO: X) Multimarker AUC = 0.89 Multimarker AUC = 0.88 with actin normalization |
|---|---|---|---|---|
| OST p values for peptides | Peptides diagnosing OST (SEQ ID NO: X) Multimarker AUC = 0.77 Multimarker AUC = 0.81 with actin normalization | JSN p values for peptides | Peptides diagnosing JSN (SEQ ID NO: X) Multimarker AUC = 0.77 Multimarker AUC = 0.78 with actin normalization | KL p values for peptides |
| 7.93E-06 | A2AP (4) | 1.33E-07 | A2AP (4) | 7.83E-11 A2AP (4) |
| 3.97E-05 | A2AP (5) | 5.89E-05 | A2AP (5) | 5.02E-06 CRAC1 (1) |
| 4.76E-05 | CRAC1 (1) | 7.05E-05 | CO2 (41) | 1.83E-05 CO2 (41) |
| 0.000368059 | CRAC1 (2) | 0.000385554 | CRAC1 (1) | 1.99E-05 A2AP (5) |
| 0.000584044 | CO2 (41) | 0.000614719 | COMP (55) | 4.39E-05 CRAC1 (2) |
| 0.001053574 | FA5 (61) | 0.003020118 | CRAC1 (2) | 0.000735498 COMP (55) |
| 0.007678923 | CO6A3 (49) | 0.003279263 | FA5 (61) | 0.001071963 FA5 (61) |
| 0.00822894 | CO5 (44) | 0.009168162 | CO6A3 (49) | 0.0036707 FBLN3 (64) |

3. ELISA Biomarker Results

A total of 18 separate Osteoarthritis-related biomarkers were evaluated in this study:
- Serum: CD44, CD163, collagen 3, COMP, haptoglobin, hemopexin, kininogen, ceruloplasmin, hyaluronan, TBG, Vitamin D, TSG6, CD14
- Urine: CTX1beta, CTX1alpha, (CTX1alpha/CTX1beta), CTX2, ceruloplasmin, haptoglobin The most significant results are summarized Table 10 below; these are the results for which the biomarker alone or the full model (biomarker, age, gender, BMI and cohort) achieved p<0.05. This Table lists the AUC achieved in ROC curves for the biomarker alone—$AUC_{BM}$, and the AUC for the full model achieved for the biomarker with demographics (age, gender, BMI and cohort)—$AUC_{full}$, and their corresponding p values.

In brief, progression markers for JSN include sHaptoglobin (knee and person level, (s) indicates serum measured), sCD44 (knee and person level), sHemopexin (knee level), and sCeruloplasmin (person level). We did not identify any strong progression markers for OST but we identified several strong markers of progression based upon KL grade change, including sHaptoglobin (knee and person level), sCD44 (knee level), and sCeruloplasmin (knee and person level). Of these, sHaptoglobin is the strongest progression marker.

Some strong diagnostic markers were identified for JSN (knee and person level) including sKininogen, sHyaluronan, sCD14, uCeruloplasmin and uCTX1alpha/CTX1beta ratio ((u) indicates urine measured). In addition, some strong diagnostic markers were identified for OST (knee and person level) including sKininogen, sCD14, and uCTX1alpha/CTX1beta ratio. Of these sKininogen and sHyaluronan are extremely strong diagnostic markers.

TABLE 10

Summary of most significant ELISA Results for Osteophyte (OST), Joint Space Narrowing (JSN), and Kellgren Lawrence (KL) grade progression and diagnostic phenotypes at a knee (black) and person-based level (red).

| Biomarker s = serum, u = urine (Relative amount in progressors) | PROGRESSION | | | DIAGNOSIS | | |
|---|---|---|---|---|---|---|
| | AUC for OST | AUC for JSN | AUC for KL | AUC for OST | AUC for JSN | AUC for KL |
| sHaptoglobin (higher) | $0.62_{BM}$ / $0.63_{full}$ (p = 0.056/0.036) | $0.70_{BM}$ / $0.71_{full}$ (p = 0.002/0.003) $0.75_{BM}$ / $0.75_{full}$ (p=0.001/0.002) | $0.68_{BM}$ / $0.82_{full}$ (p = 0.023/0.021) $0.70_{BM}$ / $0.68_{full}$ (p=0.011/0.015) | $0.69_{BM}$ / $0.78_{full}$ (p=0.0013/0.179) | $0.59_{BM}$ / $0.85_{full}$ (p = 0.045/0.289) | |
| sCD44 (lower) | | $0.59_{BM}$ / $0.71_{full}$ (p = 0.051/0.021) $0.59_{BM}$ / $0.65_{full}$ (p=0.048/0.050) | $0.57_{BM}$ / $0.81_{full}$ (p = 0.15/0.033) | | | |
| sHemopexin (higher) | | $0.65_{BM}$ / $0.71_{full}$ (p = 0.018/0.04) | | | | |
| sKininogen | | | | $0.67_{BM}$ / $0.82_{full}$ (p = 0.000003/0.00012) $(0.68_{BM}$ / $0.82_{full})$ (p=0.00004/0.0005) | $0.60_{BM}$ / $0.85_{full}$ (p = 0.001/0.073) $(0.61_{BM}$ / $0.79_{full})$ (p=0.001/0.065) | $0.65_{BM}$ / $0.87_{full}$ (p = 0.00004/0.0023) $(0.67_{BM}$ / $0.84_{full})$ (p=0.00009/0.002) |
| sHyaluronan (higher) | $0.62_{BM}$ / $0.65_{full}$ (p = 0.099/0.033) | | | $0.67_{BM}$ / $0.79_{full}$ (p = 0.004/0.133) | $0.71_{BM}$ / $0.88_{full}$ (p = 0.001/0.016) $(0.72_{BM}$ / $0.80_{full})$ (p=0.00007/0.046) | $0.71_{BM}$ / $0.86_{full}$ (p = 0.001/0.073) $(0.72_{BM}$ / $0.82_{full})$ (p=0.00016/0.069) |
| sCD14 (higher) | | | | $0.63_{BM}$ / $0.77_{full}$ (p = 0.031/0.157) $(0.64_{BM}$ / $0.78_{full})$ (p=0.018/0.128) | $0.65_{BM}$ / $0.85_{full}$ (p = 0.008/0.013) $(0.70_{BM}$ / $0.80_{full})$ (p=0.0002/0.001) | $0.67_{BM}$ / $0.85_{full}$ (p = 0.0008/0.043) $(0.67_{BM}$ / $0.82_{full})$ (p=0.003/0.055) |

TABLE 10-continued

Summary of most significant ELISA Results for Osteophyte (OST), Joint Space Narrowing (JSN), and Kellgren Lawrence (KL) grade progression and diagnostic phenotypes at a knee (black) and person-based level (red).

| Biomarker s = serum, u = urine (Relative amount in progressors) | PROGRESSION | | | DIAGNOSIS | | |
|---|---|---|---|---|---|---|
| | AUC for OST | AUC for JSN | AUC for KL | AUC for OST | AUC for JSN | AUC for KL |
| sCD163 | $0.58_{BM}$/ $0.68_{full}$ (p = 0.43/ 0.046) | | | | | |
| sCeruloplasmin (lower) | | $0.63_{BM}$/ $\underline{0.66_{full}}$ $\underline{(p=0.032/}$ $\underline{0.054)}$ | $0.65_{BM}$/ $0.82_{full}$ (p = 0.019/ 0.002) $0.62_{BM}$/ $\underline{0.64_{full}}$ $\underline{(p=0.051/}$ $\underline{0.025)}$ | $0.59_{BM}$/ $0.83_{full}$ (p = 0.051/ 0.078) | $0.65_{BM}$/ $0.82_{full}$ (p = 0.019/ 0.002) | |
| uCeruloplasmin (lower)[urine1] | | | | $0.63_{BM}$/ $0.85_{full}$ (p = 0.007/ 0.064) $\underline{(0.66_{BM}/}$ $\underline{0.82_{full})}$ $\underline{(p=0.002/}$ $\underline{0.017)}$ | | |
| uCeruloplasmin (lower)[urine2] | | | $0.60_{BM}$/ $0.79_{full}$ (p = 0.027/ 0.130) | $0.65_{BM}$/ $0.86_{full}$ (p = 0.004/ 0.129) $\underline{(0.68_{BM}/}$ $\underline{0.82_{full})}$ $\underline{(p=0.001/}$ $\underline{0.031)}$ | $0.63_{BM}$/ $0.85_{full}$ (p = 0.013/ 0.152) $\underline{(0.61_{BM}/}$ $\underline{0.81_{full})}$ $\underline{(p=0.035/}$ $\underline{0.465)}$ | |
| uCTX1alpha/ CTX1beta (higher)[urine1] | | | $0.62_{BM}$/ $0.79_{full}$ (p = 0.019/ 0.149) $\underline{0.61_{BM}/}$ $\underline{0.79_{full}}$ $\underline{(p=0.045/}$ $\underline{0.556)}$ | $0.62_{BM}$/ $0.84_{full}$ (p = 0.017/ 0.63) | $0.64_{BM}$/ $0.85_{full}$ (p = 0.013/ 0.232) $\underline{(0.61_{BM}/}$ $\underline{0.82_{full})}$ $\underline{(p=0.041/}$ $\underline{0.779)}$ | |
| uCTX1alpha/ CTX1beta (higher)[urine2] | | | $0.62_{BM}$/ $0.80_{full}$ (p = 0.038/ 0.146) | $0.63_{BM}$/ $0.85_{full}$ (p = 0.022/ 0.418) $\underline{(0.65_{BM}/}$ $\underline{0.80_{full})}$ $\underline{(p=0.010/}$ $\underline{0.257)}$ | $0.65_{BM}$/ $0.85_{full}$ (p = 0.025/ 0.165) $\underline{(0.62_{BM}/}$ $\underline{0.82_{full})}$ $\underline{(p=0.053/}$ $\underline{0.518)}$ | |
| uCTX1 (higher)[urine2] | | | | $\underline{(0.63_{BM}/}$ $\underline{0.79_{full})}$ $\underline{(p=0.028/}$ $\underline{0.338)}$ | $0.64_{BM}$/ $0.85_{full}$ (p = 0.050/ 0.224) | |
| sVitamin D binding protein (lower) | | $0.58_{BM}$/ $\underline{0.62_{full}}$ $\underline{(p=0.209/}$ $\underline{0.052)}$ | | $0.60_{BM}$/ $0.82_{full}$ (p = 0.022/ 0.797) | $0.62_{BM}$/ $0.83_{full}$ (p = 0.0085/ 0.413) | |

AUCs not underlined are knee-based results and AUCs underlined are Person-based results. BM is the AUC for the biomarker alone; full is the AUC for the biomarker plus demographics (age, gender, BMI and cohort).

Conclusions

More diagnostic than prognostic biomarkers were discovered. Non-depleted serum worked as well or better than depleted serum, therefore, the validation does not necessarily require serum depletion of the most abundant proteins. By proteomics, our strongest prognostic biomarkers were for OST and included serum CO8B and serum PLF4. By proteomics, our strongest diagnostic biomarker was serum CRTAC1 (encoding Cartilage Acidic Protein 1), which diagnosed all phenotypes of OA and passed a 1% FDR rate.

By ELISA, serum Haptoglobin was the strongest predictor of progression and predicted JSN indicative of cartilage loss. Immunoaffinity depletion of high abundance plasma proteins is frequently employed to enhance detection of lower abundance proteins in both shotgun and targeted proteomic analyses. MARS columns afford highly repeatable and efficient plasma protein depletions and a global enrichment in non-target plasma proteins of 2-4 fold. Tu et al., *J Proteome Res* 9(10):4982-91 (2010). We have identified serum haptoglobin to be a strong marker of knee osteoarthritis progression but it is ordinarily depleted from blood biospecimens (by both the MARS-7 and MARS-14 Human protein depletion columns by Agilent) prior to mass spectrometry analysis. Future analyses of non-depleted serum will permit addition of haptoglobin to the panel of analytes surveilled. By ELISA, serum Kininogen and serum Hyaluronan were the strongest diagnostic markers of knee OA predicting most strongly OST and JSN, respectively.

Normalization

We developed a methodology to select peptides capable of acting as normalization peptides in multiple reaction monitoring (MRM) and mass spectrometry analyses to control for intensity loading and variation of efficiency of Mars-14 protein depletion of serum or other biospecimen. We identified 14 proteins that could serve as normalization controls that are superior or equivalent to the standard methodology of normalizing to mean signal intensity. Specifically, we identified 4 normalization peptides from 4 proteins that are superior to mean intensity normalization (the standard methodology) and 21 peptides from 14 proteins that are equivalent or slightly better than standard methodology for normalization. Details are provided below. For MRM, these candidates can be run to evaluate and control for potential technical variation related to MARS-14 depletion. They might also be used in analyses of non-depleted samples to control for variation introduced by sample processing.

Table 11 below lists the proteins that are depleted by the MARS-14 column. Depletion efficiency varies across samples. This introduces variability in sample results. The standard practice is to normalize signal intensities for each peptide of interest with overall signal intensity of all peptides. Obviously, when the sample depletion has been variable, the data normalization to overall intensity will introduce variability and error in the results.

TABLE 11

List of blood proteins depleted by MARS-14.

| | MARS Hu-14 proteins | Primary Protein Name |
|---|---|---|
| 1 | albumin | ALBU_BOVIN |
| | | ALBU_HUMAN |
| 2 | IgG | IGHG3_HUMAN |
| 3 | IgA | |
| 4 | transferrin | TRFE_HUMAN |
| 5 | haptoglobin | HPT_HUMAN |
| 6 | antitrypsin | A1AT_HUMAN |
| 7 | fibrinogen | FIBA_HUMAN |
| 8 | alpha2-macroglobulin | A2MG_HUMAN |
| 9 | alpha1-acid glycoprotein | — |
| 10 | IgM | — |
| 11 | apolipoprotein AI | APOA1_HUMAN |
| 12 | apolipoprotein AII | — |
| 13 | complement C3 | CO3_HUMAN |
| 14 | transthyretin | TTHY_HUMAN |

One method we devised was to normalize based on total mean signal intensity using all signals except those emanating from any residual amounts of the proteins in the above list of proteins (that should have been depleted but that are generally depleted with varying efficiencies)—'targeted mean total intensity' normalization.

Our goal was to find a peptide or protein that could serve as a normalization control, i.e. a "housekeeping protein" that would eliminate the need to normalize to total mean intensity or targeted mean total intensity described above. For a normalization peptide to benefit the analysis, it should produce better signals than normalization in the standard way using mean overall intensity. Therefore, ideally, we would like to find a normalization peptide or protein that is superior to either of these methods. The test of superiority is to compare qq plots for the sample data normalized by the targeted mean total intensity (our refinement of standard practice) vs normalized to the candidate normalization protein or peptide.

TABLE 12

Normalization peptides (total of 4 peptides) that are superior to normalization by mean intensity.

| Modified Peptide Sequence (SEQ ID NO:) | Peptide Teller Probability | Primary Protein Name | Superior or Equivalent to Standard Method of Normalization |
|---|---|---|---|
| FVFGTTPEDILR (112) | 1 | TSP1_HUMAN | Superior |
| ALEQDLPVNIK (40) | 1 | CNDP1_HUMAN | Superior |
| SEAYNTFSER (61) | 0.89 | FA5_HUMAN | Superior |
| IALGGLLFPASNLR (105) | 0.99 | SHBG_HUMAN | Superior |

TABLE 13

Normalization peptides (total of 21) that are slightly better or equivalent to normalization by mean intensity.

| Modified Peptide Sequence (SEQ ID NO:) | Peptide Teller Probability | Primary Protein Name | Superior or Equivalent to Standard Method of Normalization |
|---|---|---|---|
| ICLDLQAPLYK (99) | 1 | PLF4_HUMAN | Equivalent |
| FQSVFTVTR (123) | 1 | C1QC_HUMAN | Equivalent |
| IFYNQQNHYDGSTGK (124) | 1 | ADIPO_HUMAN | Equivalent |

TABLE 13-continued

Normalization peptides (total of 21) that are slightly better or equivalent to normalization by mean intensity.

| Modified Peptide Sequence (SEQ ID NO:) | Peptide Teller Probability | Primary Protein Name | Superior or Equivalent to Standard Method of Normalization |
|---|---|---|---|
| EWVAIESDSVQPVPR (125) | 0.96 | CNDP1_HUMAN | Equivalent |
| SVVLIPLGAVDDGEHSQNEK (126) | 1 | CNDP1_HUMAN | Slightly Better |
| LVPFATELHER (127) | 0.66 | APOA4_HUMAN | Slightly Better |
| VAPEEHPVLLTEAPLNPK (11) | 0.84 | ACTG_HUMAN | Equivalent |
| FTGSQPFGQGVEHATANK (143) | 1 | TSP1_HUMAN | Equivalent |
| EFNPLVIVGLSK (62) | 0.74 | FA5_HUMAN | Equivalent |
| VLSIAQAHSPAFSCEQVR (128) | 0.94 | CD14_HUMAN | Equivalent |
| SITLFVQEDR (129) | 0.99 | TSP1_HUMAN | Equivalent |
| AEAESLYQSK (130) | 0.99 | K2C1_HUMAN | Equivalent |
| NALWHTGNTPGQVR (131) | 0.95 | TSP1_HUMAN | Equivalent |
| AIHLDLEEYR (132) | 1 | CNDP1_HUMAN | Equivalent |
| AGTLDLSLTVQGK (133) | 0.99 | TSP1_HUMAN | Slightly Better |
| EENFYVDETTVVK (134) | 0.9 | CBG_HUMAN | Equivalent |
| DNNSIITR (135) | 0.61 | CHLE_HUMAN | Equivalent |
| VVLSSGSGPGLDLPLVLGLPLQLK (136) | 1 | SHBG_HUMAN | Equivalent |
| DNCQYVYNVDQR (137) | 0.99 | TSP1_HUMAN | Equivalent |
| LFLGALPGEDSSTSFCLNGLWAQGQR (138) | 0.6 | SHBG_HUMAN | Equivalent |
| HNEVWHLVGITSWGEGCAQR (139) | 0.77 | FA11_HUMAN | Equivalent |

Overall, the following numbers of peptides were identified as normalization controls from 14 proteins: TSP-1 (6), CNDP1 (4), FA5 (2), SHBG (3), and one each for PLF4, C1Qc, ADIPO, APOA4, ACTG, CD14, K2C1, CBG, CHLE and FA11. Three additional peptides identified in our human specimen analyses also cover 3 of these proteins, including the following:

76969249 515.7786 2
(SEQ ID NO: 140)
GPDPSSPAFR
TSP1_HUMAN Thrombospondin-1 OS = Homo sapiens GN = THBS1 PE = 1 SV = 2;

(SEQ ID NO: 141)
76967646 520.31244 2HITSLEVIK PLF4_HUMAN
Platelet factor 4 OS = Homo sapiens GN = PF4 PE = 1 SV = 2;

76968171 522.26917
(SEQ ID NO: 142)
2LDVDQALNR
SHBG_HUMAN Sex hormone-binding globulin OS = Homo sapiens GN = SHBG PE = 1 SV = 2

Additional analyses have identified two other potential normalization peptides in the Carbonic anhydrase 1 protein:

```
CAH1_HUMAN (peptide 8856058)
                                          (SEQ ID NO: 144)
GGPFSDSYR Carbonic anhydrase 1 - Homo sapiens (8848161)
                                          (SEQ ID NO: 145)
GGPFSDSYR
```

Multimarker Analysis I Using Serum Biomarkers and Clinical Covariates

Analysis was performed to identify biomarkers that could add value for disease classification over and above clinical parameters. Serum biomarkers previously selected by the literature (E biomarkers) could modestly increase classification of Control vs. Disease (C v D). In contrast, the novel serum biomarkers (M biomarkers) discovered in the study could significantly increase this classification.

C v D (Control v Disease)

Clinical covariates could classify C v D moderately well (AUC, ca. 0.78). Biomarkers previously selected by the literature and measured by ELISA (E biomarkers) could increase classification (AUC, 0.81). In contrast, the novel M biomarkers discovered in the study could significantly increase classification (AUC, 0.97). Adding both E and M biomarkers to clinical covariates increased the AUC to 0.99.

N v P (Non-Progressor v Progressor, Person)

Clinical covariates were not significant. Adding E+M biomarkers improved classification to AUC=0.69.

PO1 v PO2 (Non-Progressor v Progressor, Osteophyte)

For clinical covariates, only gender was significant and classification was AUC=0.65. No E biomarkers were selected by the analysis. Addition of M biomarkers improved classification to AUC=0.72.

PJ1 v PJ2 (Non-Progressor v Progressor, JSN)

Clinical covariates were not significant. No M biomarkers were selected by the analysis. Adding E biomarkers improved classification to AUC=0.69.

PK1 v PK2 (Non-Progressor v Progressor, KL)

For clinical covariates, only cohort was significant for classification. No M biomarkers were selected by the analysis. Adding E biomarkers resulted in classification AUC=0.65.

General Methods

Biomarker Selection

For each outcome, and each set of biomarkers (class E and class M, separately), biomarker selection was performed using the lasso selection method with the R package "glmnet", and selecting the tuning parameter using the built in 10-fold cross-validation.

ROC Analysis

For each outcome, following biomarker selection, the observations were randomly split in half to generate a training and a test set. For the training set, two logistic regression models were fit: one with clinical parameters only (CP Training), and the other with clinical parameters+biomarkers (CP+B Training). Coefficients from the logistic regression training models were applied to the respective test sets (CP Test and CP+B Test). ROC AUC was calculated for each of the training and test sets. This process was repeated 50 times for C v D and 10 times for all other analyses and the average AUC (+/−sd) was calculated. A summary of the results is shown below in Tables 14-18.

TABLE 14

| Clinical Outcome | Biomarkers | ROC AUC | | | |
| --- | --- | --- | --- | --- | --- |
| | | CP Training Set | CP Test Set | CP + B Training Set | CP + B Test Set |
| C v D | E | 0.802 (0.049) | 0.763 (0.059) | 0.946 (0.028) | 0.807 (0.075) |
| C v D | M | 0.822 (0.043) | 0.792 (0.047) | 1.00 (0.000) | 0.974 (0.020) |
| C v D | E + M | 0.844 (0.050) | 0.793 (0.056) | 1.000 (0.000) | 0.990 (0.011) |

The numbers are the mean AUC over 10 random splits with standard deviations given in parenthesis.

TABLE 15

| Clinical Outcome | Biomarkers | ROC AUC | | | |
| --- | --- | --- | --- | --- | --- |
| | | CP Training Set | CP Test Set | CP + B Training Set | CP + B Test Set |
| N v P | E | 0.677 (0.087) | 0.441 (0.103) | 0.938 (0.074) | 0.641 (0.125) |
| N v P | M | 0.689 (0.056) | 0.504 (0.061) | 0.884 (0.033) | 0.662 (0.085) |
| N v P | E + M | 0.725 (0.127) | 0.538 (0.080) | 0.930 (0.154) | 0.686 (0.070) |

The numbers are the mean AUC over 10 random splits with standard deviations given in parenthesis.

TABLE 16

| Clinical Outcome | Biomarkers | ROC AUC | | | |
| --- | --- | --- | --- | --- | --- |
| | | CP Training Set | CP Test Set | CP + B Training Set | CP + B Test Set |
| PO1 v PO2 | E | no E biomarkers selected | no E biomarkers selected | no E biomarkers selected | no E biomarkers selected |
| PO1 v PO2 | M | 0.720 (0.057) | 0.587 (0.083) | 0.916 (0.052) | 0.721 (0.115) |
| PO1 v PO2 | E + M | no E biomarkers selected | no E biomarkers selected | no E biomarkers selected | no E biomarkers selected |

The numbers are the mean AUC over 10 random splits with standard deviations given in parenthesis.

TABLE 17

ROC AUC

| Clinical Outcome | Bio-markers | CP Training Set | CP Test Set | CP + B Training Set | CP + B Test Set |
|---|---|---|---|---|---|
| PJ1 v PJ2 | E | 0.681 (0.063) | 0.459 (0.094) | 0.971 (0.040) | 0.686 (0.127) |
| PJ1 v PJ2 | M | no M biomarkers selected | no M biomarkers selected | no M biomarkers selected | no M biomarkers selected |
| PJ1 v PJ2 | E + M | no M biomarkers selected | no M biomarkers selected | no M biomarkers selected | no M biomarkers selected |

The numbers are the mean AUC over 10 random splits with standard deviations given in parenthesis.

TABLE 18

ROC AUC

| Clinical Outcome | Bio-markers | CP Training Set | CP Test Set | CP + B Training Set | CP + B Test Set |
|---|---|---|---|---|---|
| PK1 v PK2 | E | 0.700 (0.053) | 0.549 (0.102) | 0.836 (0.076) | 0.646 (0.094) |
| PK1 v PK2 | M | no M biomarkers selected | no M biomarkers selected | no M biomarkers selected | no M biomarkers selected |
| PK1 v PK2 | E + M | no M biomarkers selected | no M biomarkers selected | no M biomarkers selected | no M biomarkers selected |

The numbers are the mean AUC over 10 random splits with standard deviations given in parenthesis.

Additional Information

For the C v D analysis, 19 M biomarkers were selected by the lasso method. Additional analysis was performed to identify the M biomarkers in the selection path and to test the chain of biomarkers in the path. Using 10× repeat halves sampling, it was observed that the first two biomarkers, CRAC1 (SEQ ID NO: 1) and A2AP (SEQ ID NO: 4) from depleted samples, gave an AUC of 0.948. R-scripts containing the outputs from the logistic regression analyses contain additional information for the biomarkers used in the models. The relative p-values in each model may be used to select the more significant biomarkers for that model whereby the lower p-values indicate more significant biomarkers in the model.

I. Analysis for C/D Outcomes
Y=1 if D; Y=0 if C;

There are totally 126 observations with no missing in Y (89 with Y=1, 70.6%). Clinical covariates: gender, age, bmi.

I.1. Analysis Using Only Clinical Covariates.

We fit a logistic regression, and found that age and bmi are significant with p-values 0.0027 and 0.0002, respectively. The AUC (i.e. area under the ROC) is 0.7756.

I.2. Analysis Using Clinical Covariates and E Markers.

There are 19 E markers and 96 observations with complete E markers (63 with Y=1, 65.6%). We conducted lasso selection using the R package "glmnet", and selected the tuning parameter using the built-in 10-fold cross-validation. It selects 6 E markers: HA, kinno, vitd_binding, coll3, hemopexin, cd14. The AUC is 0.9192.

To evaluate the value of added E markers for prediction of C/D outcomes, we randomly split the data into half training and half testing datasets, and did this 50 times. Based on the training data, we fit two logistic regression: (i) using the clinical covariates only; (ii) using the clinical covariates plus the selected 6 E markers. Then, we applied the fitted scores to both training and testing data to compute AUC. The results are summarized in Tables 14-18. The numbers are the mean AUC over 50 random splits with standard deviations given in parenthesis.

I.3. Analysis Using Clinical Covariates and M Markers.

There are 238 M makers and 110 observations with complete M markers (77 with Y=1, 70.0%). We conducted lasso selection using the R package "glmnet", and selected the tuning parameter using the built-in 10-fold cross-validation. It selects 19 M markers: TENX (SEQ ID NO: 106), FCGBP (SEQ ID NO: 66), C4BPB (SEQ ID NO: 27), A2AP (SEQ ID NO: 4), APOE (SEQ ID NO: 17), C1QC (SEQ ID NO: 20), CO6A3 (SEQ ID NO: 50), CRAC1 (SEQ ID NO: 1), FA5 (SEQ ID NO: 61) from depleted samples; and GELS (SEQ ID NO: 72), CXCL7 (SEQ ID NO: 57), ACTG (SEQ ID NO: 11), CFAI (SEQ ID NO: 37), CO5 (SEQ ID NO: 46), CO6A3 (SEQ ID NO: 49), CO8G (SEQ ID NO: 52), CRAC1 (SEQ ID NO: 1), FINC (SEQ ID NO: 70), PCOC1 (SEQ ID NO: 95) from nondepleted samples. The AUC is 1.

To evaluate the value of added M markers for prediction of C/D outcomes, we randomly split the data into half training and half testing datasets, and did this 50 times. Based on the training data, we fit two logistic regression: (i) using the clinical covariates only; (ii) using the clinical covariates plus the selected 19 M markers (here we use logistic regression with ridge penalty since some M markers may be highly correlated). Then, we applied the fitted scores to both training and testing data to compute AUC. The results are summarized in Table 14.

I.4. The Selection Path for M Markers and Associated AUC.

The selected 19 M markers in order are: CRAC1 (SEQ ID NO: 1) (nondepleted), A2AP (SEQ ID NO: 4) (depleted), CO8G (SEQ ID NO: 52) (nondepleted), CXCL7 (SEQ ID NO: 57) (nondepleted), CO5 (SEQ ID NO: 46) (nondepleted), FCGBP (SEQ ID NO: 66) (depleted), PCOC1 (SEQ ID NO: 95) (nondepleted), CFAI (SEQ ID NO: 37) (nondepleted), CO6A3 (SEQ ID NO: 50) (depleted), GELS (SEQ ID NO: 72) (nondepleted), C4BPB (SEQ ID NO: 27) (depleted), CO6A3 (SEQ ID NO: 49) (nondepleted), ACTG (SEQ ID NO: 11) (nondepleted), CRAC1 (SEQ ID NO: 1) (deplated), FINC (SEQ ID NO: 70) (nondepleted), C1QC (SEQ ID NO: 20) (depleted), TENX (SEQ ID NO: 106) (depleted), APOE (SEQ ID NO: 17) (depeleted), FA5 (SEQ ID NO: 61) (depleted).

To evaluate the value of top k (k=1, 2, . . . , 19) selected M markers for prediction of C/D outcomes, we randomly split the data into half training and half testing datasets, and did this 10 times. The mean AUCs for testing data are given by: 0.8944272 0.9478328 0.9428793 0.9447368 0.9346749 0.9524768 0.9521672 0.9517028 0.9572755 0.9571207 0.9643963 0.9659443 0.9664087 0.9721362 0.9724458 0.9752322 0.971517 0.976161 0.977709. This suggests that the top 2 selected M markers can already improve the prediction ability sufficiently.

I.5. Analysis Using Clinical Covariates, E and M Markers.

There are 84 observations with complete E and M markers (54 with Y=1, 64.3%). The AUC based on clinical covariates plus the selected 6 E markers and 19 M markers is 1. To evaluate the value of added E and M markers for prediction of C/D outcomes, we randomly split the data into half training and half testing datasets, and did this 50 times. The results are summarized in Table 14.

II. Analysis for N/P Outcomes
Y=1 if P; Y=0 if N;
There are totally 89 complete observations with P/N (66 with Y=1, 74.2%). Clinical covariates: cohort id, gender, age, bmi.

II.1. Analysis Using Only Clinical Covariates.
We fit a logistic regression, and found that none of them are significant. The AUC is 0.5975.

II.2. Analysis Using Clinical Covariates and E Markers.
There are 63 complete observations (47 with Y=1, 74.6%). We conducted lasso selection using the R package "glmnet", and selected the tuning parameter using the built-in 10-fold cross-validation. It selects 6 E markers: cd163, hapto, coll3, hemopexin, ctx2, cd14. The AUC is 0.8484.

To evaluate the value of added E markers for prediction of P/N outcomes, we randomly split the data into half training and half testing datasets, and did this 10 times. Based on the training data, we fit two logistic regression: (i) using the clinical covariates only; (ii) using the clinical covariates plus the selected 6 E markers. Then, we applied the fitted scores to both training and testing data to compute AUC. The results are summarized in Table 15. The numbers are the mean AUC over 10 random splits with standard deviations given in parenthesis.

II.3. Analysis Using Clinical Covariates and M Markers.
There are 77 complete observations (59 with Y=1, 76.6%). We conducted lasso selection using the R package "glmnet", and selected the tuning parameter using the built-in 10-fold cross-validation. It selects 4 M markers: CO8B (SEQ ID NO: 51), CFAH (SEQ ID NO: 35), CRAC1 (SEQ ID NO: 1), HRG (SEQ ID NO: 81) from depleted samples. The AUC is 0.8013.

To evaluate the value of added M markers for prediction of P/N outcomes, we randomly split the data into half training and half testing datasets, and did this 10 times. Based on the training data, we fit two logistic regression: (i) using the clinical covariates only; (ii) using the clinical covariates plus the selected 4 M markers. Then, we applied the fitted scores to both training and testing data to compute AUC. The results are summarized in Table 15.

II.4. Analysis Using Clinical Covariates, E and M Markers.
There are 54 complete observations (41 with Y=1, 75.9%). The AUC based on clinical covariates plus the selected 6 E markers and 4 M markers is 0.8949. To evaluate the value of added E and M markers for prediction of P/N outcomes, we randomly split the data into half training and half testing datasets, and did this 10 times. The results are summarized in Table 15.

III. Analysis for P/O Outcomes
Y=1 if PO2; Y=0 if PO1;
There are totally 82 complete observations with PO1/PO2 (54 with Y=1, 65.85%). Clinical covariates: cohort id, gender, age, bmi.

III.1. Analysis Using Only Clinical Covariates.
We fit a logistic regression, and found that only gender is significant. The AUC is 0.6548.

III.2. Analysis Using Clinical Covariates and E Markers.
There are 61 complete observations (41 with Y=1, 67.2%). We conducted lasso selection using the R package "glmnet", and selected the tuning parameter using the built-in 10-fold cross-validation. None of the E markers are selected.

III.3. Analysis Using Clinical Covariates and M Markers.
There are 71 complete observations (47 with Y=1, 66.2%). We conducted lasso selection using the R package "glmnet", and selected the tuning parameter using the built-in 10-fold cross-validation. It selects 5 M markers: LYAM1 (SEQ ID NO: 93) from depleted samples, KLKB1 (SEQ ID NO: 87), CXCL7 (SEQ ID NO: 57), CO8B (SEQ ID NO: 51), ANT3 (SEQ ID NO: 14) from nondepleted samples. The AUC is 0.8555.

To evaluate the value of added M markers for prediction of P/O outcomes, we randomly split the data into half training and half testing datasets, and did this 10 times. Based on the training data, we fit two logistic regression: (i) using the clinical covariates only; (ii) using the clinical covariates plus the selected 5 M markers. Then, we applied the fitted scores to both training and testing data to compute AUC. The results are summarized in Table 16.

IV. Analysis for P/J Outcomes
Y=1 if PJ2; Y=0 if PJ1;
There are totally 74 complete observations with PJ1/PJ2 (40 with Y=1, 54.1%). Clinical covariates: cohort id, gender, age, bmi.

IV.1. Analysis Using Only Clinical Covariates.
We fit a logistic regression, and found that none of them are significant. The AUC is 0.6279.

IV.2. Analysis Using Clinical Covariates and E Markers.
There are 52 complete observations (27 with Y=1, 51.9%). We conducted lasso selection using the R package "glmnet", and selected the tuning parameter using the built-in 10-fold cross-validation. It selects 6 E markers: hapto, vitd_binding, cd44, hemopexin, cerulo_serum, ctx2. The AUC is 0.9185.

To evaluate the value of added E markers for prediction of P/N outcomes, we randomly split the data into half training and half testing datasets, and did this 10 times. Based on the training data, we fit two logistic regression: (i) using the clinical covariates only; (ii) using the clinical covariates plus the selected 6 E markers. Then, we applied the fitted scores to both training and testing data to compute AUC. The results are summarized in Table 17.

IV.3. Analysis Using Clinical Covariates and M Markers.
There are 66 complete observations (37 with Y=1, 56.1%). We conducted lasso selection using the R package "glmnet", and selected the tuning parameter using the built-in 10-fold cross-validation. None of the M markers are selected.

V. Analysis for P/K Outcomes
Y=1 if PK2; Y=0 if PK1;
There are totally 89 complete observations with PK1/PK2 (31 with Y=1, 34.8%). Clinical covariates: cohort id, gender, age, bmi.

V.1. Analysis Using Only Clinical Covariates.
We fit a logistic regression, and found that only cohort id is significant. The AUC is 0.7269.

V.2. Analysis Using Clinical Covariates and E Markers.
There are 63 complete observations (18 with Y=1, 28.6%). We conducted lasso selection using the R package "glmnet", and selected the tuning parameter using the built-in 10-fold cross-validation. It selects 1 E marker: hapto. The AUC is 0.7605.

To evaluate the value of added E markers for prediction of P/N outcomes, we randomly split the data into half training and half testing datasets, and did this 10 times. Based on the training data, we fit two logistic regression: (i) using the clinical covariates only; (ii) using the clinical covariates plus the selected 1 E marker. Then, we applied the fitted scores to both training and testing data to compute AUC. The results are summarized in Table 18.

V.3. Analysis Using Clinical Covariates and M Markers.
There are 77 complete observations (28 with Y=1, 36.4%). We conducted lasso selection using the R package "glmnet", and selected the tuning parameter using the built-in 10-fold cross-validation. None of the M markers are selected.

Multimarker Analysis II Using Serum Biomarkers and Clinical Covariates

Analysis Based on M Markers: M141-M257

I. Analysis for C/D Outcomes

Y=1 if D; Y=0 if C;

I.0. Selection Based on M Markers Only.

There are totally 118 observations with no missing in Y (83 with Y=1, 70.3%). We conducted lasso selection using the R package "glmnet", and selected the tuning parameter using the built-in 10-fold cross-validation. It selects 5 M markers: CXCL7 (SEQ ID NO: 57), CO6A3 (SEQ ID NO: 49), CO8G (SEQ ID NO: 52), CRAC1 (SEQ ID NO: 1), COMP (SEQ ID NO: 54) from nondepleted samples.

I.1. Analysis Using Clinical Covariates and M Markers.

To evaluate the value of added M markers for prediction of C/D outcomes, we randomly split the data into half training and half testing datasets, and did this 50 times. Based on the training data, we fit two logistic regression: (i) using the clinical covariates only; (ii) using the clinical covariates plus the selected 5 M markers (here we use logistic regression with ridge penalty since some M markers may be highly correlated). Then, we applied the fitted scores to both training and testing data to compute AUC. The results are summarized in Table 19 below:

TABLE 19

| | Training Data | Testing Data |
|---|---|---|
| Clinical + M markers | 0.908 (0.032) | 0.851 (0.047) |

I.2. Analysis Using Clinical Covariates, E and M Markers.

To evaluate the value of added E and M markers for prediction of C/D outcomes, we randomly split the data into half training and half testing datasets, and did this 50 times. The results are summarized in Table 20 below:

TABLE 20

| | Training Data | Testing Data |
|---|---|---|
| Clinical + E + M markers | 0.969 (0.022) | 0.893 (0.038) |

II. Analysis for N/P Outcomes

Y=1 if P; Y=0 if N;

II.0. Selection Based on M Markers Only.

There are totally 83 observations with no missing in Y (62 with Y=1, 74.7%). We conducted lasso selection using the R package "glmnet", and selected the tuning parameter using the built-in 10-fold cross-validation. It selects 10 M markers: PLF4 (SEQ ID NO: 99), CO8B (SEQ ID NO: 51), CERU (SEQ ID NO: 29), CFAH (SEQ ID NO: 35), FINC (SEQ ID NO: 70), HRG (SEQ ID NO: 81), PRG4 (SEQ ID NO: 101), SAMP (SEQ ID NO: 104), TSP4 (SEQ ID NO: 113) from nondepleted samples.

II.1. Analysis Using Clinical Covariates and M Markers.

To evaluate the value of added M markers for prediction of P/N outcomes, we randomly split the data into half training and half testing datasets, and did this 50 times. Based on the training data, we fit two logistic regression: (i) using the clinical covariates only; (ii) using the clinical covariates plus the selected 10 M markers (here we use logistic regression with ridge penalty since some M markers may be highly correlated). Then, we applied the fitted scores to both training and testing data to compute AUC. The results are summarized in Table 21 below:

TABLE 21

| | Training Data | Testing Data |
|---|---|---|
| Clinical + M markers | 0.902 (0.078) | 0.726 (0.080) |

II.2. Analysis Using Clinical Covariates, E and M Markers.

To evaluate the value of added E and M markers for prediction of P/N outcomes, we randomly split the data into half training and half testing datasets, and did this 50 times. The results are summarized in Table 22 below:

TABLE 22

| | Training Data | Testing Data |
|---|---|---|
| Clinical + E + M markers | 0.937 (0.100) | 0.739 (0.100) |

III. Analysis for P/O Outcomes

Y=1 if PO2; Y=0 if PO1;

III.0. Selection Based on M Markers Only.

There are totally 76 complete observations with PO1/PO2 (50 with Y=1, 65.8%). We conducted lasso selection using the R package "glmnet", and selected the tuning parameter using the built-in 10-fold cross-validation. It selects 7 M markers: PLF4 (SEQ ID NO: 99), KLKB1 (SEQ ID NO: 87), CO8B (SEQ ID NO: 51), ANT3 (SEQ ID NO: 14), ACTG (SEQ ID NO: 11), CD44 (SEQ ID NO: 28), CFAI (SEQ ID NO: 37) from nondepleted samples.

III.1. Analysis Using Clinical Covariates and M Markers.

To evaluate the value of added M markers for prediction of PO1/PO2 outcomes, we randomly split the data into half training and half testing datasets, and did this 50 times. Based on the training data, we fit two logistic regression: (i) using the clinical covariates only; (ii) using the clinical covariates plus the selected 7 M markers (here we use logistic regression with ridge penalty since some M markers may be highly correlated). Then, we applied the fitted scores to both training and testing data to compute AUC. The results are summarized in Table 23 below:

TABLE 23

| | Training Data | Testing Data |
|---|---|---|
| Clinical + M markers | 0.900 (0.052) | 0.776 (0.059) |

III.2. Analysis Using Clinical Covariates, E and M Markers.

No E markers were selected.

IV. Analysis for P/J Outcomes

Y=1 if PJ2; Y=0 if PJ1;

IV.0. Selection Based on M Markers Only.

There are totally 70 complete observations with PJ1/PJ2 (50 with Y=1, 54.3%). We conducted lasso selection using the R package "glmnet", and selected the tuning parameter using the built-in 10-fold cross-validation. No M markers were selected.

V. Analysis for P/K Outcomes

Y=1 if PK2; Y=0 if PK1;

IV.0. Selection Based on M Markers Only.

There are totally 83 complete observations with PK1/PK2 (30 with Y=1, 36.1%). We conducted lasso selection using the R package "glmnet", and selected the tuning parameter using the built-in 10-fold cross-validation. No M markers were selected.

Multimarker Analysis III Using Serum Biomarkers
Methods

We generated further multi-marker models based on the markers we identified. Inferential methods and predictive methods were used depending on the structure of the data. For a person-level analysis, logistic regression was used to compute p-values and confidence intervals. Covariates included age, sex, BMI, and cohort. The effect of a biomarker was added to a model containing these covariates and a likelihood-ratio test was used to assess the significance of the biomarker after accounting for the covariates. A biomarker was considered significant if it surpassed a Benjamini-Hochberg FDR threshold of 10%. For a knee-level analysis the dependence arising from paired observations must be considered. We used the generalized estimating equation (GEE) method to account for the correlation structure. A biomarker was added to a model containing base covariates and its significance was assessed by a Wald statistic.

Predictive models were used to assess discrimination through the AUC. We used feature selection coupled with ridge regression, a form of penalized regression, for all models implemented in the glmnet R package. Penalized regression is often used for predictive models to constrain the size of coefficients to lessen the effects of overfitting the data. Feature selection consisted of selecting the top 8 markers with the lowest p-values, which is a simple but effective method for the numbers of peptides in the current data set. Leave-one-out cross-validation was used in which selecting tuning parameters and carrying out feature selection was repeated at each iteration of cross-validation to mimic the process of fitting a model to new data. In sum, all multimarker AUCs have been properly cross-validated. For knee-level (paired) analysis, the leave-one-out cross-validation scheme was modified to a leave-sample-out scheme so that the test set was independent of the training set.

Results

A summary of the results is shown in Tables 24-29. Depleted Serum—Multimarker Analyses; Dx=Diagnosis (Predict Knee OA Diagnosis); Px=Prognosis (Predict Knee OA Progression).

TABLE 24

| JSN (SEQ ID NO: X) | p value peptide alone (pval_pep_only) | p value adjusted for age, gender, BMI and cohort (pval_base_full) |
|---|---|---|
| knee JSN Dx depleted | AUC = 0.77 | |
| A2AP (4) | 9.26E-05 | 0.046613974 |
| A2AP (5) | 2.42E-05 | 0.142711257 |
| CO2 (41) | 9.76E-05 | 0.078527954 |
| COMP (55) | 0.001556863 | 0.124035832 |
| FA5 (61) | 0.002710746 | 0.209278011 |
| CO5 (44) | 0.009185471 | 0.865395357 |
| CRAC1 (1) | 0.018818294 | 0.011011104 |
| SHBG (105) | 0.014916307 | 0.803569832 |
| knee JSN person Dx depleted | AUC = 0.80 | |
| A2AP (4) | 3.31E-07 | 0.008051178 |
| A2AP (5) | 2.81E-05 | 0.292406073 |
| CO2 (41) | 8.72E-05 | 0.162905105 |
| COMP (55) | 0.001303611 | 0.180539523 |
| CRAC1 (1) | 0.003128843 | 0.006690407 |
| FA5 (61) | 0.005274008 | 0.367965374 |
| CO5 (44) | 0.022968897 | 0.863307127 |
| CRAC1 (2) | 0.024934734 | 0.051344408 |
| knee JSN Px depleted | AUC = 0.41 | |
| CO4B (43) | 0.033584489 | 0.054265435 |
| FCN3 (67) | 0.076630893 | 0.020166429 |
| CO8B (51) | 0.017661819 | 0.011132744 |

TABLE 24-continued

| JSN (SEQ ID NO: X) | p value peptide alone (pval_pep_only) | p value adjusted for age, gender, BMI and cohort (pval_base_full) |
|---|---|---|
| FINC (70) | 0.040090816 | 0.045404495 |
| PGCA (97) | 0.065006579 | 0.105883213 |
| TSP4 (113) | 0.076843539 | 0.02082132 |
| FINC (71) | 0.051256407 | 0.091823154 |
| TETN (107) | 0.05530156 | 0.041645638 |
| knee JSN person Px depleted | AUC = 0.39 | |
| PGCA (97) | 0.026293441 | 0.046827678 |
| CO4B (43) | 0.023475468 | 0.015862788 |
| TENX (106) | 0.039475824 | 0.033732372 |
| FCN3 (67) | 0.18678107 | 0.107948938 |
| C4BPA (25) | 0.064638445 | 0.030266734 |
| TSP1 (112) | 0.13133037 | 0.18210438 |
| CO8B (51) | 0.113256944 | 0.07456324 |
| HRG (79) | 0.1438498 | 0.062444406 |

TABLE 25

| KL (SEQ ID NO: X) | p value peptide alone (pval_pep_only) | p value adjusted for age, gender, BMI and cohort (pval_base_full) |
|---|---|---|
| knee KL Dx depleted | AUC 0.82 | |
| A2AP (4) | 7.71E-05 | 0.00276514 |
| CO2 (41) | 5.90E-05 | 0.002320056 |
| A2AP (5) | 8.93E-06 | 0.062148737 |
| FA5 (61) | 0.000470793 | 0.058126283 |
| COMP (55) | 0.001082738 | 0.12106214 |
| CO5 (44) | 0.000562536 | 0.229466647 |
| CRAC1 (1) | 0.004460634 | 0.001449587 |
| CRAC1 (2) | 0.033778439 | 0.009978404 |
| knee KL person Dx depleted | AUC = 0.89 | |
| A2AP (4) | 1.50E-07 | 0.000135815 |
| A2AP (5) | 9.64E-05 | 0.140576823 |
| CRAC1 (1) | 0.000106179 | 6.44E-05 |
| CO2 (41) | 0.00023168 | 0.024410373 |
| CRAC1 (2) | 0.001782088 | 0.00062291 |
| COMP (55) | 0.006752536 | 0.186567751 |
| FA5 (61) | 0.00570514 | 0.108817433 |
| CO5 (44) | 0.019947104 | 0.406134156 |
| knee KL Px depleted | AUC = 0.43 | |
| A2AP (4) | 0.038108974 | 0.38563753 |
| KNG1 (88) | 0.020411121 | 0.391748644 |
| HGFA (78) | 0.037729146 | 0.03308354 |
| PRG4 (102) | 0.128488782 | 0.333151487 |
| AFAM (12) | 0.120643826 | 0.844521484 |
| DOPO (58) | 0.13172217 | 0.264987362 |
| HNC (71) | 0.068344045 | 0.133741621 |
| CO8B (51) | 0.062727522 | 0.03532693 |
| knee KL person Px depleted | AUC = 0.39 | |
| KNG1 (88) | 0.052000668 | 0.315327177 |
| HGFA (78) | 0.054701983 | 0.056927485 |
| A2AP (4) | 0.10641075 | 0.563510596 |
| FAS (61) | 0.140793944 | 0.673707755 |
| TSP1 (112) | 0.148443778 | 0.390538592 |
| PGCA (97) | 0.135584259 | 0.183730223 |
| TENX (106) | 0.149867446 | 0.055623532 |
| FINC (71) | 0.164143337 | 0.229058614 |

TABLE 26

| OST (SEQ ID NO: X) | p value peptide alone (pval_pep_only) | p value adjusted for age, gender, BMI and cohort (pval_base_full) |
|---|---|---|
| knee OST Dx depleted | AUC = 0.66 | |
| A2AP (5) | 3.35E−05 | 0.022657938 |
| A2AP (4) | 0.001538871 | 0.021017782 |
| FA5 (61) | 0.000257061 | 0.006428595 |
| CO2 (41) | 0.002198765 | 0.036511365 |
| CO5 (44) | 0.001100287 | 0.024126793 |
| COMP (55) | 0.004918696 | 0.096093869 |
| SHBG (105) | 0.005156474 | 0.10532715 |
| CO6A3 (49) | 0.008366857 | 0.086848008 |
| knee OST Dx person depleted | AUC = 0.82 | |
| A2AP (5) | 2.09E−05 | 0.017678836 |
| A2AP (4) | 6.34E−05 | 0.01810586 |
| CO2 (41) | 0.000414071 | 0.024973599 |
| FAS (61) | 0.001001698 | 0.014610139 |
| CRAC1 (1) | 0.002263888 | 0.007041871 |
| CO5 (44) | 0.006050591 | 0.091904821 |
| COMP (55) | 0.009743019 | 0.152299519 |
| CRAC1 (2) | 0.02066252 | 0.028329279 |
| knee OST Px depleted | AUC = 0.49 | |
| CXCL7 (57) | 0.003370215 | 0.003050257 |
| C4BPA (25) | 0.003682397 | 0.005664358 |
| C4BPB (27) | 0.003909035 | 0.00385861 |
| C4BPA (26) | 0.006334513 | 0.007556145 |
| A2AP (4) | 0.038641621 | 0.029667601 |
| ITIH4 (86) | 0.041117212 | 0.033451744 |
| PLMN (100) | 0.042208729 | 0.03218861 |
| HRG (83) | 0.033182707 | 0.01429709 |
| knee OST person Px depleted | AUC = 0.54 | |
| C4BPA (25) | 0.011047566 | 0.011004835 |
| C4BPB (27) | 0.014086851 | 0.010277587 |
| C4BPA (26) | 0.011958263 | 0.012290566 |
| CXCL7 (57) | 0.013978919 | 0.015727039 |
| LYAM1 (93) | 0.071115015 | 0.024706069 |
| A2AP (4) | 0.126628387 | 0.024897652 |
| TSP1 (112) | 0.101650546 | 0.03394991 |
| FINC (71) | 0.099794158 | 0.146642438 |

Non-Depleted Serum - multimarker analyses;
Dx = diagnosis (predict knee OA diagnosis);
Px = prognosis (predict knee OA progression)

TABLE 27

| JSN (SEQ ID NO: X) | p value peptide alone (pval_pep_only) | p value adjusted for age, gender, BMI and cohort (pval_base_full) |
|---|---|---|
| knee JSN Dx nondepleted | AUC = 0.71 | |
| CRAC1 (1) | 1.45E−05 | 0.001334661 |
| CXCL7 (57) | 0.000220209 | 0.004033964 |
| C4BPA (25) | 0.001092182 | 0.029609534 |
| COMP (54) | 0.001921796 | 0.019441399 |
| LUM (90) | 0.003127373 | 0.053918866 |
| CO5 (44) | 0.007557254 | 0.051506718 |
| TIMP1 (111) | 0.003709593 | 0.017775522 |
| C4BPA (26) | 0.005168882 | 0.046877637 |
| knee JSN person Dx nondepleted | AUC = 0.66 | |
| CRAC1 (1) | 0.00026204 | 0.014921219 |
| C4BPA (25) | 0.002059188 | 0.013830002 |
| LUM (90) | 0.003509795 | 0.038433173 |
| CO5 (44) | 0.007188587 | 0.047295814 |
| PCOC1 (95) | 0.006323501 | 0.10111207 |
| CXCL7 (57) | 0.001410986 | 0.011528214 |
| COMP (54) | 0.005892446 | 0.051513052 |
| CO5 (45) | 0.010430159 | 0.054225697 |
| knee JSN Px nondepleted | AUC = 0.55 | |
| PGCA (96) | 0.018643447 | 0.076340059 |
| APOH (18) | 0.029178909 | 0.015538341 |
| SAMP (104) | 0.011280848 | 0.026954743 |
| AACT (10) | 0.028545301 | 0.044498503 |
| AACT (8) | 0.020730449 | 0.02340926 |
| AACT (9) | 0.015384508 | 0.02138342 |

TABLE 27-continued

| JSN (SEQ ID NO: X) | p value peptide alone (pval_pep_only) | p value adjusted for age, gender, BMI and cohort (pval_base_full) |
|---|---|---|
| CFAH (35) | 0.030877701 | 0.008199734 |
| PHLD (98) | 0.065419311 | 0.075331479 |
| TSP1 (112) | 0.040324672 | 0.139428301 |
| THRB (110) | 0.153796326 | 0.031114401 |
| knee JSN person Px nondepleted | AUC = 0.45 | |
| TSP1 (112) | 0.020309869 | 0.038161024 |
| CFAH (35) | 0.025234989 | 0.015467182 |
| THRB (110) | 0.025437875 | 0.026717885 |
| HRG (81) | 0.05431721 | 0.01105114 |
| APOH (18) | 0.048284307 | 0.028696354 |
| AACT (8) | 0.064355392 | 0.042526395 |
| PHLD (98) | 0.054354097 | 0.079726494 |
| AACT (9) | 0.079176188 | 0.058988993 |

TABLE 28

| KL (SEQ ID NO: X) | p value peptide alone (pval_pep_only) | p value adjusted for age, gender, BMI and cohort (pval_base_full) |
|---|---|---|
| knee KL Dx nondepleted | AUC = 0.77 | |
| CRAC1 (1) | 7.91E−07 | 6.77E−05 |
| CRAC1 (2) | 6.61E−05 | 0.000611469 |
| SHBG (105) | 0.002780496 | 0.049018578 |
| COMP (54) | 0.003119022 | 0.016939944 |
| CO8G (52) | 0.004439784 | 0.01618559 |
| PCOC1 (95) | 0.005867991 | 0.118372629 |
| CO6A3 (49) | 0.014832263 | 0.120147034 |
| LUM (90) | 0.006899035 | 0.152788954 |
| knee KL person Dx nondepleted | AUC = 0.74 | |
| CRAC1 (1) | 8.05E−07 | 1.42E−05 |
| CRAC1 (2) | 8.37E−05 | 7.31E−05 |
| PCOC1 (95) | 0.001985962 | 0.044267004 |
| CO8G (52) | 0.003214569 | 0.010196682 |
| LUM (90) | 0.007570064 | 0.138934545 |
| COMP (54) | 0.002099819 | 0.015488264 |
| CO6A3 (49) | 0.0110763 | 0.097029625 |
| CO5 (44) | 0.03014129 | 0.449289979 |
| knee KL Px nondepleted | AUC = 0.43 | |
| CFAH (35) | 0.003413853 | 0.003720699 |
| SAMP (104) | 0.008874549 | 0.01757112 |
| TSP1 (112) | 0.016396723 | 0.029173098 |
| HEP2 (76) | 0.021317466 | 0.138072515 |
| C1R (22) | 0.022324877 | 0.035342549 |
| APOB (15) | 0.019423193 | 0.073310656 |
| FINC (71) | 0.038839588 | 0.741216237 |
| HEP2 (77) | 0.061398201 | 0.173258732 |
| PGCA (96) | 0.071967152 | 0.438930963 |
| FINC (70) | 0.044013606 | 0.329880745 |
| knee KL person Px nondepleted | AUC = 0.57 | |
| CFAH (35) | 0.004647535 | 0.004744558 |
| TSP1 (112) | 0.014072412 | 0.044301897 |
| SAMP (104) | 0.007169693 | 0.038267836 |
| APOB (15) | 0.026721333 | 0.127645336 |
| AACT (9) | 0.014781295 | 0.049356758 |
| AACT (8) | 0.017046792 | 0.061084614 |
| C1R (22) | 0.031947667 | 0.082794302 |
| C1R (23) | 0.030621922 | 0.095021007 |

TABLE 29

| OST (SEQ ID NO: X) | p value peptide alone (pval_pep_only) | p value adjusted for age, gender, BMI and cohort (pval_base_full) |
|---|---|---|
| knee OST Dx nondepleted | AUC = 0.70 | |
| CRAC1 (1) | 1.60E−06 | 0.00013426 |
| CRAC1 (2) | 5.77E−05 | 0.0007071 |

TABLE 29-continued

| OST (SEQ ID NO: X) | p value peptide alone (pval_pep_only) | p value adjusted for age, gender, BMI and cohort (pval_base_full) |
|---|---|---|
| COMP (54) | 0.004838815 | 0.036180336 |
| CO6A3 (49) | 0.015033517 | 0.149650103 |
| SHBG (105) | 0.009303617 | 0.099766058 |
| PCOC1 (95) | 0.016164645 | 0.244959617 |
| CO8G (52) | 0.052018531 | 0.202674481 |
| LUM (90) | 0.058692947 | 0.601716961 |
| knee OST Dx person nondepleted | AUC = 0.70 | |
| CRAC1 (1) | 1.86E−06 | 5.43E−05 |
| CRAC1 (2) | 1.86E−06 | 5.43E−05 |
| COMP (54) | 0.002304261 | 0.025690528 |
| CO6A3 (49) | 0.009634809 | 0.098819568 |
| PCOC1 (95) | 0.016841954 | 0.207971822 |
| CO8G (52) | 0.031580042 | 0.128396316 |
| ACTG (11) | 0.030554232 | 0.180275486 |
| CO5 (44) | 0.095059051 | 0.79862693 |
| knee OST Px nondepleted | AUC = 0.61 | |
| PLF4 (99) | 0.001094118 | 0.001590437 |
| CXCL7 (57) | 0.009976718 | 0.012612223 |
| ANT3 (14) | 0.011884039 | 0.006241664 |
| AACT (8) | 0.00821959 | 0.002747701 |
| AACT (10) | 0.010576976 | 0.002088226 |
| THRB (110) | 0.030760839 | 0.053273043 |
| AACT (9) | 0.016720482 | 0.0084448 |
| ITIH4 (86) | 0.039793857 | 0.04003038 |
| CO8B (51) | 0.061264758 | 0.062748503 |
| PLMN (100) | 0.046320809 | 0.044378072 |
| knee OST person Px nondepleted | AUC = 0.67 | |
| CO8B (51) | 0.00274445 | 0.007382756 |
| PLF4 (99) | 0.003710526 | 0.005376922 |
| PRG4 (101) | 0.016806589 | 0.059964262 |
| PRG4 (102) | 0.024390935 | 0.054916368 |
| ANT3 (14) | 0.017572544 | 0.019097753 |
| C4BPA (26) | 0.029402337 | 0.122776322 |
| CXCL7 (57) | 0.005698 | 0.006885551 |
| C4BPA (25) | 0.051311885 | 0.186676691 |

We claim:

1. A method of treating a subject with progression of osteoarthritis, comprising:
   measuring the expression levels of a group of biomarkers in a sample from the subject, wherein the biomarkers measured comprise the complement C1r subcomponent (C1R) peptide of SEQ ID NO: 23, the cartilage acidic protein 1 (CRAC1 or CRTAC1) peptide of SEQ ID NO: 1 or SEQ ID NO: 2, the kininogen-1 (KNG1) peptide of SEQ ID NO: 88, the phosphatidylinositol-glycan-specific phospholipase D (PHLD) peptide of SEQ ID NO: 98, and the vitamin D-binding protein (VTDB) peptide of SEQ ID NO: 116, SEQ ID NO: 118, or SEQ ID NO: 119;
   predicting progression of osteoarthritis in the subject, wherein altered levels of any of the biomarkers measured as compared to a reference level is indicative of progression of osteoarthritis; and
   selecting and administering a therapeutic for treatment of osteoarthritis to the subject identified as having progression of osteoarthritis based on the prediction.

2. The method of claim 1, wherein the biomarkers measured further comprise at least one biomarker selected from the group consisting of antithrombin-III (ANT3), complement factor H (CFAH), and platelet factor 4 (PLF4).

3. The method of claim 2, wherein the biomarkers measured comprise at least two biomarkers selected from the group consisting of ANT3, CFAH, and PLF4.

4. The method of claim 3, wherein the biomarkers measured comprise ANT3, CFAH, and PLF4.

5. The method of claim 3, wherein the at least two biomarkers are selected from the group consisting of the ANT3 peptide of SEQ ID NO: 14, the CFAH peptide of SEQ ID NO: 35, and the PLF4 peptide of SEQ ID NO: 99.

6. The method of claim 3, wherein the levels of the at least two biomarkers are altered in the subject as follows: ANT3 level is decreased, CFAH level is increased, or PLF4 level is increased, as compared to the reference level.

7. The method of claim 1, wherein the biomarkers measured further comprise at least one biomarker selected from the group consisting of alpha-1B-glycoprotein (A1BG), alpha-2-antiplasmin (A2AP), leucine-rich alpha-2-glycoprotein (A2GL), alpha-1-antichymotrypsin (AACT), actin, cytoplasmic 2 (ACTG), afamin (AFAM), apolipoprotein B-100 (APOB), beta-2-glycoprotein 1 (APOH), beta-2-microglobulin (B2MG), complement C1q subcomponent subunit C (C1QC), complement C1r subcomponent-like protein (C1RL), c4b-binding protein alpha chain (C4BPA), c4b-binding protein beta chain (C4BPB), cluster of differentiation 14 (CD14), cluster of differentiation 163 (CD163), cluster of differentiation 44 (CD44), ceruloplasmin (CERU), complement factor B (CFAB), complement factor I (CFAI), complement C1s subcomponent (C1S), complement C2 (CO2), complement C4-B (CO4B), complement C5 (CO5), collagen alpha-3(VI) chain (CO6A3), complement component C8 beta chain (CO8B), complement component C8 gamma chain (CO8G), collagen alpha-1(III) chain (COL3A1), collagen type II C-telopeptide fragments (CTX2), platelet basic protein (CXCL7), dopamine beta-hydroxylase (DOPO), extracellular matrix protein 1 (ECM1), coagulation factor V (FA5), coagulation factor XII (FA12), fibulin-1 (FBLN1), IgG Fc-binding protein (FCGBP), ficolin-3 (FCN3), alpha-2-HS-glycoprotein (FETUA), fibronectin (FINC), gelsolin (GELS), hyaluronan-binding protein 2 (HABP2), haptoglobin, hemopexin (HEMO), heparin cofactor 2 (HEP2), hepatocyte growth factor activator (HGFA), histidine-rich glycoprotein (HRG), hyaluronan, inter-alpha-trypsin inhibitor heavy chain H4 (ITIH4), plasma kallikrein (KLKB1), lumican (LUM), L-selectin (LYAM1), aggrecan core protein (PGCA), plasminogen (PLMN), proteoglycan 4 (PRG4), retinol-binding protein 4 (RET4), serum amyloid P-component (SAMP), tenascin X (TENX), tetranectin (TETN), thyroxine-binding globulin (THBG), prothrombin (THRB), tissue inhibitor metalloproteinase 1 (TIMP1), thrombospondin-1 (TSP1), thrombospondin-4(TSP4), and vitronectin (VTNC).

8. The method of claim 7, wherein the biomarkers measured comprise FA5.

9. The method of claim 1, further comprising:
measuring the level of at least one normalization peptide from a protein selected from beta-Ala-His dipeptidase (CNDP1), sex hormone-binding globulin (SHBG), adiponectin (ADIPO), apolipoprotein A4 (APOA4), keratin, type II cytoskeletal 1 (K2C1), corticosteroid-binding globulin (CBG), carboxylic ester hydrolase (CHLE), coagulation factor XI (FA11), and carbonic anhydrase 1 (CAH1) in the sample from the subject; and
normalizing the levels of the biomarkers measured in the sample from the subject prior to comparing the levels of the biomarkers to the reference level.

10. The method of claim 9, wherein the normalization peptide is selected from the group consisting of the CNDP1 peptide of SEQ ID NO: 40, and the SHBG peptide of SEQ ID NO: 105.

11. The method of claim 1, wherein the sample is serum, plasma, urine, or synovial fluid.

12. The method of claim 11, wherein the sample is serum depleted of at least 7 major serum proteins.

13. The method of claim 12, wherein the serum proteins depleted are selected from the group consisting of albumin, IgG, IgA, transferrin, haptoglobin, anti-trypsin, fibrinogen, alpha 2-macroglobulin, IgM, apolipoprotein AI, apolipoprotein AII, complement C3, and transthyretin.

14. The method of claim 1, wherein the biomarkers are measured using an antibody-based capture method or mass spectrometry.

15. The method of claim 1, wherein the therapeutic for treatment of osteoarthritis is an anti-inflammatory or anti-pain therapeutic comprising a nonsteroidal anti-inflammatory drug (NSAID).

* * * * *